United States Patent
Bourgon et al.

(10) Patent No.: US 12,331,128 B2
(45) Date of Patent: *Jun. 17, 2025

(54) THERAPEUTIC AND DIAGNOSTIC METHODS FOR CANCER

(71) Applicants: Genentech, Inc., South San Francisco, CA (US); Foundation Medicine, Inc., Cambridge, MA (US)

(72) Inventors: Richard Bourgon, South San Francisco, CA (US); David Fabrizio, Cambridge, MA (US); Gregg Fine, South San Francisco, CA (US); Garrett M. Frampton, Cambridge, MA (US); Priti Hegde, South San Francisco, CA (US); Sanjeev Mariathasan, South San Francisco, CA (US); Philip J. Stephens, Cambridge, MA (US); James Xin Sun, Cambridge, MA (US); Roman Yelensky, Newton, MA (US)

(73) Assignees: Genentech, Inc., South San Francisco, CA (US); Foundation Medicine, Inc., Cambridge, MA (US)

( * ) Notice: Subject to any disclaimer, the term of this patent is extended or adjusted under 35 U.S.C. 154(b) by 587 days.

This patent is subject to a terminal disclaimer.

(21) Appl. No.: 17/590,918

(22) Filed: Feb. 2, 2022

(65) Prior Publication Data

US 2022/0153861 A1 May 19, 2022

Related U.S. Application Data

(63) Continuation of application No. 16/115,343, filed on Aug. 28, 2018, now Pat. No. 11,279,767, which is a continuation of application No. PCT/US2017/019682, filed on Feb. 27, 2017.

(60) Provisional application No. 62/405,190, filed on Oct. 6, 2016, provisional application No. 62/301,595, filed on Feb. 29, 2016.

(51) Int. Cl.
| | |
|---|---|
| *C07K 16/28* | (2006.01) |
| *A61K 39/395* | (2006.01) |
| *A61P 35/00* | (2006.01) |
| *G16H 50/30* | (2018.01) |
| *A61K 39/00* | (2006.01) |
| *G16H 20/10* | (2018.01) |

(52) U.S. Cl.
CPC ...... *C07K 16/2896* (2013.01); *A61K 39/3955* (2013.01); *C07K 16/2818* (2013.01); *G16H 50/30* (2018.01); *A61K 2039/505* (2013.01); *A61K 2039/577* (2013.01); *A61P 35/00* (2018.01); *C07K 2317/24* (2013.01); *C07K 2317/76* (2013.01); *G16H 20/10* (2018.01)

(58) Field of Classification Search
None
See application file for complete search history.

(56) References Cited

U.S. PATENT DOCUMENTS

| | | | |
|---|---|---|---|
| 4,366,241 | A | 12/1982 | Tom et al. |
| 4,376,110 | A | 3/1983 | David et al. |
| 4,517,288 | A | 5/1985 | Giegel et al. |
| 4,816,567 | A | 3/1989 | Cabilly et al. |
| 4,837,168 | A | 6/1989 | de Jaeger et al. |
| 4,987,071 | A | 1/1991 | Cech et al. |
| 5,093,246 | A | 3/1992 | Cech et al. |
| 5,116,742 | A | 5/1992 | Cech et al. |
| 5,223,409 | A | 6/1993 | Ladner et al. |
| 5,225,539 | A | 7/1993 | Winter |
| 5,491,224 | A | 2/1996 | Bittner et al. |
| 5,547,835 | A | 8/1996 | Koster |
| 5,585,089 | A | 12/1996 | Queen et al. |
| 5,605,798 | A | 2/1997 | Koster |
| 5,693,761 | A | 12/1997 | Queen et al. |
| 5,693,762 | A | 12/1997 | Queen et al. |
| 6,277,569 | B1 | 8/2001 | Bittner et al. |
| 6,455,258 | B2 | 9/2002 | Bastian et al. |
| 7,943,743 | B2 | 5/2011 | Korman et al. |
| 8,008,449 | B2 | 8/2011 | Korman et al. |

(Continued)

FOREIGN PATENT DOCUMENTS

| | | |
|---|---|---|
| CN | 105209919 A | 12/2015 |
| EP | 430402 B2 | 6/1991 |

(Continued)

OTHER PUBLICATIONS

Abernathy et al., "Two NF1 mutations: Frameshift in the GAP-related domain, and loss of two codons toward the 3' end of the gene," Hum Mutat. 3(4):347-352 (1994).

Aggarwal et al., "Baseline Plasma Tumor Mutation Burden Predicts Response to Pembrolizumab-based Therapy in Patients with Metastatic Non-Small Cell Lung Cancer," Clinical Cancer Research. 26(10):2354-2361 (May 15, 2020) (9 pages).

(Continued)

*Primary Examiner* — Ilia I Ouspenski
(74) *Attorney, Agent, or Firm* — Clark & Elbing LLP; Thomas J. Takara

(57) ABSTRACT

The present invention provides therapeutic and diagnostic methods and compositions for cancer, for example, bladder cancer. The invention provides methods of treating bladder cancer, methods of determining whether a patient suffering from bladder cancer is likely to respond to treatment comprising a PD-L1 axis binding antagonist, methods of predicting responsiveness of a patient suffering from bladder cancer to treatment comprising a PD-L1 axis binding antagonist, and methods of selecting a therapy for a patient suffering from bladder cancer, based on somatic mutation levels of genes of the invention (e.g., somatic mutation levels in a tumor sample obtained from the patient).

13 Claims, 6 Drawing Sheets

Specification includes a Sequence Listing.

(56) References Cited

U.S. PATENT DOCUMENTS

| | | | |
|---|---|---|---|
| 8,354,509 B2 | 1/2013 | Carven et al. | |
| 8,609,089 B2 | 12/2013 | Langermann et al. | |
| 11,066,709 B2 | 7/2021 | Klijn et al. | |
| 11,279,767 B2* | 3/2022 | Bourgon | C12Q 1/6886 |
| 11,300,570 B2 | 4/2022 | Fabrizio et al. | |
| 2003/0143204 A1 | 7/2003 | Lewis et al. | |
| 2003/0166282 A1 | 9/2003 | Brown et al. | |
| 2003/0224432 A1 | 12/2003 | Myers et al. | |
| 2004/0038278 A1 | 2/2004 | Tzertzinis et al. | |
| 2004/0086884 A1 | 5/2004 | Beach et al. | |
| 2010/0028330 A1 | 2/2010 | Collins et al. | |
| 2010/0029498 A1 | 2/2010 | Gnirke et al. | |
| 2012/0039906 A1 | 2/2012 | Olive | |
| 2012/0114649 A1 | 5/2012 | Langermann et al. | |
| 2012/0208706 A1 | 8/2012 | Downing et al. | |
| 2013/0309254 A1 | 11/2013 | Samuels et al. | |
| 2014/0287937 A1 | 9/2014 | So et al. | |
| 2014/0296081 A1 | 10/2014 | Diehn et al. | |
| 2014/0336996 A1 | 11/2014 | Sun et al. | |
| 2016/0009805 A1 | 1/2016 | Kowanetz et al. | |
| 2017/0175197 A1 | 6/2017 | Gatalica et al. | |
| 2017/0275689 A1 | 9/2017 | Maguire et al. | |
| 2018/0045727 A1 | 2/2018 | Spetzler et al. | |
| 2018/0231554 A1 | 8/2018 | Schatton et al. | |
| 2018/0282417 A1 | 10/2018 | Higgs et al. | |
| 2018/0291074 A1 | 10/2018 | Chan et al. | |
| 2018/0363066 A1 | 12/2018 | Chalmers et al. | |
| 2018/0371099 A1 | 12/2018 | Bourgon et al. | |
| 2019/0025308 A1 | 1/2019 | Cummings et al. | |
| 2019/0085403 A1 | 3/2019 | Frampton et al. | |
| 2019/0218618 A1 | 7/2019 | Klijn et al. | |
| 2019/0219586 A1 | 7/2019 | Fabrizio et al. | |
| 2022/0056531 A1 | 2/2022 | Trabucco et al. | |
| 2022/0090205 A1 | 3/2022 | Klijn et al. | |
| 2022/0153861 A1 | 5/2022 | Bourgon et al. | |
| 2022/0412981 A1 | 12/2022 | Fabrizio et al. | |

FOREIGN PATENT DOCUMENTS

| | | |
|---|---|---|
| EP | 519596 A1 | 12/1992 |
| JP | 2016-520800 A | 7/2016 |
| JP | 2017-537087 A | 12/2017 |
| JP | 2018-502828 A | 2/2018 |
| JP | 2019-535237 A | 12/2019 |
| WO | WO-1986/001533 A1 | 3/1986 |
| WO | WO-1987/002671 A1 | 5/1987 |
| WO | WO-1988/009810 A1 | 12/1988 |
| WO | WO-1989/010134 A1 | 11/1989 |
| WO | WO-1990/002809 A1 | 3/1990 |
| WO | WO-1991/000906 A1 | 1/1991 |
| WO | WO-1991/010741 A1 | 7/1991 |
| WO | WO-1991/017271 A1 | 11/1991 |
| WO | WO-1992/001047 A1 | 1/1992 |
| WO | WO-1992/003917 A1 | 3/1992 |
| WO | WO-1992/003918 A1 | 3/1992 |
| WO | WO-1992/009690 A2 | 6/1992 |
| WO | WO-1992/015679 A1 | 9/1992 |
| WO | WO-1992/018619 A1 | 10/1992 |
| WO | WO-1992/020791 A1 | 11/1992 |
| WO | WO-1993/001288 A1 | 1/1993 |
| WO | WO-1994/016101 A2 | 7/1994 |
| WO | WO-1994/021822 A1 | 9/1994 |
| WO | WO-1996/029431 A2 | 9/1996 |
| WO | WO-2006/121168 A1 | 11/2006 |
| WO | WO-2007/005874 A2 | 1/2007 |
| WO | WO-2009/101611 A1 | 8/2009 |
| WO | WO-2009/114335 A2 | 9/2009 |
| WO | WO-2010/077634 A1 | 7/2010 |
| WO | WO-2012/092426 A1 | 7/2012 |
| WO | WO-2013/070634 A1 | 5/2013 |
| WO | WO-2014/151006 A2 | 9/2014 |
| WO | WO-2014/183078 A1 | 11/2014 |
| WO | WO-2015/095423 A2 | 6/2015 |
| WO | WO-2015/103037 A2 | 7/2015 |
| WO | WO-2015/116868 A2 | 8/2015 |
| WO | WO-2015/164862 A1 | 10/2015 |
| WO | WO-2016/018481 A2 | 2/2016 |
| WO | WO-2016/077553 A1 | 5/2016 |
| WO | WO-2016/081947 A2 | 5/2016 |
| WO | WO-2016/089873 A1 | 6/2016 |
| WO | WO-2017/151502 A1 | 9/2017 |
| WO | WO-2017/151517 A1 | 9/2017 |
| WO | WO-2017/151524 A1 | 9/2017 |
| WO | WO-2018/068028 A1 | 4/2018 |
| WO | WO-2019/018757 A1 | 1/2019 |

OTHER PUBLICATIONS

Albertson, "Localization of the ribosomal genes in Caenorhabditis elegans chromosomes by in situ hybridization using biotin-labeled probes," The EMBO Journal. 3(6): 1227-1234 (1984) (8 pages).

Andersen et al., "A conserved alternative splice in the von Recklinghausen neurofibromatosis (NF1) gene produces two neurofibromin isoforms, both of which have GTPase-activating protein activity," Molecular and Cellular Biology. 13(1): 487-495 (1993) (9 pages).

Anonymous: "Wayback Machine—Caris Life Sciences—Total Mutational Load (TML)",, Aug. 30, 2016 (Aug. 30, 2016), pp. 1-4, XP93031805, Retrieved from the Internet: URL:https://web.archive.org/web/20160830183217/http://www.carislifesciences.com:80/platforms/cmi-overview/total-mutational-load-tml/ [retrieved on Mar. 15, 2023].

Anonymous: "Wayback Machine—Foundation One", Sep. 27, 2016 (Sep. 27, 2016), pp. 1-29, XP93031809, Retrieved from the Internet: RL:https://web.archive.org/web/20160927005802/http://foundationone.com/learn.php#2 [retrieved on Mar. 15, 2023].

Ars, et al., "Mutations affecting mRNA splicing are the most common molecular defects in patients with neurofibromatosis type 1," Human Molecular Genetics. 9(2): 237-247 (2000) (11 pages).

Balch et al., "Final Version of 2009 AJCC Melanoma Staging and Classification," Journal of Clinical Oncology. 27(36): 6199-6206 (2009) (8 pages).

Baralle et al., "Different mutations in the NF1 gene are associated with Neurofibromatosis Noonan syndrome (NFNS)," Am J Med Genet. 119A(1):1-8 (2003).

Barbas et al., "Assembly of combinatorial antibody libraries on phage surfaces: the gene III site," PNAS. 88(18): 7978-7982 (1991) (5 pages).

Barringer et al., "Blunt-end and single-strand ligations by *Escherichia coli* ligase: influence on an in vitro amplification scheme," Gene. 89(1): 117-122 (1990) (6 pages).

Bartel et al., "Isolation of New Ribozymes from a Large Pool of Random Sequences," Science. 261(5127): 1411-1418 (1993) (8 pages).

Beidler et al., "Cloning and high level expression of a chimeric antibody with specificity for human carcinoembryonic antigen," The Journal of Immunology. 141(11): 4053-4060 (1988) (9 pages).

Ben-Salem et al., "The mutation spectrum of the NF1 gene in neurofibromatosis type I patients from UAE," Child's Nerv Syst. 30(7): 1183-1189 (2014) (7 pages).

Bernards et al., "Complete Human NF1 cDNA Sequence: Two Alternatively Spliced mRNAs and Absence of Expression in a Neuroblastoma Line," DNA and Cell Biology. 11(10): 727-734 (1992) (8 pages).

Bertola et al., "Neurofibromatosis-Noonan syndrome: Molecular evidence of the concurrence of both disorders in a patient," American Journal of Medical Genetics. 136A(3):242-245 (2005) (4 pages).

Bettegowda et al., "Detection of Circulating Tumor DNA in Early- and Late-Stage Human Malignancies," available in PMC May 12, 2014, published in final edited form as: Sci Transl Med. 6(224): 224ra24 (2014) (25 pages).

Better et al., "*Escherichia coli* Secretion of an Active Chimeric Antibody Fragment," Science. 240(4855): 1041-1043 (1988) (3 pages).

Billy et al., "Specific interference with gene expression induced by long, double-stranded RNA in mouse embryonal teratocarcinoma cell lines," PNAS. 98(25): 14428-14433 (2001) (6 pages).

(56) References Cited

OTHER PUBLICATIONS

Boulandet et al., "NF1 gene analysis focused on CpG-rich exons in a cohort of 93 patients with neurofibromatosis type 1," Human Mutation. 16(3): 274-275 (2000) (7 pages).
Breslow, "Thickness, cross-sectional areas and depth of invasion in the prognosis of cutaneous melanoma," Annals of Surgery. 172(5): 902-908 (1970) (7 pages).
Brüggemann et al., "Designer mice: the production of human antibody repertoires in transgenic animals," Year Immunol. 7:33-40 (1993) (8 pages).
Brüggemann et al., "Human antibody production in transgenic mice: expression from 100 kb of the human IgH locus," Eur J Immunol. 21(5): 1323-1326 (1991).
Butler et al., "Allpaths: De novo assembly of whole-genome shotgun microreads," Genome Research. 18(5):810-820 (2008) (11 pages).
Cancer Genome Atlas Network, "Genomic Classification of Cutaneous Melanoma," Cell. 161 (7):1681-1696 (2015) (17 pages).
Cancer Genome Atlas Research Network, "Comprehensive molecular characterization of urothelial bladder carcinoma," Nature. 507(7492):315-22 (2014) (8 pages).
Carell et al., "A Novel Procedure for the Synthesis of Libraries Containing Small Organic Molecules," Angew Chem Int Ed Engl. 33(20):2059-2061 (1994) (3 pages).
Carell et al., "A Solution-Phase Screening Procedure for the Isolation of Active Compounds from a Library of Molecules," Angew Chem Int Ed in Engl. 33(20):2061-2064 (1994) (4 pages).
Casey et al., "MYC regulates the antitumor immune response through CD47 and PD-L 1," Science. 352(6282):227-231 (Mar. 2016) (5 pages).
Cawthon et al., "A major segment of the neurofibromatosis type 1 gene: cDNA sequence, genomic structure, and point mutations," Cell. 62(1):193-201 (1990) (9 pages).
Chae et al., "Clinical Implications of Circulating Tumor DNA Tumor Mutational Burden (ctDNA TMB) in Non-Small Cell Lung Cancer," The Oncologist. 24(6):820-28. (2019).
Champiat et al., "Exomics and immunogenics: Bridging mutational load and immune checkpoints efficacy" OncoImmunology. 3(1):e27817 (2014) (6 pages).
Chen et al., "Effect of Combined Immune Checkpoint Inhibition vs Best Supportive Care Alone in Patients with Advanced Colorectal Cancer: The Canadian Cancer Trials Group CO.26 Study," JAMA Oncol. 6(6):831-838 (May 2020).
Cho et al., "An Unnatural Biopolymer," Science. 261(5126):1303-1305 (1993) (3 pages).
Clackson et al., "Making antibody fragments using phage display libraries," Nature. 352(6336):624-628 (1991) (5 pages).
Clemens et al., "Use of double-stranded RNA interference in *Drosophila* cell lines to dissect signal transduction pathways," PNAS. 97(12):6499-6503 (2000) (5 pages).
Cohen et al., Chapter 3: Emerging Technologies for Sequencing Antisense Oligonucleotides: Capillary Electrophoresis and Mass Spectrometry. Advances in Chromatography, vol. 36. Phyllis R. Brown and Eli Grushka, 127-162 (1995) (37 pages).
Cronin et al., "Measurement of Gene Expression in Archival Paraffin-Embedded Tissues: Development and Performance of a 92-Gene Reverse Transcriptase-Polymerase Chain Reaction Assay," Am J Pathol. 164(1): 35-42 (2004).
Cull et al., "Screening for receptor ligands using large libraries of peptides linked to the C terminus of the lac repressor," PNAS 89(5):1865-1869 (1992).
Cwirla et al., Peptides on phage: a vast library of peptides for identifying ligands, Proc Natl Acad Sci. 87(16):6378-6382 (1990).
Davis et al., "Comparison of tumor mutational burden (TMB) across tumor tissue and circulating tumor DNA (ctDNA)," J of Clin Oncol. 35(15 suppl): e23028-e23028 (May 30, 2017) (2 pages).
De Luca et al., "NF1 gene analysis based on DHPLC," Hum Mutat. 21(2):171-172 (2003) (8 pages).
De Luca et al., "NF1 Gene Mutations Represent the Major Molecular Event Underlying Neurofibromatosis-Noonan Syndrome," Am J Hum Genet. 77(6):1092-1101 (2005).
De Luca et al., "Novel and recurrent mutations in the NF1 gene in Italian patients with neurofibromatosis type 1," Hum Mutat. 23(6):629 (2004) (14 pages).
Devlin et al., "Random Peptide Libraries: a Source of Specific Protein Binding Molecules," Science. 249(4967):404-406 (1990).
Dewitt et al., "'Diversomers': an approach to nonpeptide, nonoligomeric chemical diversity," Proc Natl Acad Sci. 90(15):6909-6913 (1993).
Eisenhauer et al., "New response evaluation criteria in solid tumours: Revised RECIST guideline (version 1.1)," Eur J Cancer. 45(2):228-247 (2009).
Elbashir et al., "Duplexes of 21-nucleotide RNAs mediate RNA interference in cultured mammalian cells," Nature. 411(6836): 494-498 (2001).
Erb et al., "Recursive deconvolution of combinatorial chemical libraries," Proc Natl Acad Sci. 91(24):11422-11426 (1994).
Fahsold et al., "Minor lesion mutational spectrum of the entire NF1 gene does not explain its high mutability but points to a functional domain upstream of the GAP-related domain," Am J Hum Genet. 66(3):790-818 (2000).
Faria et al., "Phosphoramidate oligonucleotides as potent antisense molecules in cells and in vivo," Nat Biotechnol. 19:40-44 (2001).
Felici et al., "Selection of antibody ligands from a large library of oligopeptides expressed on a multivalent exposition vector," J Mol Biol. 222(2):301-310 (1991).
Ferner et al., "Neurofibromatous neuropathy in neurofibromatosis 1 (NF1)" J Med Genet. 41: 837-841 (2004).
Finger et al., "The human PD-1 gene: complete cDNA, genomic organization, and developmentally regulated expression in B cell progenitors" Gene. 197(1-2):177-87 (1997).
Fodor et al., "Multiplexed biochemical assays with biological chips," Nature. 364:555-556 (1993).
Forbes et al., "Cosmic: exploring the world's knowledge of somatic mutations in human cancer," Nucl Acids Res. 43(01):D805-D811 (2015).
Francisco et al., "Chapter 4: Melanoma Genetics: From Susceptibility to Progression" Melanoma—From Early Detection to Treatment. IntechOpen, 83-136 (Jan. 2013).
Fuchs et al., "Targeting Recombinant Antibodies to the Surface of *Escherichia coli*: Fusion to a Peptidoglycan Associated Lipoprotein." Bio/Technology. 9:1369-72 (1991).
Gallop et al., "Applications of Combinatorial Technologies to Drug Discovery. 1. Background and Peptide Combinatorial Libraries," J Med Chem. 37(9):1233-1251 (1994).
Garon et al., "Pembrolizumab for the Treatment of Non-Small-Cell Lung Cancer," N Engl J Med. 372(21): 2018-2028 (2015).
Garrard et al., "FAB Assembly and Enrichment in a Monovalent Phage Display System," Biotechnology (N Y). 9(12):1373-1377 (1991).
Gasparini et al., "Scanning the first part of the neurofibromatosis type 1 gene by RNA-SSCP: Identification of three novel mutations and of two new polymorphisms," Hum Genet. 97: 492-495 (1996).
Gautier et al., "Alpha-DNA. IV: Alpha-anomeric and beta-anomeric tetrathymidylates covalently linked to intercalating oxazolopyridocarbazole. Synthesis, physicochemical properties and poly (rA) binding," Nucl Acid Res. 15(16):6625-6641 (1987).
Gerlinger et al., "Ultra-deep T cell receptor sequencing reveals the complexity an intratumour heterogeneity of T cell clones in renal cell carcinomas," J Pathol. 231(4):424-432 (2013).
Ginzinger et al., "Measurement of DNA Copy Number at Microsatellite Loci Using Quantitative PCR Analysis," Cancer Res. 60(19):5405-5409 (2000) (6 pages).
Gnirke et al., "Solution hybrid selection with ultra-long oligonucleotides for massively parallel targeted sequencing," avaliable in PMC Aug. 1, 2009, published in final edited form as: Nat Biotechnol. 27(2):182-189 (2009) (24 pages).
Gram et al., "In vitro selection and affinity maturation of antibodies from a native combinatorial immunoglobulin library," Proc Natl Acad Sci. U S A 89(8):3576-3580 (1992).

(56) References Cited

OTHER PUBLICATIONS

Green et al., "Antigen-specific human monoclonal antibodies from mice engineered with human Ig heavy and light chain YACs," Nat Genet. 7(1):13-21 (1994).
Griffin et al., "DNA sequencing. Recent innovations and future trends," App Biochem Biotechnol. 38(1-2):147-159 (1993).
Griffiths et al., "Human anti-self antibodies with high specificity from phage display libraries," EMBO J. 12(2):725-734 (1993).
Guatelli et al., "Isothermal, in vitro amplification of nucleic acids by a multienzyme reaction modeled after retroviral replication," Proc Natl Acad Sci. 87(5):1874-1878 (1990).
Gubin et al., "Cancer. The odds of immunotherapy success," Science. 350(6257):158-9 (2015) (3 pages).
Gubin et al., "The odds of immunotherapy success," Science. 350(6257):158-9 (2015) (3 pages).
Hamid et al., "Safety and tumor responses with lambrolizumab (anti-PD-1) in melanoma," N Engl J Med. 369(2):134-144 (2013).
Han et al., "Evaluation of denaturing high performance liquid chromatography (DHPLC) for the mutational analysis of the neurofibromatosis type 1 (NF1) gene," Hum Genet. 109(5):487-497 (2001).
Hansen et al., "PD-L1 Testing in Cancer: Challenges in Companion Diagnostic Development," JAMA Oncology. 2(1):15-16 (Jan. 2016) (3 pages).
Haselhoff et. al., "Simple RNA enzymes with new and highly specific endoribonuclease activites," Nature. 334(6183):585-591 (1988) (6 pages).
Hawkins et al., "Selection of phage antibodies by binding affinity. Mimicking affinity maturation," J Mol Biol. 226(3):889-96 (1992).
Hay et al., "Bacteriophage cloing and *Escherichia coli* expression of a human IgM Fab," Hum Antibod Hybridomas. 3(2):81-85 (1992).
Helene et al., "Control of gene expression by triple helix-forming oligonucleotides. The antigene strategy," Annals of the New York Academy of Sciences. 660:27-36 (1992).
Helene et al., "The anti-gene strategy: control of gene expression by triplex-forming-oligonucleotides," Anti-cancer Drug Design. 6(6):569-584 (1991).
Herbst et al., "Predictive correlates of response to the anti-PD-L1 antibody MPDL3280A in cancer patients," Nature. 515(7528):563-7 (2014) (18 pages).
Hodis et al., "A Landscape of Driver Mutations in Melanoma," available in PMC Jul. 20, 2013, published in final edited form as: Cell. 150(2):251-263 (2012) (24 pages).
Hoogenboom et al., "Multi-subunit proteins on the surface of filamentous phage: methodologies for displaying antibody (Fab) heavy and light chains," Nucleic Acids Research, 19(15):4133-4137 (1991).
Houghten et al., "The use of synthetic peptide combinatorial libraries for the identification of bioactive peptides," Biotechniques. 13(3):412-21 (1992).
Hudson et al., "Novel and recurrent mutations in the neurofibromatosis type 1 (NF1) gene," Hum Mutat. 9(4):366-367 (1997).
Hugo et al., "Genomic and Transcriptomic Features of Response to Anti-PD-1 Therapy in Metastatic Melanoma," Cell. 165(1):35-44 (Mar. 2016) (14 pages).
Huse et al., "Generation of a large combinatorial library of the immunoglobulin repertoire in phage lambda," Science. 246(4935):1275-81 (1989) (5 pages).
Hyrup et al., "Genomic and Transcriptomic Features of Response to Anti-PD-1 Therapy in Metastatic Melanoma," available in PMC Mar. 24, 2017, published in final edited form as: Cell. 165(1):35-44 (1996) (21 pages).
Hyrup et al., "Peptide Nucleic Acids (PNA): Synthesis, properties and potential applications," Bioorganic & Medicinal Chemistry. 4(1):5-23 (1996).
Inoue et al., "Sequence-dependent hydrolysis of RNA using modified oligonucelotide splints and RNase H," FEBS Letters. 215(2):327-330 (1987).
Inoue et al., "Synthesis and hybridization studies on two complementary nona(2'-O-methyl)ribonucleotides," Nucleic Acid Research. 15(15):6131-6148 (1987).
Johnson et al., "Clinical Activity of Ipilimumab in Arcal Melanoma: A Retrospective Review," The Oncologist. 20(6):648-652 (2015).
Johnson et al., "Impact of NRAS Mutations for Patients with Advance Melanoma Treated with Immune Therapies," available in PMC Mar. 1, 2016, published in final edited form as: Cancer Immunol Res. 3(3):288-295 (2015) (17 pages).
Jones et al., "Replacing the complementarity-determining regions in a human antibody with those from a mouse," Nature. 321(6069):522-5 (1986).
Kallioniemi et al., "ERBB2 amplification in breast cancer analyzed by fluorescence in situ hybridization," PNAS. 89(12)5321-5325 (1992).
Kaufmann et al., "Spinal neurofibromatosis without cafe-au-lait macules in two families with null mutations of the NF1 gene," Am J Hum Genet . . . 69(6):1395-1400 (2001).
Kei A Sato et al., "Individualized Mutation Detection in Circulating Tumor DNA for Monitoring Colorectal Tumor Burden Using a Cancer-Associated Gene Sequencing Panel," PLoS One. Jan. 4, 2016;11(1): e0146275 .doi:10.1371/journal. pone .0146275 (15 pages).
Klose et al., "Selective Disactiviation of Neurofibromin GAP Activity in Neurofibromatosis Type 1 (NF1)," Human Molecular Genetics, 7(8): 1261-1268 (1998).
Kluwe et al., "Molecular study of frequency of mosaicism in neurofibromatosis 2 patients with bilateral vestibular schwannomas," J Med Genet, 40(2):109-114 (2003).
Kluwe et al., "NF1 mutations in neurofibromatosis 1 patients with plexiform neurofibromas," Human Mutation. 19(3):309 (2002) (5 pages).
Krauthammer et al., "Exome sequencing identifies recurrent mutations in NF1 and RASopathy genes in sun-exposed melanoma," available in PMC Jun. 22, 2016, published in final edited form as: Nat Genet. 47(9):996-1002 (2015) (25 pages).
Krauthammer et al., "Exome sequencing identifies recurrent somatic RAC1 mutations in melanoma," avaliable in PMC Mar. 1, 2013, published in final edited form as: Nat Genet. 44(9):1006-1014 (2012) (30 pages).
Krkljus et al., "Analysis of CpG C-to-T mutations in neurofibromatosis type 1," Human Mutation, 11(5):411 (11 pages) (1998).
Kwoh et al., "Transcription-based amplification system and detection of amplified human immunodeficiency virus type 1 with a bead-based sandwich hybridization format," Proc Natl Acad Sci U S A. 86(4):1173-7 (1989).
Lam et al., "A new type of synthetic peptide library for identifying ligand-binding activity," Nature. 354(6348):82-84 (1991).
Lam, "Application of combinatorial library methods in cancer research and drug discovery," Anticancer Drug Des. 12(3):145-67 (1997).
Landegren et al., "A ligase-mediated gene detection technique," Science. 241(4869):1077-80 (1988).
Larkin et al., "Combined Nivolumab and Ipilimumab or Monotherapy in Untreated Melanoma," available in PMC Nov. 22, 2017, published in final edited form as: N Engl J Med. 373(1):23-34 (2015) (18 pages).
Lemaitre et al., "Specific antiviral activity of a poly(L-lysine)-conjugated oligodeoxyribonucleotide sequence complementary to vesicular stomatitis virus N protein mRNA initiation site," PNAS. 84(3):648-652 (1987).
Letsinger et al., (1989). "Cholesteryl-conjugated oligonucleotides: synthesis, properties, and activity as inhibitors of replication of human immunodeficiency virus in cell culture," PNAS, 86(17):6553-6556.
Li et al., "Genomic organization of the neurofibromatosis 1 gene (NF1 )," Genomics. 25(1):9-18 (1995).
Li et al., "Somatic mutations in the neurofibromatosis 1 gene in human tumors," Cell. 69(2):275-281 (1992).
Liu et al., "Chimeric mouse-human IgG1 antibody that can mediate lysis of cancer cells," Proc Natl Acad Sci USA. 84(10):3439-43 (1987).

(56) References Cited

OTHER PUBLICATIONS

Liu et al., "Genomic Organization of a New Candidate Tumor Suppressor Gene, LRP1 B," Genomics. 69(2):271-274 (2000).
Liu et al., "LRP-DIT, a Putative Endocytic Receptor Gene, Is Frequently Inactivated in Non-Small Cell Lung Cancer Cell Lines," Cancer Research. 60(7):1961-1967 (2000) (9 pages).
Liu et al., "Production of a mouse-human chimeric monoclonal antibody to CD20 with potent Fc-dependent biologic activity," J Immunol. 139(10):3521-26 (1987).
Lonberg et al., "Antigen-specific human antibodies from mice comprising four distinct genetic modifications," Nature. 368(6474): 856-859 (1994).
Luke et al., "Clinical activity of ipilimumab for metastatic uveal melanoma: a retrospective review of the Dana-Farber Cancer Institute, Massachusetts General Hospital, Memorial Sloan-Kettering Cancer Center, and University Hospital of Lausanne experience," available in PMC Apr. 14, 2014, published in final edited form as: Cancer. 119(20):3687-3695 (2013) (17 pages).
Maher, L.J., "DNA triple-helix formation: an approach to artificial gene repressors?," Bioessays. 14( 12) :807-815 (1992).
Marchuk et al., "cDNA cloning of the type 1 neurofibromatosis gene: complete sequence of the NF1 gene product," Genomics. 11 (4): 931-940 (1991).
Martin et al., "The GAP-related domain of the neurofibromatosis type 1 gene product interacts with ras p21," Cell. 63(4):843-849 (1990).
Masuda et al., "Analysis of chemical modification of RNA from formalin-fixed samples and optimization of molecular biology applications for such samples," Nucleic Acids Research. 27(22):4436-4443 (1999).
Mattocks et al., "Automated comparative sequence analysis identifies mutations in 89% of NF1 patients and confirms a mutation cluster in exons 11-17 distinct from the GAP related domain," Journal of Medical Genetics. 41 (4):E48 (2004) (8 pages).
Maxam et al., "A new method for sequencing DNA," Proc Natl Acad Sci U.S.A. 74(2):560-4 (1977).
Maynard et al., "Characterization and significance of nine novel mutations in exon 16 of the neurofibromatosis type 1 (NF1) gene," Human Genetics. 99(5):674-6 (1997).
Messiaen et al., "Exon 10b of the NF1 gene represents a mutational hotspot and harbors a recurrent missense mutation Y489C associated with aberrant splicing," Genetics in Medicine. 1 (6):248-253 (1999).
Metzker, "Sequencing technologies—the next generation," Nature Reviews Genetics. 11 (1 ):31-46 (2010).
Morrison et al., "Chimeric human antibody molecules: Mouse antigen-binding domains with human constant region domains," Proc Natl Acad Sci U S A. 81(21):6851-5 (1984).
Morrison, "Transfectomas provide novel chimeric antibodies," Science. 229(4719):1202-7 (1985).
Naeve et al., "Accuracy of automated DNA sequencing: a multi-laboratory comparison of sequencing results," Biotechniques 19(3):448-53 (1995).
Nath et al., "Fluorescence in situ hybridization (FISH): DNA probe production and hybridization criteria," Biotechnic & Histochemistry. 73(1 ):6-22 (1998) (18 pages).
Nemethova et al., "Thirty-nine novel neurofibromatosis 1 (NF1) gene mutations identified in Slovak patients," Annals of Human Genetics. 77(5):364-379 (2013).
Nikolaev et al., "Exome sequencing identifies recurrent somatic MAP2K1 and MAP2K2 mutations in melanoma," Nature Genetics. 44(2):133-139 (2011) (9 pages).
Nishi et al., "Differential expression of two types of the neurofibromatosis type 1 (NF1) gene transcripts related to neuronal differentiation," Oncogene. 6(9):1555-1559 (1991).
Nishimura et al., "Recombinant human-mouse chimeric monoclonal antibody specific for common acute lymphocytic leukemia antigen," Cancer Research. 47(4):999-1005 (1987).
Nissan et al., "Loss of NF1 in Cutaneous Melanoma Is Associated with RAS Activation and MEK Dependence," available in PMC Apr. 15, 2015, published in final edited form as: Cancer Research. 74(8):2340-2350 (2014) (18 pages).
Nyström et al., "Noonan syndrome and neurofibromatosis type I in a family with a novel mutation in NF1 ," Clinical Genetics. 76(6):524-534 (2009).
Oi et al., "Chimeric Antibodies," BioTechniques. 4(3):214-221 (1986) (8 pages).
Paz-Ares, et al., "Pembrolizumab plus Chemotherapy for Squamous Non-Small-Cell Lung Cancer" The New England Journal of Medicine. 379:21 (2018) (12 pages).
Perry-O'Keefe et al., "Peptide nucleic acid pre-gel hybridization: an alternative to southern hybridization," PNAS. 93(25): 14670-14675 (1996) . . . .
Peters et al., "A novel mutation L 1425p in the GAP-region of the NF1 gene detected by temperature gradient gel electrophoresis (TGGE)," Human Mutation. 13(4):337 (1999) (5 pages).
Peters et al., "Atezolizumab versus chemotherapy in advanced or metastatic NSCLC with high blood-based tumor mutational burden: primary analysis of BFAST cohort C randomized phase 3 trial," Nat Med. 28(9):1831-1839 (2022) (23 pages).
Pinkel et al., "Fluorescence in situ hybridization with human chromosome-specific libraries: detection of trisomy 21 and translocations of chromosome 4," Proc Natl Acad Sci U S A. 85(23):9138-42 (1988).
Pinkel et al., "High resolution analysis of DNA copy number variation using comparative genomic hybridization to microarrays," Nature Genetics. 20(2):207-11 (1998).
Ponti et al., "Clinico-pathological and biomolecular findings in Italian patients with multiple cutaneous neurofibromas," Hereditary Cancer in Clinical Practive. 9(1):6 (2011) (9 pages).
Postow et al., "Ipilimumab for Patients With Advanced Mucosal Melanoma," The Oncologist. 18(6):726-32 (2013).
Purandare et al., "Characterisation of inherited and sporadic mutations in neurofibromatosis type-1," Hum Mol Genet. 3(7):1109-1115 (1994).
Redman et al., "Advances in immunotherapy for melanoma," BMC Medicine. 14(1):20 (Dec. 2016) (11 pages).
Rizvi et al., "Activity and safety of nivolumab, an anti-PD-1 immune checkpoint inhibitor, for patients with advanced, refractory squamous non-small-cell lung cancer (CheckMate 063): a phase 2, single-arm trial," available in PMC Dec. 12, 2017, published in final edited form as: Lancet Oncol. 16(3):257-65 (2015) (21 pages).
Robert et al., "Nivolumab in Previously Untreated Melanoma without BRAF Mutation," N Engl J Med. 372(4):320-30 (2015).
Robert et al., "Pembrolizumab versus Ipilimumab in Advanced Melanoma," N Engl J Med. 372(26):2521-32 (2015).
Sanger et al., "DNA sequencing with chain-terminating inhibitors," Proc Natl Acad Sci U.S.A. 74(12):5463-7 (1977).
Schrock et al., "Characterization of 298 Patients with Lung Cancer Harboring MET Exon 14 Skipping Alterations," J Thorac Oncol. 11(9):1493-502 (Sep. 2016).
Schumacher et al., "Biomarkers in Cancer Immunotherapy," Cancer Cell. 27(1):12-14 (2015).
Scott et al., "Searching for peptide ligands with an epitope library," Science. 249(4967):386-390 (1990).
Shaw et al., "Mouse/human chimeric antibodies to a tumor-associated antigen: biologic activity of the four human IgG subclasses," J Nat Canc Inst. 80(19):1553-1559 (1988).
Shen et al., "Neurofibromatosis type 1 (NF1 ): the search for mutations by PCR-heteroduplex analysis on Hydrolink gels," Hum Mol Genet. 2(11):1861-1864 (1993).
Shen et al., "ARID1A Deficiency Impairs the DNA Damage Checkpoint and Sensitizes Cells to PARP Inhibitors," Cancer Discov. 5(7):752-67 (2015) (17 pages).
Shen et al., "Molecular genetics of neurofibromatosis type 1 (NF1)," J Med Genet. 33(1):2-17 (1996).
Shinohara et al., "Structure and chromosomal localization of the human PD-1 gene (PDCD1 )," Genomics. 23(3):704-706 (1994).
Siolas et al., "Synthetic shRNAs as potent RNAi triggers," Nature Biotechnology. 23(2):227-31 (2005).
Sjöblom et al., "The Consensus Coding Sequences of Human Breast and Colorectal Cancers," Science. 314(5797): 268-74 (2006) (8 pages).

(56) References Cited

OTHER PUBLICATIONS

Smith et al., "Common fragile sites, extremely large genes, neural development and cancer," Cancer Lett. 232(1):48-57 (2006).
Snyder et al., "Genetic Basis for Clinical Response to CTLA-4 Blockade in Melanoma," N Engl J Med. 371(23):2189-2199 (2014).
Specht et al., "Quantitative Gene Expression Analysis in Microdissected Archival Formalin-Fixed and Paraffin-Embedded Tumor Tissue," AJP. 158(2):419-29 (2001).
Spranger et al., "Melanoma-intrinsic beta-catenin signaling prevents anti-tumour immunity," Nature. 523(7559): 231-235 (2015) (18 pages).
Sun et al., "Chimeric antibody with human constant regions and mouse variable regions directed against carcinoma-associated antigen 17-1A," Proc Natl Acad Sci USA. 84(1):214-8 (1987).
Suzuki et al., "Brain tumors predominantly express the neurofibromatosis type 1 gene transcripts containing the 63 base insert in the region coding for GTPase activating protein-related domain," Biochem Biophys Res Commun. 181(3): 955-961 (1991).
Suzuki et al., "Evidence for the Presence of Two Amino-Terminal Isoforms of Neurofibromin, a Gene Product Responsible for Neurofibromatosis Type 1," Tohoku J Exp Med. 175(4):225-33. (1995).
Suzuki et al., "Molecular cloning of a cDNA coding for neurofibromatosis type 1 protein isoform lacking the domain related to ras GTPase-activating protein," Biochem Biophys Res Commun. 187(2):984-990 (1992).
Tassabehji et al., "Tandem Duplication within a Neurofibromatosis Type I (NFI) Gene Exon in a Family with Features of Watson Syndrome and Noonan Syndrome," Am J Hum Genet. 53(1):90-5 (1993).
Thomas et al., "Exploring the somatic NF1 mutational spectrum associated with NF1 cutaneous neurofibromas," European Journal of Human Genetics. 20(4):411-9 (2012).
Topalian et al., "Safety, Activity, and Immune Correlates of Anti-PD-1 Antibody in Cancer," N Engl J Med. 366(26):2443-54 (2012).
Toulme, "New candidates for true antisense," Nat Biotechnol. 19(1):17-18 (2001).
Trapnell et al., "How to map billions of short reads onto genomes," available in PMC May 1, 2010, published in final edited form as: Nat Biotechnol. 27(5):455-7 (2009) (9 pages).
Tuaillon et al., "Human immunoglobulin heavy-chain minilocus recombination in transgenic mice: Gene-segment use in mu and gamma transcripts," Proc Natl Acad Sci USA. 90(8):3720-4 (1993).
Tumeh et al., "PD-1 blockade induces responses by inhibiting adaptive immune resistance," available in PMC May 26, 2015, published in final edited form as: Nature. 515(7528):568-571 (2014) (24 pages).
Upadhyaya et al., "An Absence of Cutaneous Neurofibromas Associated with a 3-bp Inframe Deletion in Exon 17 of the NF1 Gene (c.2970-2972 delAAT): Evidence of a Clinically Significant NF1 Genotype-Phenotype Correlation," Am J Hum Genet. 80(1):140-51 (2007).
Upadhyaya et al., "Analysis of mutations at the neurofibromatosis 1 (NF1) locus," Hum Mol Genet. 1(9): 735-740 (1992).
Upadhyaya et al., "Characterisation of germline mutations in the neurofibromatosis type 1 (NF1) gene," J Med Genet. 32(9):706-10 (1995).
Upadhyaya et al., "Molecular basis of neurofibromatosis type 1 (NF1): mutation analysis and polymorphisms in the NF1 gene," Hum Mutat. 4(2): 83-101 (1994).
Upadhyaya et al., "Mutational and functional analysis of the neurofibromatosis type 1 (NF1) gene," Hum Genet. 99(1):88-92 (1997).
Upadhyaya et al.; "Six novel mutations in the neurofibromatosis type 1 (NF1) gene," Human Mutation. 10(3):248-50 (1997).
Van der Krol et al., "Modulation of Eukaryotic Gene Expression by Complementary RNA or DNA Sequences," BioTechniques. 6(10):958-76 (1988).
Verhoeyen et al., "Reshaping Human Antibodies: Grafting an Antilysozyme Activity," Science. 239(4847):1534-6 (1988).

Wallace et al., "Type 1 neurofibromatosis gene: identification of a large transcript disrupted in three NF1 patients," Science. 249(4965): 181-186 (1990) (7 pages).
Wang et al., "Assessment of Blood Tumor Mutational Burden as a Potential Biomarker for Immunotherapy in Patients With Non-Small Cell Lung Cancer With Use of a Next-Generation Sequencing Cancer Gene Panel," Jama Oncology. 5(5):696-702 (2019).
Wang et al., "Neurofibromatosis type 1 gene as a mutational target in a mismatch repair-deficient cell type," Hum Genet. 112(2):117-123 (2003).
Warren et al., "Assembling millions of short DNA sequences using SSAKE," Bioinformatics 23(4): 500-1 (2007).
Weber et al., "Nivolumab versus chemotherapy in patients with advanced melanoma who progressed after anti-CTLA-4 treatment (CheckMate 037): a randomised, controlled, open-label, phase 3 trial," Lancet Oncol. 16(4):375-84 (2015) (10 pages).
Wheeless et al., "Bladder Irrigation Specimens Assayed by Fluorescence In Situ Hybridization to Interphase Nuclei," Cytometry. 17(4):319-26 (1994).
Wiesner et al., "NF1 Mutations are Common in Desmoplastic Melanoma," available in PMC Oct. 1, 2016, published in final edited form as: Am J Surg Pathol. 39(10):1357-62 (2015) (14 pages).
Wikipedia, "Exome," available online at <https://en.wikipedia.org/w/index.php?title=Exome&oldid=1010823778> (2021) (2 pages).
Wolchok, Jedd D., "PD-1 Blockers," Cell. 162(5):937 (2015) (1 page).
Wood et al., "The synthesis and in vivo assembly of functional antibodies in yeast," Nature. 314(6010): 446-449 (1985).
Woolf et al., "Specificity of antisense oligonucleotides in vivo," Proc Natl Acad Sci USA. 89(16):7305-9 (1992).
Wu et al., "Neurofibromatosis type I gene mutation in a patient with features of Leopard syndrome," Hum Mutat. 8(1): 51-56 (1996).
Wu et al., "The ligation amplification reaction (LAR)— amplification of specific DNA sequences using sequential rounds of template-dependent ligation," Genomics. 4(4):560-9 (1989).
Xu et al., "The neurofibromatosis type 1 gene encodes a protein related to GAP," Cell. 62(3): 599-608 (1990).
Yang et al., "Short RNA duplexes produced by hydrolysis with *Escherichia coli* RNase III mediate effective RNA interference in mammalian cells," PNAS. 99(15):9942-7 (2002).
Zatkova et al., "Disruption of Exonic Splicing Enhancer Elements Is the Principal Cause of Exon Skipping Associated With Seven Nonsense or Missense Alleles of NF1," Hum Mutat. 24(6):491-501 (2004).
Zerbino et al., "Velvet: Algorithms for de novo short read assembly using de Bruijn graphs," Genome Research. 18:821-829 (2008) (11 pages).
Zon, "Oligonucleotide analogues as potential chemotherapeutic agents," Pharm Res. 5(9): 539-549 (1988).
Zuckermann et al., "Discovery of Nanomolar Ligands for 7-Transmembrane G-Protein-Coupled Receptors from a Diverse N-(Substituted)glycine Peptoid Library," J Med Chem. 37(17):2678-2685 (1994).
Extended European Search Report for European Patent Application No. 22191450.0, dated Feb. 16, 2023 (7 pages).
"Exome," Wikipedia. Retrieved from <https://en.wikipedia.org/w/index.php?title=Exome&oldid=1010823778> on Jun. 17, 2021 (6 pages).
Asmar et al., "Clinical utility of nivolumab in the treatment of advanced melanoma," Ther Clin Risk Manag. 12:313-25 (2016).
Bahary et al., "Genomic profiling of circulating tumor DNA (ctDNA) from patients (pts) with pancreatic ductal adenocarcinoma (PDA)," J Clin Oncol. 35(15):4128 (2017) (Abstract Only) (5 pages).
Bardoli et al., "The PD-1/PD-L1 axis in the pathogenesis of urothelial bladder cancer and evaluating its potential as a therapeutic target," Future Oncol. 12(5):595-600 (2016).
Bidnur et al., "Inhibiting Immune Checkpoints for the Treatment of Bladder Cancer," Bladder Cancer. 2(1): 15-25 (2016) (11 pages).
Campesato et al., "Comprehensive cancer-gene panels can be used to estimate mutational load and predict clinical benefit to PD-1 blockade in clinical practice," Oncotarget. 6(33):34221-7 (2015) (7 pages).

(56) References Cited

OTHER PUBLICATIONS

Caris Life Sciences, "Total Mutational Load—Immune Checkpoint Inhibitors Response," <https://www.carismolecularintelligence.com/wp-content/uploads/2016/12/TN0291-v1_Total-Mutational-Load-Immunotherapy-REVERSED-PAGES.pdf>, dated Aug. 10, 2016, retrieved Jul. 13, 2021 (2 pages).

Castro et al., "Mismatch repair deficiency associate with complete remission to combination programmed cell death ligan immune therapy in a patient with sporadic urothelial carcinoma: immunotheranostic considerations," J Immuno Ther Cancer. 3:58 (2015) (6 pages).

Cazier et al., "Whole-genome sequencing of bladder cancers reveals somatic CDKN1A mutations and clinicopathological associations with mutation burden," Nat Commun. 5:3756 (2014) (13 pages).

Chalmers et al., "Analysis of 100,000 human cancer genomes reveals the landscape of tumor mutational burden," Genome Med. 9(1):34 (2017) (14 pages).

Champiat et al., "Exomics and immunogenics," OncoImmunology. 3(1):e27817 (2014).

Choudhury et al., "Low T-cell Receptor Diversity, High Somatic Mutation Burden, and High Neoantigen Load as Predictors of Clinical Outcome in Muscle-invasive Bladder Cancer," Eur Urol Focus. 2(4):445-452 (2015).

Dagogo-Jack et al., "Genomic profiling of circulating tumor DNA (ctDNA) from patients (pts) with advanced non-small cell lung cancer (NSCLC)," J Clin Oncol. 35(15 suppl):9025 (2017) (5 pages).

Diaz et al., "Liquid Biopsies: Genotyping Circulating Tumor DNA," J Clin Oncol. 32(6):579-586 (2014) (9 pages).

Fabbri et al., "Analysis of the chronic lymphocytic leukemia coding genome: role of NOTCH1 mutational activation," J Exp Med. 208(7):1389-401 (2011).

Fakhrejahani et al., "Immunotherapies for bladder cancer: a new hope," Curr Opin Urol. 25(6):586-596 (2015).

FoundationOne, "Technical Information and Test Overview," retrieved on Jan. 18, 2018 from <https://assets.contentful.com/vhribv12lmne/6YRrchSINOeSu48YwuesoY/caeec492925a7d569ce4e070866f709b/F1_-_Tech_Specs.pdf> (2 pages).

Frampton et al., "Assessment of tumor mutation burden from >60,000 clinical cancer patients using comprehensive genomic profiling," J Clin Oncol. 34(15 suppl):11558 (2016) (5 pages).

Frampton et al., "Development and validation of a clinical cancer genomic profiling test based on massively parallel DNA sequencing," available in PMC Dec. 1, 2017, published in final edited form as: Nat Biotechnol. 31(11): 1023-31 (2013) (25 pages).

Gabril et al., "Molecular Testing in Urothelial Tumors," Springer. 301-17 (2014).

Gandara et al., "Blood-based tumor mutational burden as a predictor of clinical benefit in non-small-cell lung cancer patients treated with atezolizumab," Nat Med. 24(9):1441-8 (2018) (8 pages).

Gatalica et al., "Programmed Cell Death 1 (PD-1) and Its Ligand (PD-L1) in Common Cancers and Their Correlation with Molecular Cancer Type," Cancer Epidemiol Biomarkers Prev. 23(12): 2965-2970 (2014).

Ghasemzadeh et al., "New Strategies in Bladder Cancer: A Second Coming for Immunotherapy," Clin Cancer Res. 22(4):793-801 (2015).

Govindan et al., "Genomic landscape of non-small cell lung cancer in smokers and never-smokers," Cell. 150(6):1121-34 and supplemental content (2012) (24 pages).

Gubin et al., "Checkpoint Blockade Cancer Immunotherapy Targets Tumour-Specific Mutant Antigens," Nature. 515(7528):577-81 (2014).

Gui et al., "Frequent mutations of chromatin remodeling genes in transitional cell carcinoma of the bladder," Nat Genet. 43(9):875-8 (2011).

Henick et al., "The PD-1 pathway as a therapeutic target to overcome immune escape mechanisms in cancer," Expert Opin Ther Targets. 18(12):1407-20 (2014) (14 pages).

Howitt et al., "Association of Polymerase e-Mutated and Microsatellite-Instable Endometrial Cancers With Neoantigen Load, Number of Tumor-Infiltrating Lymphocytes, and Expression of PD-1 and PD-L1," JAMA Oncol. 1(9):1319-23 (2015).

Jing et al., "PD-1/PD-L1 blockades in non-small-cell lung cancer therapy," Onco Targets Ther. 9:489-502 (2016).

Johnson et al., "Targeted Next Generation Sequencing Identifies Markers of Response to PD-1 Blockade," available in PMC Nov. 1, 2017, published in final edited form as: Cancer Immunol Res. 4(11):959-67 (2016) (17 pages).

Kates et al., "Immune checkpoint inhibitors: a new frontier in bladder cancer," World J Urol. 34(1):49-55 (2016) (7 pages).

Kim et al., "Emerging immunotherapies for bladder cancer," Curr Opin Oncol. 27(3):191-200 (2015).

Kim, "Immune checkpoint blockade therapy for bladder cancer treatment," Investig Clin Urol. 57 Suppl 1(Suppl 1):S98-S105 (2016).

Knowles et al., "Molecular biology of bladder cancer: new insights into pathogenesis and clinical diversity," Nat Rev Cancer. 15(1):25-41 (2015).

Kowanetz et al., "Tumor Mutation Burden (TMB) is Associated with Improved Efficacy of Atezolizumab in 1L and 2L+ NSCLC Patients," J Thorac Oncol. 12(1):S321-2 OA20.01 (Abstract) (2017).

Kurtoglu et al., "Elevating the Horizon: Emerging Molecular and Genomic Targets in the Treatment of Advanced Urothelial Carcinoma," Clin Genitourin Cancer. 13(5):410-20 (2015).

Le et al., "PD-1 Blockade in Tumors with Mismatch-Repair Deficiency," N Engl J Med. 372(26):2509-2520 (2015).

Llosa et al., "The Vigorous Immune Microenvironment of Microsatellite Instable Colon Cancer Is Balanced by Multiple Counter-Inhibitory Checkpoints," Cancer Discov. 5(1):43-51 (2015).

Maby et al., "Correlation between Density of CD8$^+$ T-cell Infiltrate in Microsatellite Unstable Colorectal Cancers and Frameshift Mutations: A Rationale for Personalized Immunotherapy," Cancer Res. 75(17):3446-55 (2015).

Marcq et al., "Targeting immune checkpoints: New opportunity for mesothelioma treatment?" Cancer Treat Rev. 41(10):914-24 (2015) (11 pages).

Melero et al., "Evolving synergistic combinations of targeted immunotherapies to combat cancer," Nat Rev Cancer. 15(8):457-72 (2015) (16 pages).

Meng et al., "Predictive biomarkers in PD-1/PD-L1 checkpoint blockade immunotherapy," Cancer Treat Rev. 41(10):868-76 (2015).

Millis et al., "Molecular Profiling of Infiltrating Urothelial Carcinoma of Bladder and Nonbladder Origin," Clin Genitourin Cancer. 13(1):e37-49 (2015).

Morse et al., "Elevated tumor mutational burden and prolonged clinical response to anti-PD-L1 antibody in platinum-resistant recurrent ovarian cancer," Gynecol Oncol Rep. 21:78-80 (2017).

Powles et al., "MPDL3280A (anti-PD-L1) treatment leads to clinical activity in metastatic bladder cancer," Nature. 515(7528): 558-62 (includes supplemental content) (2014) (12 pages).

Rizvi et al., "Cancer immunology. Mutational landscape determines sensitivity to PD-1 blockade in non-small cell lung cancer," Science. 348(6230):124-8 and supplementary materials (2015) (37 pages).

Rooney et al., "Molecular and Genetic Properties of Tumors Associated with Local Immune Cytolytic Activity," Cell. 160(1-2):48-61 (2015).

Rosenberg et al., "Atezolizumab in patients with locally advanced and metastatic urothelial carcinoma who have progressed following treatment with platinum-based chemotherapy: a single-arm, multicentre, phase 2 trial," Lancet. 387(10031):1909-20 and supplementary appendix (2016) (37 pages).

Rosenberg et al., "Supplement to: Atezolizumab in patients with locally advanced and metastatic urothelial carcinoma who have progressed following treatment with platinum-based chemotherapy: a single arm, phase 2 trial," Lancet. 387(10031):1909-20 (2016), accessed Apr. 8, 2020 (24 pages).

Schumacher et al., "Neoantigens in cancer immunotherapy," Science. 348(6230):69-74 (2015).

Stephens et al., "Analytic validation of a clinical circulating tumor DNA assay for patients with solid tumors," Ann Oncol. 27(Suppl. 6):vi401-vi406 (2016) (Abstract Only) (1 page).

(56) References Cited

OTHER PUBLICATIONS

Strickland et al., "Association and prognostic significance of BRCA1/2-mutation status with neoantigen load, number of tumor-infiltrating lymphocytes and expression of PD-1/PD-L1 in high grade serous ovarian cancer," Oncotarget. 7(12):13587-13598 (2016).
Tamborero et al., "OncodriveCLUST: exploiting the positional clustering of somatic mutations to identify cancer genes," Bioinformatics. 29(18):2238-44 (2013).
The Cancer Genome Atlas Research Network, "Comprehensive molecular characterization of urothelial bladder carcinoma," Nature. 507:315-22 (2014).
Vaish et al., "Microsatellite instability as prognostic marker in bladder tumors: a clinical significance," BMC Urol. 5:2 (2005) (7 pages).
Van Allen et al., "Genomic correlates of response to CTLA-4 blockade in metastatic melanoma," Science. 350(6257):207-211 (2015) (5 pages).
Van Buuren et al., "High sensitivity of cancer exome-based CD8 T cell neo-antigen identification," OncoImmunology. 3:e28836 (2014) (7 pages).
Vansteenkiste et al., "Prospects and progress of atezolizumab in non-small cell lung cancer," Expert Opin Biol Ther. 17(6):781-9 (2017) (10 pages).
Yamamoto et al., "Microsatellite instability: an update," Arch Toxicol. 89(6):899-921 (2015).
Yap et al., "Whole-Exome Sequencing of Muscle-Invasive Bladder Cancer Identifies Recurrent Mutations of UNC5C and Prognostic Importance of DNA Repair Gene Mutations on Survival," Clin Cancer Res. 20(24):6605-17 (2014).
Decision of Rejection for Japanese Patent Application No. 2018-545157, issued May 12, 2020 (10 pages).
Examination Report for Australian Patent Application No. 2017225854, dated Nov. 29, 2019 (3 pages).
First Office Action and Search Report for Chinese Application No. 201780024162.0, dated Sep. 25, 2020 (11 pages).
International Preliminary Report on Patentability for International Patent Application No. PCT/US2017/019682, issued Sep. 4, 2018 (8 pages).
International Preliminary Report on Patentability for International Patent Application No. PCT/US2017/019763, issued Sep. 4, 2018 (19 pages).
International Search Report and Written Opinion for International Patent Application No. PCT/US2017/019682, mailed Apr. 24, 2017 (17 pages).
International Search Report and Written Opinion for International Patent Application No. PCT/US2017/019763, mailed Aug. 2, 2017 (25 pages).
International Search Report and Written Opinion for International Patent Application No. PCT/US2017/055669, mailed Jan. 8, 2018 (21 pages).
International Search Report and Written Opinion for International Patent Application No. PCT/US2018/043074, mailed Oct. 29, 2018 (17 pages).
Notice of Preliminary Rejection for Korean Patent Application No. 10-2018-7027973, dated Oct. 16, 2019 (11 pages).
Notice of Preliminary Rejection for Korean Patent Application No. 10-2018-7027973, dated Oct. 26, 2020 (6 pages).
Notice of Preliminary Rejection for Korean Patent Application No. 10-2021-7032039, dated Jan. 17, 2022 (8 pages).
Notice of Reasons for Rejection for Japanese Patent Application No. 2018-545157, dated Sep. 24, 2019 (12 pages).
Office Action for Canadian Patent Application No. 3,015,528, dated Jul. 22, 2020 (4 pages).
Office Action for Canadian Patent Application No. 3,015,528, dated Jun. 27, 2019 (4 pages).
Second Office Action for Chinese Application No. 201780024162.0, dated Jan. 11, 2021 (9 pages).
Borch et al., "Reorienting the immune system in the treatment of cancer by using anti-PD-1 and anti-PD-L1 antibodies," Drug Discovery Today. 20(9):12 pages (2015).
Powles et al., "Immune biomarkers associated with clinical benefit from atezolizumab (MPDL3280a; anti-PD-L1) in advanced urothelial bladder cancer (UBC)," Journal for ImmunoTherapy of Cancer. 3(Suppl 2):P83 (2015).
Sherry et al., "dbSNP: the NCBI database of genetic variation," Nucleic Acids Research. 29(1): 308-311 (2001).
Shien et al., "Predictive biomarkers of response to PD-1/PD-L1 immune checkpoint inhibitors in non-small cell lung cancer," Lung Cancer. 99(1): 79-87 (Jun. 21, 2016).
Shukuya et al., "Predictive Markers for the Efficacy of Anti-PD-1/PD-L1 Antibodies in Lung Cancer," J. Thorac. Oncol. 11(7): 976-988 (Mar. 1, 2016).

\* cited by examiner

SEQUENCE LISTING

```
<160> NUMBER OF SEQ ID NOS: 33

<210> SEQ ID NO 1
<211> LENGTH: 440
<212> TYPE: PRT
<213> ORGANISM: Artificial Sequence
<220> FEATURE:
<223> OTHER INFORMATION: Synthetic Polypeptide

<400> SEQUENCE: 1

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205
```

-continued

Lys Arg Val Glu Ser Lys Tyr Gly Pro Pro Cys Pro Pro Cys Pro Ala
210                215                220

Pro Glu Phe Leu Gly Gly Pro Ser Val Phe Leu Phe Pro Pro Lys Pro
225                230                235                240

Lys Asp Thr Leu Met Ile Ser Arg Thr Pro Glu Val Thr Cys Val Val
            245                250                255

Val Asp Val Ser Gln Glu Asp Pro Glu Val Gln Phe Asn Trp Tyr Val
        260                265                270

Asp Gly Val Glu Val His Asn Ala Lys Thr Lys Pro Arg Glu Glu Gln
    275                280                285

Phe Asn Ser Thr Tyr Arg Val Val Ser Val Leu Thr Val Leu His Gln
290                295                300

Asp Trp Leu Asn Gly Lys Glu Tyr Lys Cys Lys Val Ser Asn Lys Gly
305                310                315                320

Leu Pro Ser Ser Ile Glu Lys Thr Ile Ser Lys Ala Lys Gly Gln Pro
            325                330                335

Arg Glu Pro Gln Val Tyr Thr Leu Pro Pro Ser Gln Glu Glu Met Thr
        340                345                350

Lys Asn Gln Val Ser Leu Thr Cys Leu Val Lys Gly Phe Tyr Pro Ser
    355                360                365

Asp Ile Ala Val Glu Trp Glu Ser Asn Gly Gln Pro Glu Asn Asn Tyr
370                375                380

Lys Thr Thr Pro Pro Val Leu Asp Ser Asp Gly Ser Phe Phe Leu Tyr
385                390                395                400

Ser Arg Leu Thr Val Asp Lys Ser Arg Trp Gln Glu Gly Asn Val Phe
            405                410                415

Ser Cys Ser Val Met His Glu Ala Leu His Asn His Tyr Thr Gln Lys
        420                425                430

Ser Leu Ser Leu Ser Leu Gly Lys
    435                440

<210> SEQ ID NO 2
<211> LENGTH: 214
<212> TYPE: PRT
<213> ORGANISM: Artificial Sequence
<220> FEATURE:
<223> OTHER INFORMATION: Synthetic Polypetide

<400> SEQUENCE: 2

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
            85                  90                  95

Thr Phe Gly Gln Gly Thr Lys Val Glu Ile Lys Arg Thr Val Ala Ala
        100                 105                 110

Pro Ser Val Phe Ile Phe Pro Pro Ser Asp Glu Gln Leu Lys Ser Gly
    115                 120                 125

```
Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 3
<211> LENGTH: 118
<212> TYPE: PRT
<213> ORGANISM: Artificial Sequence
<220> FEATURE:
<223> OTHER INFORMATION: Synthetic Polypeptide

<400> SEQUENCE: 3

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala
        115
```

<210> SEQ ID NO 4
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 4

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
```

```
                    85                  90                  95
Thr Phe Gly Gln Gly Thr Lys Val Glu Ile Lys Arg
                100                 105

<210> SEQ ID NO 5
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (6)..(6)
<223> OTHER INFORMATION: Xaa is Asp or Gly

<400> SEQUENCE: 5

Gly Phe Thr Phe Ser Xaa Ser Trp Ile His
1               5                   10

<210> SEQ ID NO 6
<211> LENGTH: 18
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (4)..(4)
<223> OTHER INFORMATION: Xaa is Ser or Leu
<220> FEATURE:
<221> NAME/KEY: MOD_RES
<222> LOCATION: (10)..(10)
<223> OTHER INFORMATION: Xaa is Thr or Ser

<400> SEQUENCE: 6

Ala Trp Ile Xaa Pro Tyr Gly Gly Ser Xaa Tyr Tyr Ala Asp Ser Val
1               5                   10                  15

Lys Gly

<210> SEQ ID NO 7
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 7

Arg His Trp Pro Gly Gly Phe Asp Tyr
1               5

<210> SEQ ID NO 8
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser
                20                  25

<210> SEQ ID NO 9
<211> LENGTH: 13
<212> TYPE: PRT
<213> ORGANISM: Artificial Sequence
```

```
<220> FEATURE:
<223> OTHER INFORMATION: Synthetic Polypeptide

<400> SEQUENCE: 9

Trp Val Arg Gln Ala Pro Gly Lys Gly Leu Glu Trp Val
1               5                   10

<210> SEQ ID NO 10
<211> LENGTH: 32
<212> TYPE: PRT
<213> ORGANISM: Artificial Sequence
<220> FEATURE:
<223> OTHER INFORMATION: Synthetic Polypeptide

<400> SEQUENCE: 10

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 11
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 11

Trp Gly Gln Gly Thr Leu Val Thr Val Ser Ala
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (5)..(5)
<223> OTHER INFORMATION: Xaa is Asp or Val
<220> FEATURE:
<221> NAME/KEY: MOD_RES
<222> LOCATION: (6)..(6)
<223> OTHER INFORMATION: Xaa is Val or Ile
<220> FEATURE:
<221> NAME/KEY: MOD_RES
<222> LOCATION: (7)..(7)
<223> OTHER INFORMATION: Xaa is Ser or Asn
<220> FEATURE:
<221> NAME/KEY: MOD_RES
<222> LOCATION: (9)..(9)
<223> OTHER INFORMATION: Xaa is Ala or Phe
<220> FEATURE:
<221> NAME/KEY: MOD_RES
<222> LOCATION: (10)..(10)
<223> OTHER INFORMATION: Xaa is Val or Leu

<400> SEQUENCE: 12

Arg Ala Ser Gln Xaa Xaa Xaa Thr Xaa Xaa Ala
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
```

```
<222> LOCATION: (4)..(4)
<223> OTHER INFORMATION: Xaa is Phe or Thr
<220> FEATURE:
<221> NAME/KEY: MOD_RES
<222> LOCATION: (6)..(6)
<223> OTHER INFORMATION: Xaa is Tyr or Ala

<400> SEQUENCE: 13

Ser Ala Ser Xaa Leu Xaa Ser
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (3)..(3)
<223> OTHER INFORMATION: Xaa is Tyr, Gly, Phe, or Ser
<220> FEATURE:
<221> NAME/KEY: MOD_RES
<222> LOCATION: (4)..(4)
<223> OTHER INFORMATION: Xaa is Leu, Tyr, Phe, or Trp
<220> FEATURE:
<221> NAME/KEY: MOD_RES
<222> LOCATION: (5)..(5)
<223> OTHER INFORMATION: Xaa is Tyr, Asn, Ala, Thr, Gly, Phe, or Ile
<220> FEATURE:
<221> NAME/KEY: MOD_RES
<222> LOCATION: (6)..(6)
<223> OTHER INFORMATION: Xaa is His, Val, Pro, Thr, or Ile
<220> FEATURE:
<221> NAME/KEY: MOD_RES
<222> LOCATION: (8)..(8)
<223> OTHER INFORMATION: Xaa is Ala, Trp, Arg, Pro, or Thr

<400> SEQUENCE: 14

Gln Gln Xaa Xaa Xaa Xaa Pro Xaa Thr
1               5

<210> SEQ ID NO 15
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 16
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 16

Trp Tyr Gln Gln Lys Pro Gly Lys Ala Pro Lys Leu Leu Ile Tyr
1               5                   10                  15

<210> SEQ ID NO 17
<211> LENGTH: 32
<212> TYPE: PRT
<213> ORGANISM: Artificial Sequence
```

```
<220> FEATURE:
<223> OTHER INFORMATION: Synthetic Polypeptide

<400> SEQUENCE: 17

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 18
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 18

Phe Gly Gln Gly Thr Lys Val Glu Ile Lys Arg
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 19

Gly Phe Thr Phe Ser Asp Ser Trp Ile His
1               5                   10

<210> SEQ ID NO 20
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 20

Ala Trp Ile Ser Pro Tyr Gly Gly Ser Thr Tyr Tyr Ala Asp Ser Val
1               5                   10                  15

Lys Gly

<210> SEQ ID NO 21
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 21

Arg His Trp Pro Gly Gly Phe Asp Tyr
1               5

<210> SEQ ID NO 22
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 22

Arg Ala Ser Gln Asp Val Ser Thr Ala Val Ala
1               5                   10
```

```
<210> SEQ ID NO 23
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 23

Ser Ala Ser Phe Leu Tyr Ser
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 24

Gln Gln Tyr Leu Tyr His Pro Ala Thr
1               5

<210> SEQ ID NO 25
<211> LENGTH: 118
<212> TYPE: PRT
<213> ORGANISM: Artificial Sequence
<220> FEATURE:
<223> OTHER INFORMATION: Synthetic Polypeptide

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
        115

<210> SEQ ID NO 26
<211> LENGTH: 122
<212> TYPE: PRT
<213> ORGANISM: Artificial Sequence
<220> FEATURE:
<223> OTHER INFORMATION: Synthetic Polypeptide

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
```

```
                    50                  55                  60
Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys
        115                 120

<210> SEQ ID NO 27
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 27

Trp Gly Gln Gly Thr Leu Val Thr Val Ser Ser
 1               5                  10

<210> SEQ ID NO 28
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 28

Phe Gly Gln Gly Thr Lys Val Glu Ile Lys
 1               5                  10

<210> SEQ ID NO 29
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 29

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser
             20                  25                  30

<210> SEQ ID NO 30
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 30

Trp Val Arg Gln Ala Pro Gly Lys Gly Leu Glu Trp Val Ala
 1               5                  10

<210> SEQ ID NO 31
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 31
```

```
Trp Gly Gln Gly Thr Leu Val Thr Val Ser Ser Ala Ser Thr Lys
1               5                   10                  15
```

<210> SEQ ID NO 32
<211> LENGTH: 447
<212> TYPE: PRT
<213> ORGANISM: Artificial Sequence
<220> FEATURE:
<223> OTHER INFORMATION: Synthetic Polypeptide

<400> SEQUENCE: 32

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350
```

```
Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly
                435                 440                 445

<210> SEQ ID NO 33
<211> LENGTH: 214
<212> TYPE: PRT
<213> ORGANISM: Artificial Sequence
<220> FEATURE:
<223> OTHER INFORMATION: Synthetic Polypeptide

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

THERAPEUTIC AND DIAGNOSTIC METHODS FOR CANCER

SEQUENCE LISTING

The instant application contains a Sequence Listing which has been submitted electronically in ASCII format and is hereby incorporated by reference in its entirety. Said ASCII copy, created on Jan. 31, 2022, is named 50474-131004_Sequence_Listing_1_31_22_ST25 and is 23,715 bytes in size.

FIELD OF THE INVENTION

Provided herein are therapeutic and diagnostic methods and compositions for pathological conditions, such as cancer (e.g., bladder cancer (e.g., urothelial bladder cancer)), and methods of using PD-L1 axis binding antagonists. In particular, the invention provides methods for patient selection and diagnosis, methods of treatment, articles of manufacture, diagnostic kits, and methods of detection.

BACKGROUND

Cancer remains one of the most deadly threats to human health. Cancers, or malignant tumors, metastasize and grow rapidly in an uncontrolled manner, making timely detection and treatment extremely difficult. In the U.S., cancer affects nearly 1.3 million new patients each year, and is the second leading cause of death after heart disease, accounting for approximately 1 in 4 deaths. Solid tumors are responsible for most of those deaths. Bladder cancer is the fifth-most common malignancy worldwide, with close to 400,000 newly diagnosed cases and approximately 150,000 associated deaths reported per year. In particular, metastatic urothelial bladder cancer is associated with poor outcomes and represents a major unmet medical need with few effective therapies to date.

Programmed death-ligand 1 (PD-L1) is a protein that has been implicated in the suppression of immune system responses during chronic infections, pregnancy, tissue allografts, autoimmune diseases, and cancer. PD-L1 regulates the immune response by binding to an inhibitory receptor, known as programmed death 1 (PD-1), which is expressed on the surface of T-cells, B-cells, and monocytes. PD-L1 negatively regulates T-cell function also through interaction with another receptor, B7-1. Formation of the PD-L1/PD-1 and PD-L1/B7-1 complexes negatively regulates T-cell receptor signaling, resulting in the subsequent downregulation of T-cell activation and suppression of anti-tumor immune activity.

Despite the significant advancement in the treatment of cancer (e.g., bladder cancer (e.g., urothelial bladder cancer)), improved therapies and diagnostic methods are still being sought.

SUMMARY OF THE INVENTION

The present invention provides therapeutic and diagnostic methods and compositions for cancer, for example, bladder cancer (e.g., urothelial bladder cancer, UBC).

In a first aspect, the invention features a method of treating a patient suffering from a bladder cancer, the method comprising administering to the patient a therapeutically effective amount of a PD-L1 axis binding antagonist, wherein a tumor sample obtained from the patient has been determined to have an increased level of somatic mutation in at least one gene set forth in Table 1 relative to a reference level of somatic mutation in the at least one gene set forth in Table 1. In some embodiments, the tumor sample obtained from the patient has been determined to have increased levels of somatic mutations in at least one-third of the genes set forth in Table 1 relative to reference levels of somatic mutations in the at least one-third of the genes set forth in Table 1. In some embodiments, the tumor sample obtained from the patient has been determined to have increased levels of somatic mutations in at least one-half of the genes set forth in Table 1 relative to reference levels of somatic mutations in the at least one-half of the genes set forth in Table 1. In some embodiments, the tumor sample obtained from the patient has been determined to have increased levels of somatic mutations in at least two-thirds of the genes set forth in Table 1 relative to reference levels of somatic mutations in the at least two-thirds of the genes set forth in Table 1. In some embodiments, the tumor sample obtained from the patient has been determined to have increased levels of somatic mutations in at least three-fourths of the genes set forth in Table 1 relative to reference levels of somatic mutations in the at least three-fourths of the genes set forth in Table 1. In some embodiments, the tumor sample obtained from the patient has been determined to have increased levels of somatic mutations in the genes set forth in Table 1 relative to reference levels of somatic mutations in the genes set forth in Table 1. In other embodiments, the somatic mutations are substitutions, deletions, and/or insertions. In some embodiments, the substitutions, deletions, and/or insertions are in coding regions. In some embodiments, the deletions and/or insertions are indels. In yet other embodiments, the tumor sample obtained from the patient has a whole-genome mutation load that is higher than a reference level whole-genome mutation load. In some embodiments, the median whole-genome mutation load is at least about 10 mutations per megabase (Mb).

In a second aspect, the invention features a method for determining whether a patient suffering from a bladder cancer is likely to respond to treatment comprising a PD-L1 axis binding antagonist, the method comprising determining the level of somatic mutation in at least one gene set forth in Table 1 from a tumor sample obtained from the patient, and comparing the level of somatic mutation in the at least one gene set forth in Table 1 to a reference level of somatic mutation in the at least one gene set forth in Table 1, wherein an increased level of somatic mutation in the at least one gene set forth in Table 1 relative to the reference level indicates that the patient is likely to respond to treatment comprising a PD-L1 axis binding antagonist.

In a third aspect, the invention features a method for predicting responsiveness of a patient suffering from a bladder cancer to treatment comprising a PD-L1 axis binding antagonist, the method comprising determining the level of somatic mutation in at least one gene set forth in Table 1 from a tumor sample obtained from the patient, and comparing the level of somatic mutation in the at least one gene set forth in Table 1 to a reference level of somatic mutation in the at least one gene set forth in Table 1, wherein an increased level of somatic mutation in the at least one gene set forth in Table 1 relative to the reference level indicates that the patient is likely to respond to treatment comprising a PD-L1 axis binding antagonist.

In a fourth aspect, the invention features a method for selecting a therapy for a patient suffering from a bladder cancer, the method comprising determining the level of somatic mutation in at least one gene set forth in Table 1 from a tumor sample obtained from the patient, and selecting a therapy comprising a PD-L1 axis binding antagonist for the patient based on an increased level of somatic mutation in the at least one gene set forth in Table 1 relative to the reference level of somatic mutation in the at least one gene set forth in Table 1.

In some embodiments of the second, third, and fourth aspects, the method further comprises administering to the patient a therapeutically effective amount of a PD-L1 axis binding antagonist based on the increased level of somatic mutation in at least one gene set forth in Table 1 relative to a reference level of somatic mutation in the at least one gene set forth in Table 1 in the tumor sample.

In some embodiments of any one of the preceding aspects, the PD-L1 axis binding antagonist is selected from the group consisting of a PD-L1 binding antagonist, a PD-1 binding antagonist, and a PD-L2 binding antagonist. In some embodiments, the PD-L1 axis binding antagonist is a PD-L1 binding antagonist. In some embodiments, the PD-L1 binding antagonist inhibits the binding of PD-L1 to one or more of its ligand binding partners. In some embodiments, the PD-L1 binding antagonist inhibits the binding of PD-L1 to PD-1. In some embodiments, the PD-L1 binding antagonist inhibits the binding of PD-L1 to B7-1. In other embodiments, the PD-L1 binding antagonist inhibits the binding of PD-L1 to both PD-1 and B7-1. In yet another embodiment the PD-L1 binding antagonist is an antibody. In some embodiments, for example, the antibody is selected from the group consisting of atezolizumab (MPDL3280A), YW243.55.S70, MDX-1105, MEDI4736 (durvalumab), and MSB0010718C (avelumab). In some embodiments, the antibody comprises a heavy chain comprising HVR-H1 sequence of SEQ ID NO:19, HVR-H2 sequence of SEQ ID NO:20, and HVR-H3 sequence of SEQ ID NO:21, and a light chain comprising HVR-L1 sequence of SEQ ID NO:22, HVR-L2 sequence of SEQ ID NO:23, and HVR-L3 sequence of SEQ ID NO:24. In some embodiments, the antibody comprises a heavy chain variable region comprising the amino acid sequence of SEQ ID NO:26 and a light chain variable region comprising the amino acid sequence of SEQ ID NO:4. In other embodiments, the PD-L1 axis binding antagonist is a PD-1 binding antagonist. In some embodiments, the PD-1 binding antagonist inhibits the binding of PD-1 to one or more of its ligand binding partners. In some embodiments, the PD-1 binding antagonist inhibits the binding of PD-1 to PD-L1. In yet other embodiments, the PD-1 binding antagonist inhibits the binding of PD-1 to PD-L2. In some embodiments, the PD-1 binding antagonist inhibits the binding of PD-1 to both PD-L1 and PD-L2. In other embodiments, the PD-1 binding antagonist is an antibody. In some embodiments, for example, the antibody is selected from the group consisting of, MDX-1106 (nivolumab), MK-3475 (pembrolizumab), CT-011 (pidilizumab), MEDI-0680 (AMP-514), PDR001, REGN2810, and BGB-108. In yet another embodiment, the PD-1 binding antagonist is an Fc-fusion protein. In some embodiments, the Fc-fusion protein is AMP-224. In other embodiments, the method further comprises administering to the patient an effective amount of a second therapeutic agent. In some embodiments, the second therapeutic agent is selected from the group consisting of a cytotoxic agent, a growth-inhibitory agent, a radiation therapy agent, an anti-angiogenic agent, and combinations thereof. In yet other embodiments, the bladder cancer is an urothelial bladder cancer (UBC). In some embodiments, the UBC is a metastatic UBC. In other embodiments, the UBC is a locally advanced UBC. In some embodiments, the patient has progressed following treatment with a platinum-based chemotherapeutic agent (i.e., the patient's disease (e.g., UBC, e.g., locally advanced or metastatic UBC) has progressed after prior treatment with a platinum-based chemotherapeutic agent for UBC, e.g., locally advanced or metastatic UBC). In some embodiments, the patient is ineligible for treatment with a platinum-based chemotherapeutic agent (e.g., a cisplatin-based chemotherapy) and has not received prior treatment, e.g., prior treatment for locally advanced or metastatic UBC. In other embodiments, the tumor sample is a formalin-fixed and paraffin-embedded (FFPE) tumor sample, an archival tumor sample, a fresh tumor sample, or a frozen tumor sample.

BRIEF DESCRIPTION OF THE DRAWINGS

FIG. 1B represents a statistical analysis of Cohort 2 patient data performed later than the statistical analysis shown in FIG. 1A and incorporates the "not estimable" (NE) patient subgroup in the Cohort 2 non-responder group. The graph shows a comparison between mutation load and response (CR/PR compared to SD/PD/NE) using a Wilcoxon rank sum test due to granularity of values and skew (left panel) and median mutation load per Mb by objective response status (right panel).

DETAILED DESCRIPTION OF THE INVENTION

I. Introduction

Figure 1A:
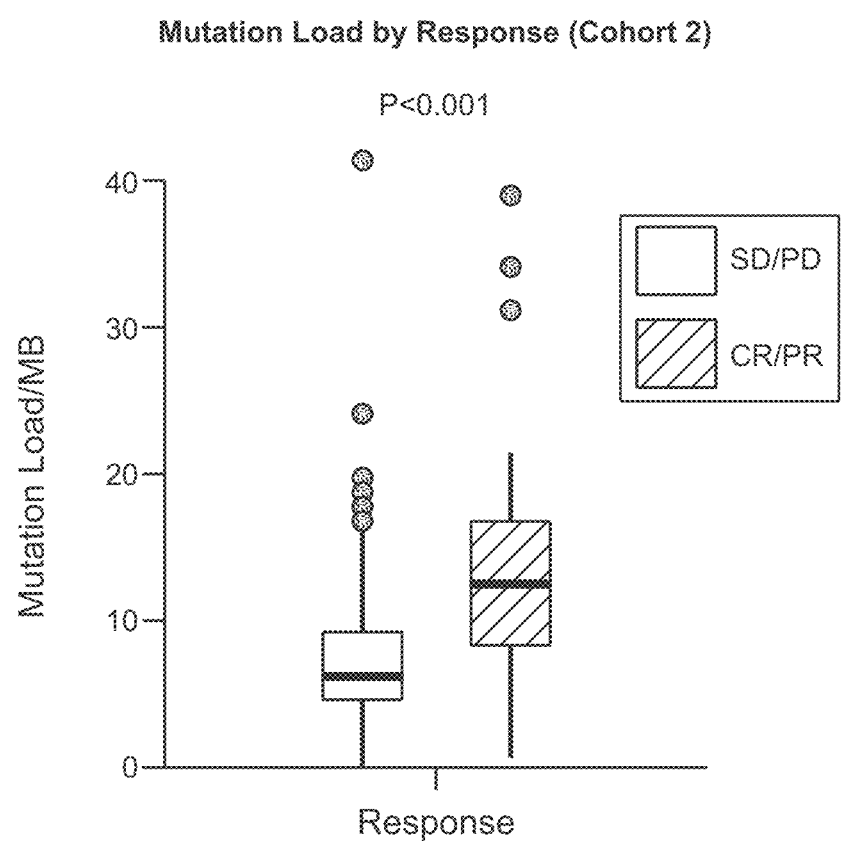
FIG. 1A is a graph showing that the median mutation load per Mb was significantly increased in Cohort 2 responders (12.4/Mb) compared to Cohort 2 non-responders (6.4/Mb) ($p<0.001$) using bimodal response criteria. The graph shows a comparison between mutation load and response (complete response/partial response (CR/PR) compared to stable disease/progressive disease (SD/PD)) using a Wilcoxon rank sum test due to granularity of values and skew.

The present invention provides therapeutic and diagnostic methods and compositions for cancer, for example, bladder cancer (e.g., urothelial bladder cancer, UBC). The invention is based, at least in part, on the discovery that determination of elevated levels of somatic mutations (e.g., mutation in genes listed in Table 1), in samples (e.g., tumor samples) obtained from a patient is useful in the treatment of a patient suffering from cancer, for diagnosing a patient suffering from cancer, for determining whether a patient having a cancer is likely to respond to treatment with an anti-cancer therapy that includes a PD-L1 axis binding antagonist (e.g., an anti-PD-L1 antibody, e.g., atezolizumab (MPDL3280A)), for optimizing therapeutic efficacy of an anti-cancer therapy that includes a PD-L1 axis binding antagonist (e.g., an anti-PD-L1 antibody, e.g., atezolizumab), and/or for patient selection for an anti-cancer therapy comprising a PD-L1 axis binding antagonist (e.g., an anti-PD-L1 antibody, e.g., atezolizumab).

II. Definitions

It is to be understood that aspects and embodiments of the invention described herein include "comprising," "consisting," and "consisting essentially of" aspects and embodiments. As used herein, the singular form "a," "an," and "the" includes plural references unless indicated otherwise.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X."

As used herein, the terms "mutational load," "mutation load," "mutational burden," or "tumor mutational burden," each of which may be used interchangeably, refer to the level (e.g., number) of an alteration (e.g., one or more alterations, e.g., one or more somatic alterations) per a pre-selected unit (e.g., per megabase) in a pre-determined set of genes (e.g., in the coding regions of the pre-determined set of genes). Mutation load can be measured, for example, on a whole genome or exome basis, or on the basis of a subset of the genome or exome. In certain embodiments, the mutation load measured on the basis of a subset of the genome or exome can be extrapolated to determine a whole genome or exome mutation load. In some embodiments, mutation load refers to the level of accumulated somatic mutations within an individual (e.g., an animal (e.g., a human)). The mutation load may refer to accumulated somatic mutations in a patient with cancer (e.g., bladder cancer (e.g., urothelial bladder cancer (UBC)). In some embodiments, mutation load refers to the accumulated mutations in the whole genome of an individual. In some embodiments, mutation load refers to the accumulated mutations within a particular sample (e.g., tissue sample, biopsy) collected from an individual. In some embodiments, mutation load refers to the accumulated mutations in a patient sample (e.g., tumor sample (e.g., bladder cancer tumor sample)).

The term "somatic mutation" or "somatic alteration" refers to a genetic alteration occurring in the somatic tissues (e.g., cells outside the germline). Examples of genetic alterations include, but are not limited to, point mutations (e.g., the exchange of a single nucleotide for another (e.g., silent mutations, missense mutations, and nonsense mutations)), insertions and deletions (e.g., the addition and/or removal of one or more nucleotides (e.g., indels)), amplifications, gene duplications, copy number alterations (CNAs), rearrangements, and splice variants. The presence of particular mutations can be associated with disease states (e.g., cancer (e.g., bladder cancer (e.g., urothelial bladder cancer, UBC))).

In certain embodiments, the somatic alteration is a silent mutation (e.g., a synonymous alteration). In other embodiments, the somatic alteration is a non-synonymous single nucleotide variant (SNV). In other embodiments, the somatic alteration is a passenger mutation (e.g., an alteration that has no detectable effect on the fitness of a clone). In certain embodiments, the somatic alteration is a variant of unknown significance (VUS), for example, an alteration, the pathogenicity of which can neither be confirmed nor ruled out. In certain embodiments, the somatic alteration has not been identified as being associated with a cancer phenotype.

In certain embodiments, the somatic alteration is not associated with, or is not known to be associated with, an effect on cell division, growth, or survival. In other embodiments, the somatic alteration is associated with an effect on cell division, growth, or survival.

In certain embodiments, the number of somatic alterations excludes a functional alteration in a sub-genomic interval.

In some embodiments, the functional alteration is an alteration that, compared with a reference sequence (e.g., a wild-type or unmutated sequence) has an effect on cell division, growth, or survival (e.g., promotes cell division, growth, or survival). In certain embodiments, the functional alteration is identified as such by inclusion in a database of functional alterations, e.g., the COSMIC database (see Forbes et al. *Nucl. Acids Res.* 43 (D1): D805-D811, 2015, which is herein incorporated by reference in its entirety). In other embodiments, the functional alteration is an alteration with known functional status (e.g., occurring as a known somatic alteration in the COSMIC database). In certain embodiments, the functional alteration is an alteration with a likely functional status (e.g., a truncation in a tumor suppressor gene). In certain embodiments, the functional alteration is a driver mutation (e.g., an alteration that gives a selective advantage to a clone in its microenvironment, e.g., by increasing cell survival or reproduction). In other embodiments, the functional alteration is an alteration capable of causing clonal expansions. In certain embodiments, the functional alteration is an alteration capable of causing one, two, three, four, five, or all six of the following: (a) self-sufficiency in a growth signal; (b) decreased, e.g., insensitivity, to an antigrowth signal; (c) decreased apoptosis; (d) increased replicative potential; (e) sustained angiogenesis; or (f) tissue invasion or metastasis.

In certain embodiments, the functional alteration is not a passenger mutation (e.g., is not an alteration that has no detectable effect on the fitness of a clone of cells). In certain embodiments, the functional alteration is not a variant of unknown significance (VUS) (e.g., is not an alteration, the pathogenicity of which can neither be confirmed nor ruled out).

In certain embodiments, a plurality (e.g., about 10%, 20%, 30%, 40%, 50%, 60%, 70%, 80%, 90%, or more) of functional alterations in a pre-selected tumor gene in the pre-determined set of genes are excluded. In certain embodiments, all functional alterations in a pre-selected gene (e.g., tumor gene) in the pre-determined set of genes are excluded. In certain embodiments, a plurality of functional alterations in a plurality of pre-selected genes (e.g., tumor genes) in the pre-determined set of genes are excluded. In certain embodiments, all functional alterations in all genes (e.g., tumor genes) in the pre-determined set of genes are excluded.

In certain embodiments, the number of somatic alterations excludes a germline mutation in a sub-genomic interval.

In certain embodiments, the germline alteration is an SNP, a base substitution, an insertion, a deletion, an indel, or a silent mutation (e.g., synonymous mutation).

In certain embodiments, the germline alteration is excluded by use of a method that does not use a comparison with a matched normal sequence. In other embodiments, the germline alteration is excluded by a method comprising the use of an algorithm. In certain embodiments, the germline alteration is identified as such by inclusion in a database of germline alterations, for example, the dbSNP database (see Sherry et al. *Nucleic Acids Res.* 29(1): 308-311, 2001, which is herein incorporated by reference in its entirety). In other embodiments, the germline alteration is identified as such by inclusion in two or more counts of the ExAC database (see Exome Aggregation Consortium et al. bioRxiv preprint, Oct. 30, 2015, which is herein incorporated by reference in its entirety). In some embodiments, the germline alteration is identified as such by inclusion in the 1000 Genome Project database (McVean et al. *Nature* 491, 56-65, 2012, which is herein incorporated by reference in its entirety). In some embodiments, the germline alteration is identified as such by inclusion in the ESP database (Exome Variant Server, NHLBI GO Exome Sequencing Project (ESP), Seattle, WA).

The term "PD-L1 axis binding antagonist" refers to a molecule that inhibits the interaction of a PD-L1 axis binding partner with one or more of its binding partners, so as to remove T-cell dysfunction resulting from signaling on the PD-1 signaling axis, with a result being restored or enhanced T-cell function. As used herein, a PD-L1 axis binding antagonist includes a PD-L1 binding antagonist and a PD-1 binding antagonist as well as molecules that interfere with the interaction between PD-L1 and PD-1 (e.g., a PD-L2-Fc fusion).

The term "dysfunction," in the context of immune dysfunction, refers to a state of reduced immune responsiveness to antigenic stimulation. The term includes the common elements of both "exhaustion" and/or "anergy" in which antigen recognition may occur, but the ensuing immune response is ineffective to control infection or tumor growth. The term "dysfunctional," as used herein, also includes refractory or unresponsive to antigen recognition, specifically, impaired capacity to translate antigen recognition into down-stream T-cell effector functions, such as proliferation, cytokine production (e.g., IL-2) and/or target cell killing.

The term "anergy" refers to the state of unresponsiveness to antigen stimulation resulting from incomplete or insufficient signals delivered through the T-cell receptor (e.g., increase in intracellular $Ca^{2+}$ in the absence of Ras activation). T-cell anergy can also result upon stimulation with antigen in the absence of co-stimulation, resulting in the cell becoming refractory to subsequent activation by the antigen even in the context of co-stimulation. The unresponsive state can often be overridden by the presence of interleukin-2. Anergic T-cells do not undergo clonal expansion and/or acquire effector functions.

The term "exhaustion" refers to T-cell exhaustion as a state of T-cell dysfunction that arises from sustained TCR signaling that occurs during many chronic infections and cancer. It is distinguished from anergy in that it arises not through incomplete or deficient signaling, but from sustained signaling. It is defined by poor effector function, sustained expression of inhibitory receptors and a transcriptional state distinct from that of functional effector or memory T-cells. Exhaustion prevents optimal control of infection and tumors. Exhaustion can result from both extrinsic negative regulatory pathways (e.g., immunoregulatory cytokines) as well as cell-intrinsic negative regulatory (co-stimulatory) pathways (PD-1, B7-H3, B7-H4, etc.).

"Enhancing T-cell function" means to induce, cause or stimulate a T-cell to have a sustained or amplified biological function, or renew or reactivate exhausted or inactive T-cells. Examples of enhancing T-cell function include: increased secretion of γ-interferon from CD8+ T-cells, increased proliferation, increased antigen responsiveness (e.g., viral, pathogen, or tumor clearance) relative to such levels before the intervention. In one embodiment, the level of enhancement is at least 50%, alternatively 60%, 70%, 80%, 90%, 100%, 120%, 150%, or 200% enhancement. The manner of measuring this enhancement is known to one of ordinary skill in the art.

"Tumor immunity" refers to the process in which tumors evade immune recognition and clearance. Thus, as a therapeutic concept, tumor immunity is "treated" when such evasion is attenuated, and the tumors are recognized and attacked by the immune system. Examples of tumor recognition include tumor binding, tumor shrinkage and tumor clearance.

"Immunogenicity" refers to the ability of a particular substance to provoke an immune response. Tumors are immunogenic and enhancing tumor immunogenicity aids in the clearance of the tumor cells by the immune response. Examples of enhancing tumor immunogenicity include treatment with a PD-L1 axis binding antagonist.

As used herein, a "PD-L1 binding antagonist" is a molecule that decreases, blocks, inhibits, abrogates or interferes with signal transduction resulting from the interaction of PD-L1 with either one or more of its binding partners, such as PD-1 and/or B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, PD-L1 binding antagonists include anti-PD-L1 antibodies and antigen-binding fragments thereof, immunoadhesins, fusion proteins, oligopeptides, small molecule antagonists, polynucleotide antagonists, and other molecules that decrease, block, inhibit, abrogate or interfere with signal transduction resulting from the interaction of PD-L1 with one or more of its binding partners, such as PD-1 and/or B7-1. In one embodiment, a PD-L1 binding antagonist reduces the negative signal mediated by or through cell surface proteins expressed on T lymphocytes and other cells through PD-L1 or PD-1 so as to render a dysfunctional T-cell less dysfunctional. In some embodiments, a PD-L1 binding antagonist is an anti-PD-L1 antibody. In a specific aspect, an anti-PD-L1 antibody is YW243.55.S70 described herein. In another specific aspect, an anti-PD-L1 antibody is MDX-1105 described herein. In still another specific aspect, an anti-PD-L1 antibody is atezolizumab (MPDL3280A) described herein. In still another specific aspect, an anti-PD-L1 antibody is MEDI4736 (druvalumab) described herein. In still another specific aspect, an anti-PD-L1 antibody is MSB0010718C (avelumab) described herein.

As used herein, a "PD-1 binding antagonist" is a molecule that decreases, blocks, inhibits, abrogates or interferes with signal transduction resulting from the interaction of PD-1 with one or more of its binding partners, such as PD-L1 and/or PD-L2. In some embodiments, the PD-1 binding antagonist is a molecule that inhibits the binding of PD-1 to its binding partners. In a specific aspect, the PD-1 binding antagonist inhibits the binding of PD-1 to PD-L1 and/or PD-L2. For example, PD-1 binding antagonists include anti-PD-1 antibodies and antigen-binding fragments thereof, immunoadhesins, fusion proteins, oligopeptides, small molecule antagonists, polynucleotide antagonists, and other molecules that decrease, block, inhibit, abrogate or interfere with signal transduction resulting from the interaction of PD-1 with PD-L1 and/or PD-L2. In one embodiment, a PD-1 binding antagonist reduces the negative signal mediated by or through cell surface proteins expressed on T lymphocytes and other cells through PD-1 or PD-L1 so as to render a dysfunctional T-cell less dysfunctional. In some embodiments, the PD-1 binding antagonist is an anti-PD-1 antibody. In a specific aspect, a PD-1 binding antagonist is MDX-1106 (nivolumab) described herein. In another specific aspect, a PD-1 binding antagonist is MK-3475 (pembrolizumab) described herein. In another specific aspect, a PD-1 binding antagonist is CT-011 (pidilizumab) described herein. In another specific aspect, a PD-1 binding antagonist is MEDI-0680 (AMP-514) described herein. In another specific aspect, a PD-1 binding antagonist is PDR001 described herein. In another specific aspect, a PD-1 binding antagonist is REGN2810 described herein. In another specific aspect, a PD-1 binding antagonist is BGB-108 described herein. In another specific aspect, a PD-1 binding antagonist is AMP-224 described herein.

The terms "Programmed Death Ligand 1" and "PD-L1" refer herein to a native sequence PD-L1 polypeptide, polypeptide variants, and fragments of a native sequence polypeptide and polypeptide variants (which are further defined herein). The PD-L1 polypeptide described herein may be that which is isolated from a variety of sources, such as from human tissue types or from another source, or prepared by recombinant or synthetic methods.

A "native sequence PD-L1 polypeptide" comprises a polypeptide having the same amino acid sequence as the corresponding PD-L1 polypeptide derived from nature.

A "PD-L1 polypeptide variant," or variations thereof, means a PD-L1 polypeptide, generally an active PD-L1 polypeptide, as defined herein having at least about 80% amino acid sequence identity with any of the native sequence PD-L1 polypeptide sequences as disclosed herein. Such PD-L1 polypeptide variants include, for instance, PD-L1 polypeptides wherein one or more amino acid residues are added, or deleted, at the N- or C-terminus of a native amino acid sequence. Ordinarily, a PD-L1 polypeptide variant will have at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to a native sequence PD-L1 polypeptide sequence as disclosed herein. Ordinarily, PD-L1 variant polypeptides are at least about 10 amino acids in length, alternatively at least about 20, 30, 40, 50, 60, 70, 80, 90, 100, 110, 120, 130, 140, 150, 160, 170, 180, 190, 200, 210, 220, 230, 240, 250, 260, 270, 280, 281, 282, 283, 284, 285, 286, 287, 288, or 289 amino acids in length, or more. Optionally, PD-L1 variant polypeptides will have no more than one conservative amino acid substitution as compared to a native PD-L1 polypeptide sequence, alternatively no more than 2, 3, 4, 5, 6, 7, 8, 9, or 10 conservative amino acid substitutions as compared to a native PD-L1 polypeptide sequence.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes cDNAs.

A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps," substitution of one or more of the naturally-occurring nucleotides with an analog, internucleotide modifications such as, for example, those with uncharged linkages (e.g., methyl phosphonates, phosphotriesters, phosphoamidates, carbamates, and the like) and with charged linkages (e.g., phosphorothioates, phosphorodithioates, and the like), those containing pendant moieties, such as, for example, proteins (e.g., nucleases, toxins, antibodies, signal peptides, poly-L-lysine, and the like), those with intercalators (e.g., acridine, psoralen, and the like), those containing chelators (e.g., metals, radioactive metals, boron, oxidative metals, and the like), those containing alkylators, those with modified linkages (e.g., alpha anomeric nucleic acids), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro-, or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs, and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. A polynucleotide can contain one or more different types of modifications as described herein and/or multiple modifications of the same type. The preceding description applies to all polynucleotides referred to herein, including RNA and DNA.

"Oligonucleotide," as used herein, generally refers to short, single stranded, polynucleotides that are, but not necessarily, less than about 250 nucleotides in length. Oligonucleotides may be synthetic. The terms "oligonucleotide" and "polynucleotide" are not mutually exclusive. The description above for polynucleotides is equally and fully applicable to oligonucleotides.

The term "primer" refers to a single-stranded polynucleotide that is capable of hybridizing to a nucleic acid and allowing polymerization of a complementary nucleic acid, generally by providing a free 3'-OH group.

The term "small molecule" refers to any molecule with a molecular weight of about 2000 daltons or less, preferably of about 500 daltons or less.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "isolated" antibody is one which has been identified and separated and/or recovered from a component of its natural environment. Contaminant components of its natural environment are materials which would interfere with research, diagnostic, and/or therapeutic uses for the antibody, and may include enzymes, hormones, and other proteinaceous or nonproteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. An isolated antibody includes the antibody in situ within recombinant cells since at least one component of the antibody's natural environment will not be present. Ordinarily, however, an isolated antibody will be prepared by at least one purification step.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

The "light chains" of antibodies (immunoglobulins) from any mammalian species can be assigned to one of two clearly distinct types, called kappa ("κ") and lambda ("λ"), based on the amino acid sequences of their constant domains.

The term "constant domain" refers to the portion of an immunoglobulin molecule having a more conserved amino acid sequence relative to the other portion of the immunoglobulin, the variable domain, which contains the antigen binding site. The constant domain contains the CH1, $CH_2$, and $CH_3$ domains (collectively, CH) of the heavy chain and the CHL (or CL) domain of the light chain.

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) both in the light chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The term "hypervariable region," "HVR," or "HV," as used herein, refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, for example, Xu et al., *Immunity* 13:37-45 (2000); Johnson and Wu, in *Methods in Molecular Biology*

248:1-25 (Lo, ed., Human Press, Totowa, N.J., 2003). Indeed, naturally occurring camelid antibodies consisting of a heavy chain only are functional and stable in the absence of light chain. See, for example, Hamers-Casterman et al., *Nature* 363:446-448 (1993); Sheriff et al., *Nature Struct. Biol.* 3:733-736 (1996).

A number of HVR delineations are in use and are encompassed herein. The Kabat Complementarity Determining Regions (CDRs) are based on sequence variability and are the most commonly used (Kabat et al., *Sequences of Proteins of Immunological Interest,* 5th Ed. Public Health Service, National Institutes of Health, Bethesda, Md. (1991)). Chothia refers instead to the location of the structural loops (Chothia and Lesk *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact |
|------|-------|-----|---------|---------|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35b | H26-H35b | H26-H32 | H30-H35b (Kabat Numbering) |
| H1 | H31-H35 | H26-H35 | H26-H32 | H30-H35 (Chothia Numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

"Framework" or "FR" residues are those variable domain residues other than the HVR residues as herein defined.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g., residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g., Kabat et al., *Sequences of Immunological Interest.* 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody.

The terms "full-length antibody," "intact antibody," and "whole antibody" are used herein interchangeably to refer to an antibody in its substantially intact form, not antibody fragments as defined below. The terms particularly refer to an antibody with heavy chains that contain an Fc region.

"Antibody fragments" comprise a portion of an intact antibody, preferably comprising the antigen-binding region thereof. In some embodiments, the antibody fragment described herein is an antigen-binding fragment. Examples of antibody fragments include Fab, Fab', F(ab')2, and Fv fragments; diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen. "Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv, see, e.g., Pluckthun, in *The Pharmacology of Monoclonal Antibodies,* vol. 113, Rosenburg and Moore eds., (Springer-Verlag, New York, 1994), pp. 269-315.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO 1993/01161; Hudson et al., Nat. Med. 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of antibodies are called α, δ, ε, γ, and μ, respectively.

The term "monoclonal antibody" as used herein refers to an antibody obtained from a population of substantially homogeneous antibodies, e.g., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target-binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target-binding sequence can be further altered, for example, to improve affinity for the target, to humanize the target-binding sequence, to improve its production in cell culture, to reduce its immunogenicity in vivo, to create a multispecific antibody, etc., and that an antibody comprising the altered target-binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the invention may be made by a variety of techniques, including, for example, the hybridoma method (e.g., Kohler and Milstein, *Nature* 256:495-97 (1975); Hongo et al., *Hybridoma* 14 (3): 253-260 (1995), Harlow et al., *Antibodies: A Laboratory Manual* (Cold Spring Harbor Laboratory Press, 2nd ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature*, 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004)), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg et al., *Intern. Rev. Immunol.* 13: 65-93 (1995)).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; and Morrison et al., *Proc. Natl. Acad. Sci. USA* 81:6851-6855 (1984)). Chimeric antibodies include PRIMATIZED® antibodies wherein the antigen-binding region of the antibody is derived from an antibody produced by, e.g., immunizing macaque monkeys with the antigen of interest.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "humanized" antibody refers to a chimeric antibody comprising amino acid residues from non-human HVRs and amino acid residues from human framework regions (FRs). In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The terms "anti-PD-L1 antibody" and "an antibody that binds to PD-L1" refer to an antibody that is capable of binding PD-L1 with sufficient affinity such that the antibody is useful as a diagnostic and/or therapeutic agent in targeting PD-L1. In one embodiment, the extent of binding of an anti-PD-L1 antibody to an unrelated, non-PD-L1 protein is less than about 10% of the binding of the antibody to PD-L1 as measured, for example, by a radioimmunoassay (RIA). In certain embodiments, an anti-PD-L1 antibody binds to an epitope of PD-L1 that is conserved among PD-L1 from different species.

The terms "anti-PD-1 antibody" and "an antibody that binds to PD-1" refer to an antibody that is capable of binding PD-1 with sufficient affinity such that the antibody is useful as a diagnostic and/or therapeutic agent in targeting PD-1. In one embodiment, the extent of binding of an anti-PD-1 antibody to an unrelated, non-PD-1 protein is less than about 10% of the binding of the antibody to PD-1 as measured, for example, by a radioimmunoassay (RIA). In certain embodiments, an anti-PD-1 antibody binds to an epitope of PD-1 that is conserved among PD-1 from different species.

A "blocking" antibody or an "antagonist" antibody is one which inhibits or reduces biological activity of the antigen it binds. Preferred blocking antibodies or antagonist antibodies substantially or completely inhibit the biological activity of the antigen.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

As used herein, the term "binds", "specifically binds to" or is "specific for" refers to measurable and reproducible interactions such as binding between a target and an antibody, which is determinative of the presence of the target in the presence of a heterogeneous population of molecules including biological molecules. For example, an antibody that binds to or specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has a dissociation constant (Kd) of $\leq 1$ µM, $\leq 100$ nM, $\leq 10$ nM, $\leq 1$ nM, or $\leq 0.1$ nM. In certain embodiments, an antibody specifically binds to an epitope on a protein that is conserved among the protein from different species. In another embodiment, specific binding can include, but does not require exclusive binding.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more.

An "immunoconjugate" is an antibody conjugated to one or more heterologous molecule(s), including but not limited to a cytotoxic agent.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG1, IgG2 (including IgG2A and IgG2B), IgG3, or IgG4 subtypes, IgA (including IgA1 and IgA2), IgE, IgD or IgM. The Ig fusions preferably include the substitution of a domain of a polypeptide or antibody described herein in the place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130. For example, useful immunoadhesins as medicaments useful for therapy herein include polypeptides that comprise the extracellular domain (ECD) or PD-1-binding portions of PD-L1 or PD-L2, or the extracellular or PD-L1- or PD-L2-binding portions of PD-1, fused to a constant domain of an immunoglobulin sequence, such as a PD-L1 ECD-Fc, a PD-L2 ECD-Fc, and a PD-1 ECD-Fc, respectively. Immunoadhesin combinations of Ig Fc and ECD of cell surface receptors are sometimes termed soluble receptors.

A "fusion protein" and a "fusion polypeptide" refer to a polypeptide having two portions covalently linked together, where each of the portions is a polypeptide having a different property. The property may be a biological property, such as activity in vitro or in vivo. The property may also be a simple chemical or physical property, such as binding to a target molecule, catalysis of a reaction, and the like. The two portions may be linked directly by a single peptide bond or through a peptide linker but are in reading frame with each other.

"Percent (%) amino acid sequence identity" with respect to the polypeptide sequences identified herein is defined as the percentage of amino acid residues in a candidate sequence that are identical with the amino acid residues in the polypeptide being compared, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are generated using the sequence comparison computer program ALIGN-2. The ALIGN-2 sequence comparison computer program was authored by Genentech, Inc. and the source code has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, California. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "detection" includes any means of detecting, including direct and indirect detection.

The term "biomarker" as used herein refers to an indicator, e.g., predictive, diagnostic, and/or prognostic, which can be detected in a sample, e.g., a particular gene or protein encoded by said gene, or one or more somatic mutations of said particular gene. The biomarker may serve as an indicator of a particular subtype of a disease or disorder (e.g., cancer) characterized by certain, molecular, pathological, histological, and/or clinical features (e.g., responsiveness to therapy including a PD-L1 axis binding antagonist). In some embodiments, a biomarker is a collection of genes or a collective number of mutations/alterations (e.g., somatic mutations) in a collection of genes. Biomarkers include, but are not limited to, polynucleotides (e.g., DNA and/or RNA), polynucleotide alterations (e.g., polynucleotide copy number alterations, e.g., DNA copy number alterations), polypeptides, polypeptide and polynucleotide modifications (e.g., post-translational modifications), carbohydrates, and/or glycolipid-based molecular markers.

The "amount" or "level" of a somatic mutation associated with an increased clinical benefit to an individual is a detectable level in a biological sample. These can be measured by methods known to one skilled in the art and also disclosed herein. The expression level or amount of a somatic mutation assessed can be used to determine the response to the treatment.

The term "level" refers to the amount of a somatic mutation in a biological sample "Increased level," "increased levels," or "elevated levels" of a somatic mutation refers to an increased level of a somatic mutation in an individual relative to a control, such as an individual or individuals who are not suffering from the disease or disorder (e.g., cancer) or an internal control (e.g., a reference gene). In some embodiments, increased levels of somatic mutations are present throughout the whole genome of an individual. In other embodiments, increased levels of somatic mutations are present within a sample (e.g., tissue sample) collected from an individual. In some embodiments, the individual has cancer (e.g., bladder cancer (e.g., UBC)).

"Decreased level," "decreased levels," "reduced level," or "reduced levels" of a somatic mutation refers to a decreased levels of a somatic mutation in an individual relative to a control, such as an individual or individuals who are not suffering from the disease or disorder (e.g., cancer) or an internal control (e.g., a reference level). In some embodiments, decreased levels of somatic mutations are present throughout the whole genome of an individual. In other embodiments, decreased levels of somatic mutations are present within a sample (e.g., tissue sample) collected from an individual. In some embodiments, the individual has cancer (e.g., bladder cancer (e.g., urothelial bladder cancer, UBC)).

The terms "level of expression" or "expression level" in general are used interchangeably and generally refer to the amount of a biomarker in a biological sample. "Expression" generally refers to the process by which information (e.g., gene-encoded and/or epigenetic information) is converted into the structures present and operating in the cell. Therefore, as used herein, "expression" may refer to transcription into a polynucleotide, translation into a polypeptide, or even polynucleotide and/or polypeptide modifications (e.g., post-translational modification of a polypeptide). Fragments of the transcribed polynucleotide, the translated polypeptide, or polynucleotide and/or polypeptide modifications (e.g., post-translational modification of a polypeptide) shall also be regarded as expressed whether they originate from a transcript generated by alternative splicing or a degraded transcript, or from a post-translational processing of the polypeptide, e.g., by proteolysis. "Expressed genes" include those that are transcribed into a polynucleotide as mRNA and then translated into a polypeptide, and also those that are transcribed into RNA but not translated into a polypeptide (for example, transfer and ribosomal RNAs).

"Increased expression," "increased expression level," "increased levels," "elevated expression," "elevated expression levels," or "elevated levels" refers to an increased expression or increased levels of a biomarker in an individual relative to a control, such as an individual or individuals who are not suffering from the disease or disorder (e.g., cancer) or an internal control (e.g., a housekeeping biomarker).

"Decreased expression," "decreased expression level," "decreased levels," "reduced expression," "reduced expression levels," or "reduced levels" refers to a decrease expression or decreased levels of a biomarker in an individual relative to a control, such as an individual or individuals who are not suffering from the disease or disorder (e.g., cancer) or an internal control (e.g., a housekeeping biomarker).

"Amplification," as used herein generally refers to the process of producing multiple copies of a desired sequence. "Multiple copies" mean at least two copies. A "copy" does not necessarily mean perfect sequence complementarity or identity to the template sequence. For example, copies can include nucleotide analogs such as deoxyinosine, intentional sequence alterations (such as sequence alterations introduced through a primer comprising a sequence that is hybridizable, but not complementary, to the template), and/or sequence errors that occur during amplification.

The term "multiplex-PCR" refers to a single PCR reaction carried out on nucleic acid obtained from a single source (e.g., an individual) using more than one primer set for the purpose of amplifying two or more DNA sequences in a single reaction.

The technique of "polymerase chain reaction" or "PCR" as used herein generally refers to a procedure wherein minute amounts of a specific piece of nucleic acid, RNA and/or DNA, are amplified as described, for example, in U.S. Pat. No. 4,683,195. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage, or plasmid sequences, etc. See generally Mullis et al., *Cold Spring Harbor Symp. Quant. Biol.* 51:263 (1987) and Erlich, ed., PCR Technology, (Stockton Press, N Y, 1989). As used herein, PCR is considered to be one, but not the only, example of a nucleic acid polymerase reaction method for amplifying a nucleic acid test sample, comprising the use of a known nucleic acid (DNA or RNA) as a primer and utilizes a nucleic acid polymerase to amplify or generate a specific piece of nucleic acid or to amplify or generate a specific piece of nucleic acid which is complementary to a particular nucleic acid.

"Quantitative real-time polymerase chain reaction" or "qRT-PCR" refers to a form of PCR wherein the amount of PCR product is measured at each step in a PCR reaction. This technique has been described in various publications including, for example, Cronin et al., *Am. J. Pathol.* 164(1): 35-42 (2004) and Ma et al., *Cancer Cell* 5:607-616 (2004).

The term "microarray" refers to an ordered arrangement of hybridizable array elements, preferably polynucleotide probes, on a substrate.

The term "diagnosis" is used herein to refer to the identification or classification of a molecular or pathological state, disease or condition (e.g., cancer). For example, "diagnosis" may refer to identification of a particular type of cancer. "Diagnosis" may also refer to the classification of a particular subtype of cancer, for instance, by histopathological criteria, or by molecular features (e.g., a subtype characterized by expression of one or a combination of biomarkers (e.g., particular genes or proteins encoded by said genes)).

The term "aiding diagnosis" is used herein to refer to methods that assist in making a clinical determination regarding the presence, or nature, of a particular type of symptom or condition of a disease or disorder (e.g., cancer). For example, a method of aiding diagnosis of a disease or condition (e.g., cancer) can comprise measuring certain somatic mutations in a biological sample from an individual.

The term "sample," as used herein, refers to a composition that is obtained or derived from a subject and/or individual of interest that contains a cellular and/or other molecular entity that is to be characterized and/or identified, for example, based on physical, biochemical, chemical, and/or physiological characteristics. For example, the phrase "disease sample" and variations thereof refers to any sample obtained from a subject of interest that would be expected or is known to contain the cellular and/or molecular entity that is to be characterized. Samples include, but are not limited to, tissue samples, primary or cultured cells or cell lines, cell supernatants, cell lysates, platelets, serum, plasma, vitreous fluid, lymph fluid, synovial fluid, follicular fluid, seminal fluid, amniotic fluid, milk, whole blood, blood-derived cells, urine, cerebro-spinal fluid, saliva, sputum, tears, perspiration, mucus, tumor lysates, and tissue culture medium, tissue extracts such as homogenized tissue, tumor tissue, cellular extracts, and combinations thereof.

By "tissue sample" or "cell sample" is meant a collection of similar cells obtained from a tissue of a subject or individual. The source of the tissue or cell sample may be solid tissue as from a fresh, frozen and/or preserved organ, tissue sample, biopsy, and/or aspirate; blood or any blood constituents such as plasma; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease tissue/organ. For instance, a "tumor sample" is a tissue sample obtained from a tumor or other cancerous tissue. The tissue sample may contain a mixed population of cell types (e.g., tumor cells and non-tumor cells, cancerous cells and non-cancerous cells). The tissue sample may contain compounds which are not naturally intermixed with the tissue in nature such as preservatives, anticoagulants, buffers, fixatives, nutrients, antibiotics, or the like.

A "tumor cell" as used herein, refers to any tumor cell present in a tumor or a sample thereof. Tumor cells may be distinguished from other cells that may be present in a tumor sample, for example, stromal cells and tumor-infiltrating immune cells, using methods known in the art and/or described herein.

A "reference sample," "reference cell," "reference tissue," "control sample," "control cell," or "control tissue," as used herein, refers to a sample, cell, tissue, standard, or level that is used for comparison purposes. In one embodiment, a reference sample, reference cell, reference tissue, control sample, control cell, or control tissue is obtained from a healthy and/or non-diseased part of the body (e.g., tissue or cells) of the same subject or individual. For example, the reference sample, reference cell, reference tissue, control sample, control cell, or control tissue may be healthy and/or non-diseased cells or tissue adjacent to the diseased cells or tissue (e.g., cells or tissue adjacent to a tumor). In another embodiment, a reference sample is obtained from an untreated tissue and/or cell of the body of the same subject or individual. In yet another embodiment, a reference sample, reference cell, reference tissue, control sample, control cell, or control tissue is obtained from a healthy and/or non-diseased part of the body (e.g., tissues or cells) of an individual who is not the subject or individual. In even another embodiment, a reference sample, reference cell, reference tissue, control sample, control cell, or control tissue is obtained from an untreated tissue and/or cell of the body of an individual who is not the subject or individual.

For the purposes herein a "section" of a tissue sample is meant a single part or piece of a tissue sample, for example, a thin slice of tissue or cells cut from a tissue sample (e.g., a tumor sample). It is to be understood that multiple sections of tissue samples may be taken and subjected to analysis, provided that it is understood that the same section of tissue sample may be analyzed at both morphological and molecular levels, or analyzed with respect to polypeptides (e.g., by immunohistochemistry) and/or polynucleotides (e.g., by in situ hybridization).

By "correlate" or "correlating" is meant comparing, in any way, the performance and/or results of a first analysis or protocol with the performance and/or results of a second analysis or protocol. For example, one may use the results of a first analysis or protocol in carrying out a second protocol and/or one may use the results of a first analysis or protocol to determine whether a second analysis or protocol should be performed. With respect to the embodiment of polypeptide analysis or protocol, one may use the results of the polypeptide expression analysis or protocol to determine whether a specific therapeutic regimen should be performed. With respect to the embodiment of polynucleotide analysis or protocol, one may use the results of the polynucleotide expression analysis or protocol to determine whether a specific therapeutic regimen should be performed.

"Individual response" or "response" can be assessed using any endpoint indicating a benefit to the individual, including, without limitation, (1) inhibition, to some extent, of disease progression (e.g., cancer progression), including slowing down or complete arrest; (2) a reduction in tumor size; (3) inhibition (i.e., reduction, slowing down, or complete stopping) of cancer cell infiltration into adjacent peripheral organs and/or tissues; (4) inhibition (i.e. reduction, slowing down, or complete stopping) of metastasis; (5) relief, to some extent, of one or more symptoms associated with the disease or disorder (e.g., cancer); (6) increase or extension in the length of survival, including overall survival and progression free survival; and/or (7) decreased mortality at a given point of time following treatment.

An "effective response" of a patient or a patient's "responsiveness" to treatment with a medicament and similar wording refers to the clinical or therapeutic benefit imparted to a patient at risk for, or suffering from, a disease or disorder, such as cancer. In one embodiment, such benefit includes any one or more of: extending survival (including overall survival and/or progression-free survival); resulting in an objective response (including a complete response or a partial response); or improving signs or symptoms of cancer. In one embodiment, the level of somatic mutation in tumor cells, for example, as determined using methods disclosed herein, is used to identify a patient who is predicted to have an increased likelihood of being responsive to treatment with a medicament (e.g., treatment comprising a PD-L1 axis binding antagonist, e.g., an anti-PD-L1 antibody), relative to a patient who does not have the same level of somatic mutations. In one embodiment, an increased level of somatic mutations in tumor cells, for example, as determined using methods disclosed herein is used to identify the patient who is predicted to have an increased likelihood of being responsive to treatment with a medicament (e.g., anti-PD-L1 antibody), relative to a patient who does not have an increased level of somatic mutations.

An "objective response" refers to a measurable response, including complete response (CR) or partial response (PR). In some embodiments, the "objective response rate (ORR)" refers to the sum of complete response (CR) rate and partial response (PR) rate.

By "complete response" or "CR" is intended the disappearance of all signs of cancer (e.g., disappearance of all target lesions) in response to treatment. This does not always mean the cancer has been cured.

"Sustained response" refers to the sustained effect on reducing tumor growth after cessation of a treatment. For example, the tumor size may be the same size or smaller as compared to the size at the beginning of the medicament administration phase. In some embodiments, the sustained response has a duration at least the same as the treatment duration, at least 1.5×, 2.0×, 2.5×, or 3.0× length of the treatment duration, or longer.

As used herein, "reducing or inhibiting cancer relapse" means to reduce or inhibit tumor or cancer relapse or tumor or cancer progression. As disclosed herein, cancer relapse and/or cancer progression include, without limitation, cancer metastasis.

As used herein, "partial response" or "PR" refers to a decrease in the size of one or more tumors or lesions, or in the extent of cancer in the body, in response to treatment. For example, in some embodiments, PR refers to at least a 30% decrease in the sum of the longest diameters (SLD) of target lesions, taking as reference the baseline SLD.

As used herein, "stable disease" or "SD" refers to neither sufficient shrinkage of target lesions to qualify for PR, nor sufficient increase to qualify for PD, taking as reference the smallest SLD since the treatment started.

As used herein, "progressive disease" or "PD" refers to at least a 20% increase in the SLD of target lesions, taking as reference the smallest SLD recorded since the treatment started or the presence of one or more new lesions.

The term "survival" refers to the patient remaining alive, and includes overall survival as well as progression-free survival As used herein, "progression-free survival" (PFS) refers to the length of time during and after treatment during which the disease being treated (e.g., cancer) does not get worse. Progression-free survival may include the amount of time patients have experienced a complete response or a partial response, as well as the amount of time patients have experienced stable disease.

As used herein, "overall survival" (OS) refers to the percentage of individuals in a group who are likely to be alive after a particular duration of time.

By "extending survival" is meant increasing overall or progression-free survival in a treated patient relative to an untreated patient (i.e. relative to a patient not treated with the medicament), or relative to a patient who does not have somatic mutations at the designated level, and/or relative to a patient treated with an anti-tumor agent.

The term "substantially the same," as used herein, denotes a sufficiently high degree of similarity between two numeric values, such that one of skill in the art would consider the difference between the two values to be of little or no biological and/or statistical significance within the context of the biological characteristic measured by said values (e.g., Kd values or mutation levels). The difference between said two values is, for example, less than about 50%, less than about 40%, less than about 30%, less than about 20%, and/or less than about 10%, as a function of the reference/comparator value.

The phrase "substantially different," as used herein, denotes a sufficiently high degree of difference between two numeric values such that one of skill in the art would consider the difference between the two values to be of statistical significance within the context of the biological characteristic measured by said values (e.g., Kd values or mutation levels). The difference between said two values is, for example, greater than about 10%, greater than about 20%, greater than about 30%, greater than about 40%, and/or greater than about 50%, as a function of the value for the reference/comparator molecule.

The word "label" when used herein refers to a compound or composition that is conjugated or fused directly or indirectly to a reagent such as a polynucleotide probe or an antibody and facilitates detection of the reagent to which it is conjugated or fused. The label may itself be detectable (e.g., radioisotope labels or fluorescent labels) or, in the case of an enzymatic label, may catalyze chemical alteration of a substrate compound or composition which is detectable. The term is intended to encompass direct labeling of a probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin.

A "therapeutically effective amount" refers to an amount of a therapeutic agent to treat or prevent a disease or disorder in a mammal. In the case of cancers, the therapeutically effective amount of the therapeutic agent may reduce the number of cancer cells; reduce the primary tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), response rates (e.g., CR and PR), duration of response, and/or quality of life.

A "disorder" is any condition that would benefit from treatment including, but not limited to, chronic and acute disorders or diseases including those pathological conditions which predispose the mammal to the disorder in question.

The terms "cancer" and "cancerous" refer to or describe the physiological condition in mammals that is typically characterized by unregulated cell growth. Included in this definition are benign and malignant cancers. By "early stage cancer" or "early stage tumor" is meant a cancer that is not invasive or metastatic or is classified as a Stage 0, 1, or 2 cancer. Examples of cancer include, but are not limited to, carcinoma, lymphoma, blastoma (including medulloblastoma and retinoblastoma), sarcoma (including liposarcoma and synovial cell sarcoma), neuroendocrine tumors (including carcinoid tumors, gastrinoma, and islet cell cancer), mesothelioma, schwannoma (including acoustic neuroma), meningioma, adenocarcinoma, melanoma, and leukemia or lymphoid malignancies. More particular examples of such cancers include bladder cancer (e.g., urothelial bladder cancer (e.g., transitional cell or urothelial carcinoma, non-muscle invasive bladder cancer, muscle-invasive bladder cancer, and metastatic bladder cancer) and non-urothelial bladder cancer), squamous cell cancer (e.g., epithelial squamous cell cancer), lung cancer including small-cell lung cancer (SCLC), non-small cell lung cancer (NSCLC), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, hepatoma, breast cancer (including metastatic breast cancer), colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, Merkel cell cancer, mycoses fungoids, testicular cancer, esophageal cancer, tumors of the biliary tract, as well as head and neck cancer and hematological malignancies. In some embodiments, the cancer is triple-negative metastatic breast cancer, including any histologically confirmed triple-negative (ER−, PR−, HER2−) adenocarcinoma of the breast with locally recurrent or metastatic disease (where the locally recurrent disease is not amenable to resection with curative intent). In some embodiments, the cancer is bladder cancer. In particular embodiments, the bladder cancer is urothelial bladder cancer.

The term "tumor," as used herein, refers to all neoplastic cell growth and proliferation, whether malignant or benign, and all pre-cancerous and cancerous cells and tissues. The terms "cancer," "cancerous," and "tumor" are not mutually exclusive as referred to herein.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies (e.g., anti-PD-L1 antibodies and/or anti-PD-1 antibodies) are used to delay development of a disease or to slow the progression of a disease.

The term "anti-cancer therapy" refers to a therapy useful in treating cancer. Examples of anti-cancer therapeutic agents include, but are limited to, cytotoxic agents, chemotherapeutic agents, growth inhibitory agents, agents used in radiation therapy, anti-angiogenesis agents, apoptotic agents, anti-tubulin agents, and other agents to treat cancer, for example, anti-CD20 antibodies, platelet derived growth factor inhibitors (e.g., GLEEVEC™ (imatinib mesylate)), a COX-2 inhibitor (e.g., celecoxib), interferons, cytokines, antagonists (e.g., neutralizing antibodies) that bind to one or more of the following targets PDGFR-β, BlyS, APRIL, BCMA receptor(s), TRAIL/Apo2, other bioactive and organic chemical agents, and the like. Combinations thereof are also included in the invention.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, and radioactive isotopes of Lu), chemotherapeutic agents, e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "chemotherapeutic agent" is a chemical compound useful in the treatment of cancer. Examples of chemotherapeutic agents include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (see, e.g., Nicolaou et al., *Angew. Chem Intl. Ed. Engl.*, 33: 183-186 (1994)); dynemicin, including dynemicin A; an esperamicin; as well as neocarzinostatin chromophore and related chromoprotein enediyne antiobiotic chromophores, aclacinomysins, actinomycin, authramycin, azaserine, bleomycins, cactinomycin, carabicin, carminomycin, carzinophilin, chromomycin, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, OR); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, for example taxanes including TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Illinois), and TAXOTERE® docetaxel (Rhône-Poulenc Rorer, Antony, France); chloranbucil; gemcitabine (GEMZAR®); 6-thioguanine; mercaptopurine; methotrexate; platinum or platinum-based chemotherapy agents and platinum analogs, such as cisplatin, carboplatin, oxaliplatin (ELOXATIN™), satraplatin, picoplatin, nedaplatin, triplatin, and lipoplatin; vinblastine (VELBAN®); platinum; etoposide (VP-16); ifosfamide; mitoxantrone; vincristine (ONCOVIN®); oxaliplatin; leucovorin; vinorelbine (NAVELBINE®); novantrone; edatrexate; daunomycin; aminopterin; ibandronate; topoisomerase inhibitor RFS 2000; difluorometlhylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovorin. Additional chemotherapeutic agents include the cytotoxic agents useful as antibody drug conjugates, such as maytansinoids (DM1, for example) and the auristatins MMAE and MMAF, for example.

"Chemotherapeutic agents" also include "anti-hormonal agents" or "endocrine therapeutics" that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGFR); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

Chemotherapeutic agents also include antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length IgG1 λ antibody genetically modified to recognize interleukin-12 p40 protein.

Chemotherapeutic agents also include "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. Eur. J. Cancer 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6.3, and E7.6. 3 and described in U.S. Pat. No. 6,235,883; MDX-447 (Medarex Inc); and mAb 806 or humanized mAb 806 (Johns et al., J. Biol. Chem. 279(29): 30375-30384 (2004)). The anti-EGFR antibody may be conjugated with a cytotoxic agent, thus generating an immunoconjugate (see, e.g., EP 659,439A2, Merck Patent GmbH). EGFR antagonists include small molecules such as compounds described in U.S. Pat. Nos. 5,616,582, 5,457, 105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO 98/14451, WO 98/50038, WO 99/09016, and WO 99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl) propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenyl-ethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); and dual EGFR/HER2 tyrosine kinase inhibitors such as lapatinib (TYKERB®, GSK572016 or N-[3-chloro-4-[(3 fluorophenyl)methoxy]phenyl]-6[5[[[2methylsulfonyl]ethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitors such as TAK165 available from Takeda; CP-724, 714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from GlaxoSmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035, 4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis(4-fluoroanilino)phthalimide); tyrphostines containing nitrothiophene moieties; PD-0183805 (Warner-Lamber); antisense molecules (e.g., those that bind to HER-encoding nucleic acid); quinoxalines (U.S. Pat. No. 5,804, 396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN Bio-Therapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNFα) blockers such as etanercept (ENBREL®), infliximab (REMICADE®), adalimumab (HUMIRA®), certolizumab pegol (CIMZIA®), golimumab (SIMPONI®), Interleukin 1 (IL-1) blockers such as anakinra (KINERET®), T-cell co-stimulation blockers such as abatacept (ORENCIA®), Interleukin 6 (IL-6) blockers such as tocilizumab (ACTEMERA®); Interleukin 13 (IL-13) blockers such as lebrikizumab; Interferon alpha (IFN) blockers such as rontalizumab; beta 7 integrin blockers such as rhuMAb Beta7; IgE pathway blockers such as Anti-M1 prime; Secreted homotrimeric LTa3 and membrane bound heterotrimer LTa1/β2 blockers such as Anti-lymphotoxin alpha (LTa); miscellaneous investigational agents such as thioplatin, PS-341, phenylbutyrate, ET-18-OCH3, and farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g., celecoxib or etoricoxib), proteosome inhibitor (e.g., PS341); CCI-779; tipifarnib (R11577); orafenib, ABT510; Bcl-2 inhibitor such as oblimersen sodium (GENASENSE®); pixantrone; farnesyltransferase inhibitors such as lonafarnib (SCH 6636, SARASAR™); and pharmaceutically acceptable salts, acids or derivatives of any of the above; as well as combinations of two or more of the above.

The term "prodrug" as used herein refers to a precursor or derivative form of a pharmaceutically active substance that is less cytotoxic to tumor cells compared to the parent drug and is capable of being enzymatically activated or converted into the more active parent form. See, for example, Wilman, "Prodrugs in Cancer Chemotherapy" *Biochemical Society Transactions,* 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

A "growth inhibitory agent" when used herein refers to a compound or composition which inhibits growth and/or proliferation of a cell (e.g., a cell whose growth is dependent on PD-L1 expression) either in vitro or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as the anthracycline antibiotic doxorubicin ((8S-cis)-10-[(3-amino-2,3,6-trideoxy-α-L-lyxo-hexapyranosyl)oxy]-7,8,9,10-tetrahydro-6,8,11-trihydroxy-8-(hydroxyacetyl)-1-methoxy-5,12-naphthacenedione), epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *"The Molecular Basis of Cancer,"* Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one-time administration and typical dosages range from 10 to 200 units (Grays) per day.

As used herein, the terms "patient" or "subject" are used interchangeably and refer to any single animal, more preferably a mammal (including such non-human animals as, for example, dogs, cats, horses, rabbits, zoo animals, cows, pigs, sheep, and non-human primates) for which treatment is desired. In particular embodiments, the patient herein is a human.

As used herein, "administering" is meant a method of giving a dosage of a compound (e.g., an antagonist) or a pharmaceutical composition (e.g., a pharmaceutical composition including an antagonist) to a subject (e.g., a patient). Administering can be by any suitable means, including parenteral, intrapulmonary, and intranasal, and, if desired for local treatment, intralesional administration. Parenteral infusions include, for example, intramuscular, intravenous, intraarterial, intraperitoneal, or subcutaneous administration. Dosing can be by any suitable route, e.g., by injections, such as intravenous or subcutaneous injections, depending in part on whether the administration is brief or chronic. Various dosing schedules including but not limited to single or multiple administrations over various time-points, bolus administration, and pulse infusion are contemplated herein.

The term "concurrently" is used herein to refer to administration of two or more therapeutic agents, where at least part of the administration overlaps in time. Accordingly, concurrent administration includes a dosing regimen when the administration of one or more agent(s) continues after discontinuing the administration of one or more other agent(s).

By "reduce or inhibit" is meant the ability to cause an overall decrease of 20%, 30%, 40%, 50%, 60%, 70%, 75%, 80%, 85%, 90%, 95%, or greater. Reduce or inhibit can refer, for example, to the symptoms of the disorder being treated, the presence or size of metastases, or the size of the primary tumor.

The term "package insert" is used to refer to instructions customarily included in commercial packages of therapeutic products, that contain information about the indications, usage, dosage, administration, combination therapy, contraindications, and/or warnings concerning the use of such therapeutic products.

A "sterile" formulation is aseptic or free from all living microorganisms and their spores.

An "article of manufacture" is any manufacture (e.g., a package or container) or kit comprising at least one reagent, e.g., a medicament for treatment of a disease or disorder (e.g., cancer), or a probe for specifically detecting a biomarker (e.g., PD-L1) described herein. In certain embodiments, the manufacture or kit is promoted, distributed, or sold as a unit for performing the methods described herein.

The phrase "based on" when used herein means that the information about one or more biomarkers is used to inform a treatment decision, information provided on a package insert, or marketing/promotional guidance, etc.

III. Methods

A. Diagnostic Methods Based on the Level of Cancer-Related Genes

Provided herein are methods for determining whether a patient suffering from a cancer (e.g., a bladder cancer (e.g., a urothelial bladder cancer (UBC)) is likely to respond to treatment comprising a PD-L1 axis binding antagonist. Also provided herein are methods for predicting responsiveness of a patient suffering from a cancer (e.g., a bladder cancer (e.g., a UBC)) to treatment comprising a PD-L1 axis binding antagonist. Further provided herein are methods for selecting a therapy for a patient suffering from a cancer (e.g., a bladder cancer (e.g., an urothelial bladder cancer)). Any of the preceding methods may be based on the level of somatic mutations in any of the genes described herein in a tumor sample. Any of the methods may further include administering to the patient a PD-L1 axis binding antagonist (for example, as described in Section D, below) to the patient. Any of the methods may further include administering an effective amount of a second therapeutic agent to the patient.

The invention provides a method for treating a patient suffering from a bladder cancer, the method comprising administering to the patient a therapeutically effective amount of a PD-L1 axis binding antagonist, wherein the tumor sample obtained from the patient has been determined to have an increased level of a somatic mutation in at least one or more (e.g., 1, 2, 3, 4, 5, 6, 7, 8, 9, 10, 20, 30, 40, 50, 60, 70, 80, 90, 100, 150, 200, 250, 300 or more) genes as set forth in Table 1 relative to a reference level of somatic mutation in the at least one gene set forth in Table 1. In other instances, about 1% or more (e.g., about 2% or more, about 3% or more, about 4% or more, about 5% or more, about 6% or more, about 7% or more, about 8% or more, about 9% or more, about 10% or more, about 11% or more, about 12% or more, about 13% or more, about 14% or more, about 15% or more, about 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, about 95% or more, or about 99% or more) of the genes set forth in Table 1 was determined to have increased somatic mutations. For example, in some instances, the tumor sample obtained from the patient has been determined to have increased levels of somatic mutations in at least one-half or about 50% of the genes set forth in Table 1. In some instances, the tumor sample obtained from the patient has been determined to have increased levels of somatic mutations in at least two-thirds or about 67% of the genes set forth in Table 1. In some instances, the tumor sample obtained from the patient has been determined to have increased levels of somatic mutations in at least three-fourths or about 75% of the genes set forth in Table 1.

TABLE 1

| Cancer-related Genes | | | | | | | | | |
|---|---|---|---|---|---|---|---|---|---|
| ABL1 | BRAF | CHEK1 | FANCC | GATA3 | JAK2 | MITF | PDCD1LG2 | RBM10 | STAT4 |
| ABL2 | BRCA1 | CHEK2 | FANCD2 | GATA4 | JAK3 | MLH1 | PDGFRA | RET | STK11 |
| ACVR1B | BRCA2 | CIC | FANCE | GATA6 | JUN | MPL | PDGFRB | RICTOR | SUFU |
| AKT1 | BRD4 | CREBBP | FANCF | GID4 (C17orf39) | KAT6A (MYST3) | MRE11A | PDK1 | RNF43 | SYK |
| AKT2 | BRIP1 | CRKL | FANCG | GLI1 | KDM5A | MSH2 | PIK3C2B | ROS1 | TAF1 |
| AKT3 | BTG1 | CRLF2 | FANCL | GNA11 | KDM5C | MSH6 | PIK3CA | RPTOR | TBX3 |
| ALK | BTK | CSF1R | FAS | GNA13 | KDM6A | MTOR | PIK3CB | RUNX1 | TERC |
| AMER1 (FAM123B) | C11orf30 (EMSY) | CTCF | FAT1 | GNAQ | KDR | MUTYH | PIK3CG | RUNX1T1 | TERT (promoter only) |
| APC | CARD11 | CTNNA1 | FBXW7 | GNAS | KEAP1 | MYC | PIK3R1 | SDHA | TET2 |
| AR | CBFB | CTNNB1 | FGF10 | GPR124 | KEL | MYCL (MYCL1) | PIK3R2 | SDHB | TGFBR2 |
| ARAF | CBL | CUL3 | FGF14 | GRIN2A | KIT | MYCN | PLCG2 | SDHC | TNFAIP3 |
| ARFRP1 | CCND1 | CYLD | FGF19 | GRM3 | KLHL6 | MYD88 | PMS2 | SDHD | TNFRSF14 |
| ARID1A | CCND2 | DAXX | FGF23 | GSK3B | KMT2A (MLL) | NF1 | POLD1 | SETD2 | TOP1 |
| ARID1B | CCND3 | DDR2 | FGF3 | H3F3A | KMT2C (MLL3) | NF2 | POLE | SF3B1 | TOP2A |
| ARID2 | CCNE1 | DICER1 | FGF4 | HGF | KMT2D (MLL2) | NFE2L2 | PPP2R1A | SLIT2 | TP53 |
| ASXL1 | CD274 | DNMT3A | FGF6 | HNF1A | KRAS | NFKBIA | PRDM1 | SMAD2 | TSC1 |

TABLE 1-continued

Cancer-related Genes

| | | | | | | | | | |
|---|---|---|---|---|---|---|---|---|---|
| ATM | CD79A | DOT1L | FGFR1 | HRAS | LMO1 | NKX2-1 | PREX2 | SMAD3 | TSC2 |
| ATR | CD79B | EGFR | FGFR2 | HSD3B1 | LRP1B | NOTCH1 | PRKAR1A | SMAD4 | TSHR |
| ATRX | CDC73 | EP300 | FGFR3 | HSP90AA1 | LYN | NOTCH2 | PRKCI | SMARCA4 | U2AF1 |
| AURKA | CDH1 | EPHA3 | FGFR4 | IDH1 | LZTR1 | NOTCH3 | PRKDC | SMARCB1 | VEGFA |
| AURKB | CDK12 | EPHA5 | FH | IDH2 | MAGI2 | NPM1 | PRSS8 | SMO | VHL |
| AXIN1 | CDK4 | EPHA7 | FLCN | IGF1R | MAP2K1 | NRAS | PTCH1 | SNCAIP | WISP3 |
| AXL | CDK6 | EPHB1 | FLT1 | IGF2 | MAP2K2 | NSD1 | PTEN | SOCS1 | WT1 |
| BAP1 | CDK8 | ERBB2 | FLT3 | IKBKE | MAP2K4 | NTRK1 | PTPN11 | SOX10 | XPO1 |
| BARD1 | CDKN1A | ERBB3 | FLT4 | IKZF1 | MAP3K1 | NTRK2 | QKI | SOX2 | ZBTB2 |
| BCL2 | CDKN1B | ERBB4 | FOXL2 | IL7R | MCL1 | NTRK3 | RAC1 | SOX9 | ZNF217 |
| BCL2L1 | CDKN2A | ERG | FOXP1 | INHBA | MDM2 | NUP93 | RAD50 | SPEN | ZNF703 |
| BCL2L2 | CDKN2B | ERRFI1 | FRS2 | INPP4B | MDM4 | PAK3 | RAD51 | SPOP | |
| BCL6 | CDKN2C | ESR1 | FUBP1 | IRF2 | MED12 | PALB2 | RAF1 | SPTA1 | |
| BCOR | CEBPA | EZH2 | GABRA6 | IRF4 | MEF2B | PARK2 | RANBP2 | SRC | |
| BCORL1 | CHD2 | FAM46C | GATA1 | IRS2 | MEN1 | PAX5 | RARA | STAG2 | |
| BLM | CHD4 | FANCA | GATA2 | JAK1 | MET | PBRM1 | RB1 | STAT3 | |

The presence and/or levels (amount) of somatic mutations can be determined qualitatively and/or quantitatively based on any suitable criterion known in the art, including but not limited to the measurement of DNA, mRNA, cDNA, proteins, protein fragments, and/or gene copy number levels in an individual. In some instances, a comprehensive genomic profile of an individual is determined. In some instances, a comprehensive genomic profile of a sample (e.g., tissue sample, formalin-fixed, paraffin-embedded (FFPE) tissues sample, core or fine needle biopsies) collected from an individual is determined. In some instances, the determination of the genomic profile comprises applying next-generation sequencing methods, known in the art or described herein, to identify genomic alterations (e.g., somatic mutations (e.g., base substitutions, insertions and deletions (indels), copy number alterations (CNAs) and rearrangements)) known to be unambiguous drivers of cancer (e.g., solid tumors). In some instances, the test simultaneously sequences the coding region of 315 cancer-related genes plus introns from 28 genes often rearranged or altered in cancer to a typical median depth of coverage of greater than 500×. In some instances, each covered sequencing read represents a unique DNA fragment to enable the highly sensitive and specific detection of genomic alterations that occur at low frequencies due to tumor heterogeneity, low tumor purity, and small tissue samples.

The invention provides a method for determining whether a patient suffering from a bladder cancer is likely to respond to treatment comprising a PD-L1 axis binding antagonist, the method comprising determining the level of somatic mutation in a tumor sample obtained from the patient, wherein an increased level of somatic mutation in at least one or more (e.g., 1, 2, 3, 4, 5, 6, 7, 8, 9, 10, 20, 30, 40, 50, 60, 70, 80, 90, 100, 150, 200, 250, 300 or more) genes as set forth in Table 1 of the tumor sample indicates that the patient is likely to respond to treatment comprising a PD-L1 axis binding antagonist. For example, in some instances, an increased level of somatic mutations in at least about one-third of the genes set forth in Table 1 in a tumor sample indicates that the patient is likely to respond to treatment comprising a PD-L1 axis binding antagonist. In other instances, an increased level of somatic mutations in at least about two-thirds of the genes set forth in Table 1 in a tumor sample indicates that the patient is likely to respond to treatment comprising a PD-L1 axis binding antagonist. In other instances, an increased level of somatic mutations in at least about three-fourths of the genes set forth in Table 1 in a tumor sample indicates that the patient is likely to respond to treatment comprising a PD-L1 axis binding antagonist. In other instances, about 1% or more (e.g., about 2% or more, about 3% or more, about 4% or more, about 5% or more, about 6% or more, about 7% or more, about 8% or more, about 9% or more, about 10% or more, about 11% or more, about 12% or more, about 13% or more, about 14% or more, about 15% or more, about 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, about 95% or more, or about 99% or more) of the genes set forth in Table 1 was determined to have increased somatic mutations. For example, in some instances, the tumor sample obtained from the patient has been determined to have increased levels of somatic mutations in at least one-half or about 50% of the genes set forth in Table 1. In some instances, the tumor sample obtained from the patient has been determined to have increased levels of somatic mutations in at least two-thirds or about 67% of the genes set forth in Table 1. In some instances, the tumor sample obtained from the patient has been determined to have increased levels of somatic mutations in at least three-fourths or about 75% of the genes set forth in Table 1.

The invention further provides a method for predicting responsiveness of a patient suffering from a bladder cancer to treatment comprising a PD-L1 axis binding antagonist, the method comprising determining the level of somatic mutation in a tumor sample obtained from the patient, wherein an increased level of a somatic mutation in at least one or more (e.g., 1, 2, 3, 4, 5, 6, 7, 8, 9, 10, 20, 30, 40, 50, 60, 70, 80, 90, 100, 150, 200, 250, 300 or more) genes as set forth in Table 1 of the tumor sample indicates that the patient is likely to respond to treatment comprising a PD-L1 axis binding antagonist. For example, in some instances, an increased level of somatic mutations in at least about one-third of the genes set forth in Table 1 in a tumor sample indicates that the patient is likely to respond to treatment comprising a PD-L1 axis binding antagonist. In other instances, an increased level of somatic mutations in at least about two-thirds of the genes set forth in Table 1 in a tumor sample indicates that the patient is likely to respond to treatment comprising a PD-L1 axis binding antagonist. In other instances, an increased level of somatic mutations in at least about three-fourths of the genes set forth in Table 1 in a tumor sample indicates that the patient is likely to respond to treatment comprising a PD-L1 axis binding antagonist. In other instances, about 1% or more (e.g., about 2% or more, about 3% or more, about 4% or more, about 5% or more, about 6% or more, about 7% or more, about 8% or more, about 9% or more, about 10% or more, about 11% or more, about 12% or more, about 13% or more, about 14% or more, about 15% or more, about 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, about 95% or more, or about 99% or more) of the genes set forth in Table 1 was determined to have increased somatic mutations. For example, in some instances, the tumor sample obtained from the patient has been determined to have increased levels of somatic mutations in at least one-half or about 50% of the genes set forth in Table 1. In some instances, the tumor sample obtained from the patient has been determined to have increased levels of somatic mutations in at least two-thirds or about 67% of the genes set forth in Table 1. In some instances, the tumor sample obtained from the patient has been determined to have increased levels of somatic mutations in at least three-fourths or about 75% of the genes set forth in Table 1.

The invention yet also provides a method for selecting a therapy for a patient suffering from a bladder cancer, the method comprising determining the level of somatic mutation in a tumor sample obtained from the patient, wherein an increased level of a somatic mutation in at least one or more (e.g., 1, 2, 3, 4, 5, 6, 7, 8, 9, 10, 20, 30, 40, 50, 60, 70, 80, 90, 100, 150, 200, 250, 300 or more) genes as set forth in Table 1 of the tumor sample indicates that the patient is likely to respond to treatment comprising a PD-L1 axis binding antagonist. For example, in some instances, an increased level of somatic mutations in at least about one-third of the genes set forth in Table 1 in a tumor sample indicates that the patient is likely to respond to treatment comprising a PD-L1 axis binding antagonist. In other instances, an increased level of somatic mutations in at least about two-thirds of the genes set forth in Table 1 in a tumor sample indicates that the patient is likely to respond to treatment comprising a PD-L1 axis binding antagonist. In other instances, an increased level of somatic mutations in at least about three-fourths of the genes set forth in Table 1 in a tumor sample indicates that the patient is likely to respond to treatment comprising a PD-L1 axis binding antagonist. In other instances, about 1% or more (e.g., about 2% or more, about 3% or more, about 4% or more, about 5% or more, about 6% or more, about 7% or more, about 8% or more, about 9% or more, about 10% or more, about 11% or more, about 12% or more, about 13% or more, about 14% or more, about 15% or more, about 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, about 95% or more, or about 99% or more) of the genes set forth in Table 1 was determined to have increased somatic mutations. For example, in some instances, the tumor sample obtained from the patient has been determined to have increased levels of somatic mutations in at least one-half or about 50% of the genes set forth in Table 1. In some instances, the tumor sample obtained from the patient has been determined to have increased levels of somatic mutations in at least two-thirds or about 67% of the genes set forth in Table 1. In some instances, the tumor sample obtained from the patient has been determined to have increased levels of somatic mutations in at least three-fourths or about 75% of the genes set forth in Table 1.

In any of the preceding methods, the somatic mutations in genes set forth in Table 1 have been determined to have increased by about 1% or more (e.g., about 2% or more, about 3% or more, about 4% or more, about 5% or more, about 6% or more, about 7% or more, about 8% or more, about 9% or more, about 10% or more, about 11% or more, about 12% or more, about 13% or more, about 14% or more, about 15% or more, about 20% or more, about 25% or more, about 30% or more, about 35% or more, about 40% or more, about 45% or more, about 50% or more, about 60% or more, about 65% or more, about 70% or more, about 75% or more, about 80% or more, about 85% or more, or about 90% or more) relative to reference levels of somatic mutations in the genes set forth in Table 1. For example, in some instances, the level of one or more somatic mutations was determined to have increased by about 1% or more. In some instances, the level of one or more somatic mutations was determined to have increased by about 5% or more. In other instances, the level of one or more somatic mutations was determined to have increased by about 10% or more. In some instances, the level of one or more somatic mutations was determined to have increased by about 15% or more. In yet other instances, the level of one or more somatic mutations was determined to have increased by about 20% or more. In further instances, the level of one or more somatic mutations was determined to have increased by about 25% or more. In some instances, the level of one or more somatic mutations was determined to have increased by about 30% or more. In some instances, the level of one or more somatic mutations was determined to have increased by about 35% or more. In some instances, the level of one or more somatic mutations was determined to have increased by about 40% or more. In some instances, the level of one or more somatic mutations was determined to have increased by about 50% or more. In other instances, about 1% or more (e.g., about 2% or more, about 3% or more, about 4% or more, about 5% or more, about 6% or more, about 7% or more, about 8% or more, about 9% or more, about 10% or more, about 11% or more, about 12% or more, about 13% or more, about 14% or more, about 15% or more, about 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, about 95% or more, or about 99% or more) of the genes set forth in Table 1 was determined to have increased somatic mutations. For example, in some instances, the tumor sample obtained from the patient has been determined to have increased levels of somatic mutations in at least one-half or about 50% of the genes set forth in Table 1. In some instances, the tumor sample obtained from the patient has been determined to have increased levels of somatic mutations in at least two-thirds or about 67% of the genes set forth in Table 1. In some instances, the tumor sample obtained from the patient has been determined to have increased levels of somatic mutations in at least three-fourths or about 75% of the genes set forth in Table 1.

In any of the preceding methods, the method may further include administering to the patient a therapeutically effective amount of a PD-L1 axis binding antagonist based on the level of somatic mutations in the tumor sample. The PD-L1 axis binding antagonist may be any PD-L1 axis binding antagonist known in the art or described herein, for example, in Section D, below.

For example, in some instances, the PD-L1 axis binding antagonist is selected from the group consisting of a PD-L1 binding antagonist, a PD-1 binding antagonist, and a PD-L2 binding antagonist. In some instances, the PD-L1 axis binding antagonist is a PD-L1 binding antagonist. In some instances, the PD-L1 binding antagonist inhibits the binding of PD-L1 to one or more of its ligand binding partners. In other instances, the PD-L1 binding antagonist inhibits the binding of PD-L1 to PD-1. In yet other instances, the PD-L1 binding antagonist inhibits the binding of PD-L1 to B7-1. In some instances, the PD-L1 binding antagonist inhibits the binding of PD-L1 to both PD-1 and B7-1. In some instances, the PD-L1 binding antagonist is an antibody. In some instances, the antibody is selected from the group consisting of: YW243.55.S70, MPDL3280A (atezolizumab), MDX-1105, MEDI4736 (durvalumab), and MSB0010718C (avelumab). In some instances, the antibody comprises a heavy chain comprising HVR-H1 sequence of SEQ ID NO:19, HVR-H2 sequence of SEQ ID NO:20, and HVR-H3 sequence of SEQ ID NO:21; and a light chain comprising HVR-L1 sequence of SEQ ID NO:22, HVR-L2 sequence of SEQ ID NO:23, and HVR-L3 sequence of SEQ ID NO:24.

In some instances, the antibody comprises a heavy chain variable region comprising the amino acid sequence of SEQ ID NO:26 and a light chain variable region comprising the amino acid sequence of SEQ ID NO:4.

In some instances, the PD-L1 axis binding antagonist is a PD-1 binding antagonist. For example, in some instances, the PD-1 binding antagonist inhibits the binding of PD-1 to one or more of its ligand binding partners. In some instances, the PD-1 binding antagonist inhibits the binding of PD-1 to PD-L1. In other instances, the PD-1 binding antagonist inhibits the binding of PD-1 to PD-L2. In yet other instances, the PD-1 binding antagonist inhibits the binding of PD-1 to both PD-L1 and PD-L2. In some instances, the PD-1 binding antagonist is an antibody. In some instances, the antibody is selected from the group consisting of: MDX 1106 (nivolumab), MK-3475 (pembrolizumab), CT-011 (pidilizumab), MEDI-0680 (AMP-514), PDR001, REGN2810, and BGB-108. In some instances, the PD-1 binding antagonist is an Fc-fusion protein. For example, in some instances, the Fc-fusion protein is AMP-224.

In some instances, the method further includes administering to the patient an effective amount of a second therapeutic agent. In some instances, the second therapeutic agent is selected from the group consisting of a cytotoxic agent, a growth-inhibitory agent, a radiation therapy agent, an anti-angiogenic agent, and combinations thereof.

In any of the preceding instances, the bladder cancer may be an urothelial bladder cancer, including but not limited to a non-muscle invasive urothelial bladder cancer, a muscle-invasive urothelial bladder cancer, or a metastatic urothelial bladder cancer.

The presence and/or levels (amount) of somatic mutations can be determined qualitatively and/or quantitatively based on any suitable criterion known in the art, including but not limited to DNA, mRNA, cDNA, proteins, protein fragments, and/or gene copy number.

In any of the preceding instances, the somatic mutations may be substitutions, deletions, and/or insertions.

In any of the preceding methods, the sample obtained from the patient is selected from the group consisting of tissue, whole blood, plasma, serum, and combinations thereof. In some instances, the sample is a tissue sample. In some instances, the tissue sample is a tumor sample. In some instances, the tumor sample comprises tumor-infiltrating immune cells, tumor cells, stromal cells, or any combinations thereof. In any of the preceding instances, the tumor sample may be a formalin-fixed and paraffin-embedded (FFPE) tumor sample, an archival tumor sample, a fresh tumor sample, or a frozen tumor sample.

In certain instances, the presence and/or levels (amount) of somatic mutations in a first sample is increased or elevated as compared to the presence/absence and/or levels (amount) of such somatic mutations in a second sample. In certain instances, the presence/absence and/or levels (amount) of somatic mutations in a first sample is decreased or reduced as compared to the presence and/or levels (amount) of such somatic mutations in a second sample. In certain instances, the second sample is a reference sample, reference cell, reference tissue, control sample, control cell, or control tissue. Additional disclosures for determining the presence/absence and/or levels (amount) of somatic mutations are described herein.

In certain instances, a reference sample, reference cell, reference tissue, control sample, control cell, or control tissue is a single sample or a combination of multiple samples from the same subject or individual that are obtained at one or more different time points than when the test sample is obtained. For example, a reference sample, reference cell, reference tissue, control sample, control cell, or control tissue is obtained at an earlier time point from the same subject or individual than when the test sample is obtained. Such reference sample, reference cell, reference tissue, control sample, control cell, or control tissue may be useful if the reference sample is obtained during initial diagnosis of cancer and the test sample is later obtained when the cancer becomes metastatic.

In certain instances, a reference sample, reference cell, reference tissue, control sample, control cell, or control tissue is a combination of multiple samples from one or more healthy individuals who are not the patient. In certain instances, a reference sample, reference cell, reference tissue, control sample, control cell, or control tissue is a combination of multiple samples from one or more individuals with a disease or disorder (e.g., cancer) who are not the subject or individual. In certain instances, a reference sample, reference cell, reference tissue, control sample, control cell, or control tissue is pooled RNA samples from normal tissues or pooled plasma or serum samples from one or more individuals who are not the patient. In certain instances, a reference sample, reference cell, reference tissue, control sample, control cell, or control tissue is pooled RNA samples from tumor tissues or pooled plasma or serum samples from one or more individuals with a disease or disorder (e.g., cancer) who are not the patient.

In some instances of any of the methods described herein, elevated or increased levels refers to an overall increase of about 10%, 20%, 30%, 40%, 50%, 60%, 70%, 80%, 90%, 95%, 96%, 97%, 98%, 99% or greater, in the level of somatic mutations, detected by standard art-known methods such as those described herein, as compared to a reference sample, reference cell, reference tissue, control sample, control cell, or control tissue. In certain instances, the elevated level refers to the increase in the level/amount of somatic mutations in the sample wherein the increase is at least about 1.5×, 1.75×, 2×, 3×, 4×, 5×, 6×, 7×, 8×, 9×, 10×, 25×, 50×, 75×, or 100× the level/amount of the respective somatic mutations in a reference sample, reference cell, reference tissue, control sample, control cell, or control tissue. In some instances, elevated level refers to an overall increase of greater than about 1.5-fold, about 1.75-fold, about 2-fold, about 2.25-fold, about 2.5-fold, about 2.75-fold, about 3.0-fold, or about 3.25 fold as compared to a reference sample, reference cell, reference tissue, control sample, control cell, or control tissue. In some instances, elevated or increased levels of somatic mutations refers to an overall increase in the levels of one or more classes of somatic mutations (e.g., point mutations, insertions and deletions (e.g., indels), amplifications, gene duplications, copy number alterations (CNAs), and rearrangements) and/or an overall increase in the level of a particular somatic mutation in a sample compared to a reference level.

In some instances of any of the methods described herein, reduced level refers to an overall reduction of about 10%, 20%, 30%, 40%, 50%, 60%, 70%, 80%, 90%, 95%, 96%, 97%, 98%, 99% or greater, in the level of somatic mutations, detected by standard art known methods such as those described herein, as compared to a reference sample, reference cell, reference tissue, control sample, control cell, or control tissue. In certain instances, reduced level refers to the decrease in level/amount of a somatic mutations in the sample wherein the decrease is at least about 0.9×, 0.8×, 0.7×, 0.6×, 0.5×, 0.4×, 0.3×, 0.2×, 0.1×, 0.05×, or 0.01× the level/amount of the respective somatic mutations in a reference sample, reference cell, reference tissue, control sample, control cell, or control tissue. In some instances reduced or decreased levels of somatic mutations refers to an overall decrease in the levels of one or more classes of somatic mutations (e.g., point mutations, insertions and deletions (e.g., indels), amplifications, gene duplications, copy number alterations (CNAs), and rearrangements) and/or an overall decrease in the level of a particular somatic mutation in a sample compared to a reference level.

B. Diagnostic Methods Based on the Level of Genes Rearranged in Cancer

Provided herein are methods that may be used individually or in combination with any of the preceding methods presented in Section A, above, for determining whether a patient suffering from a cancer (e.g., a bladder cancer (e.g., a UBC)) is likely to respond to treatment comprising a PD-L1 axis binding antagonist based on the level of rearrangement of any one of the genes listed in Table 2. For example, a rearrangement of one or more (e.g., 1, 2, 3, 4, 5, 6, 7, 8, 9, 10, 20, or more) of the genes listed in Table 2 can determine whether a patient suffering from a cancer (e.g., a bladder cancer (e.g., a UBC)) is likely to respond to treatment comprising a PD-L1 axis binding antagonist. In other instances, for example, an increase in the level of rearrangement of one or more (e.g., 1, 2, 3, 4, 5, 6, 7, 8, 9, 10, 20, or more) of the genes listed in Table 2 in combination with an increase in somatic mutation in 1 or more (e.g., 1, 2, 3, 4, 5, 6, 7, 8, 9, 10, 20, 30, 40, 50, 60, 70, 80, 90, 100, 150, 200, 250, 300 or more) genes listed in Table 1 can determine whether a patient suffering from a cancer (e.g., a bladder cancer (e.g., a UBC)) is likely to respond to treatment comprising a PD-L1 axis binding antagonist.

Also provided herein are methods that may be used individually or in combination with any of the preceding methods presented in Section A, above, for predicting responsiveness of a patient suffering from a cancer (e.g., a bladder cancer (e.g., an urothelial bladder cancer)) to treatment comprising a PD-L1 axis binding antagonist based on the level of rearrangement of any one of the genes listed in Table 2. For example, a rearrangement of one or more (e.g., 1, 2, 3, 4, 5, 6, 7, 8, 9, 10, 20, or more) of the genes listed in Table 2 can predict whether a patient suffering from a cancer (e.g., a bladder cancer (e.g., a UBC)) is likely to respond to treatment comprising a PD-L1 axis binding antagonist. In other instances, for example, an increase in the level of rearrangement of one or more (e.g., 1, 2, 3, 4, 5, 6, 7, 8, 9, 10, 20, or more) of the genes listed in Table 2 in combination with an increase in somatic mutation in 1 or more (e.g., 1, 2, 3, 4, 5, 6, 7, 8, 9, 10, 20, 30, 40, 50, 60, 70, 80, 90, 100, 150, 200, 250, 300 or more) genes listed in Table 1 can predict whether a patient suffering from a cancer (e.g., a bladder cancer (e.g., a UBC)) is likely to respond to treatment comprising a PD-L1 axis binding antagonist. Any of the methods may further include administering to the patient a PD-L1 axis binding antagonist (for example, as described in Section D, below) to the patient. Any of the methods may further include administering an effective amount of a second therapeutic agent to the patient.

The invention provides a method for treating a patient suffering from a bladder cancer, the method comprising administering to the patient a therapeutically effective amount of a PD-L1 axis binding antagonist, wherein the tumor sample obtained from the patient has been determined to have an increased level of a rearrangement in at least one or more (e.g., 1, 2, 3, 4, 5, 6, 7, 8, 9, 10, 20, or more) genes set forth in Table 2 relative to a reference level of rearrangement in the at least one gene set forth in Table 2. In other instances, about 1% or more (e.g., about 2% or more, about 3% or more, about 4% or more, about 5% or more, about 6% or more, about 7% or more, about 8% or more, about 9% or more, about 10% or more, about 11% or more, about 12% or more, about 13% or more, about 14% or more, about 15% or more, about 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, about 95% or more, or about 99% or more) of the genes set forth in Table 2 was determined to have increased level of rearrangement. For example, in some instances, the tumor sample obtained from the patient has been determined to have increased levels of rearrangement in at least one-half or about 50% of the genes set forth in Table 2. In some instances, the tumor sample obtained from the patient has been determined to have increased levels of rearrangement in at least two-thirds or about 67% of the genes set forth in Table 2. In some instances, the tumor sample obtained from the patient has been determined to have increased levels of rearrangement in at least three-fourths or about 75% of the genes set forth in Table 2. In some instances, in combination with an elevated level of a rearrangement in any gene listed in Table 2, at least one or more (e.g., 1, 2, 3, 4, 5, 6, 7, 8, 9, 10, 20, 30, 40, 50, 60, 70, 80, 90, 100, 150, 200, 250, 300 or more) genes as set forth in Table 1 has been determined to have an increased level of somatic mutations relative to a reference level of somatic mutations in the at least one gene set forth in Table 1.

TABLE 2

| Genes Rearranged in Cancer | | | | | | | | | |
|---|---|---|---|---|---|---|---|---|---|
| ALK | BRAF | BRD4 | ETV4 | FGFR1 | KIT | MYC | NTRK2 | RARA | TMPRSS2 |
| BCL2 | BRCA1 | EGFR | ETV5 | FGFR2 | MSH2 | NOTCH2 | PDGFRA | RET | |
| BCR | BRCA2 | ETV1 | ETV6 | FGFR3 | MYB | NTRK1 | RAF1 | ROS1 | |

The presence and/or levels (amount) of somatic mutations can be determined qualitatively and/or quantitatively based on any suitable criterion known in the art, including but not limited to the measurement of DNA, mRNA, cDNA, proteins, protein fragments, and/or gene copy number levels in an individual. In some instances, a comprehensive genomic profile of an individual is determined. In some instances, a comprehensive genomic profile of a sample (e.g., tissue sample, formalin-fixed, paraffin-embedded (FFPE) tissues sample, core or fine needle biopsies) collected from an individual is determined. In some instances, the determination of the genomic profile comprises applying next-generation sequencing methods, known in the art or described herein, to identify genomic alterations (e.g., somatic mutations (e.g., base substitutions, insertions and deletions (indels), copy number alterations (CNAs) and rearrangements)) known to be unambiguous drivers of cancer (e.g., solid tumors). In some instances, the test simultaneously sequences the coding region of 315 cancer-related genes plus introns from 28 genes often rearranged in cancer to a typical median depth of coverage of greater than 500×. In some instances, each covered sequencing read represents a unique DNA fragment to enable the highly sensitive and specific detection of genomic alterations that occur at low frequencies due to tumor heterogeneity, low tumor purity and small tissue samples.

The invention provides a method for determining whether a patient suffering from a bladder cancer is likely to respond to treatment comprising a PD-L1 axis binding antagonist, the method comprising determining the level of rearrangement in a tumor sample obtained from the patient, wherein an increased level of a rearrangement in at least one or more (e.g., 1, 2, 3, 4, 5, 6, 7, 8, 9, 10, 20, or more) genes as set forth in Table 2 of the tumor sample indicates that the patient is likely to respond to treatment comprising a PD-L1 axis binding antagonist. For example, in some instances, an increased level of rearrangement in at least about one-third of the genes set forth in Table 2 in a tumor sample indicates that the patient is likely to respond to treatment comprising a PD-L1 axis binding antagonist. In other instances, an increased level of rearrangement in at least about two-thirds of the genes set forth in Table 2 in a tumor sample indicates that the patient is likely to respond to treatment comprising a PD-L1 axis binding antagonist. In other instances, an increased level of rearrangement in at least about three-fourths of the genes set forth in Table 2 in a tumor sample indicates that the patient is likely to respond to treatment comprising a PD-L1 axis binding antagonist. In other instances, about 1% or more (e.g., about 2% or more, about 3% or more, about 4% or more, about 5% or more, about 6% or more, about 7% or more, about 8% or more, about 9% or more. about 10% or more, about 11% or more, about 12% or more, about 13% or more, about 14% or more, about 15% or more, about 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, about 95% or more, or about 99% or more) of the genes set forth in Table 2 was determined to have increased rearrangements. For example, in some instances, the tumor sample obtained from the patient has been determined to have increased levels of rearrangements in at least one-half or about 50% of the genes set forth in Table 2. In some instances, the tumor sample obtained from the patient has been determined to have increased levels of rearrangements in at least two-thirds or about 67% of the genes set forth in Table 2. In some instances, the tumor sample obtained from the patient has been determined to have increased levels of rearrangements in at least three-fourths or about 75% of the genes set forth in Table 2. In some instances, in combination with an elevated level of a somatic mutation in any gene listed in Table 2, at least one or more (e.g., 1, 2, 3, 4, 5, 6, 7, 8, 9, 10, 20, 30, 40, 50, 60, 70, 80, 90, 100, 150, 200, 250, 300 or more) genes as set forth in Table 1 has been determined to have an increased level of somatic mutations relative to a reference level of somatic mutations in the at least one gene set forth in Table 1.

The invention further provides a method for predicting responsiveness of a patient suffering from a bladder cancer to treatment comprising a PD-L1 axis binding antagonist, the method comprising determining the level of rearrangement in a tumor sample obtained from the patient, wherein an increased level of rearrangement in at least one or more (e.g., 1, 2, 3, 4, 5, 6, 7, 8, 9, 10, 20 or more) genes as set forth in Table 2 of the tumor sample indicates that the patient is likely to respond to treatment comprising a PD-L1 axis binding antagonist. For example, in some instances, an increased level of rearrangement in one-third of the genes set forth in Table 2 in a tumor sample indicates that the patient is likely to respond to treatment comprising a PD-L1 axis binding antagonist. In other instances, an increased level of rearrangement in two-thirds of the genes set forth in Table 2 in a tumor sample indicates that the patient is likely to respond to treatment comprising a PD-L1 axis binding antagonist. In other instances, an increased level of rearrangement in three-fourths of the genes set forth in Table 2 in a tumor sample indicates that the patient is likely to respond to treatment comprising a PD-L1 axis binding antagonist. In other instances, about 1% or more (e.g., about 2% or more, about 3% or more, about 4% or more, about 5% or more, about 6% or more, about 7% or more, about 8% or more, about 9% or more, about 10% or more, about 11% or more, about 12% or more, about 13% or more, about 14% or more, about 15% or more, about 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, about 95% or more, or about 99% or more) of the genes set forth in Table 2 was determined to have increased rearrangements. For example, in some instances, the tumor sample obtained from the patient has been determined to have increased levels of rearrangements in at least one-half or about 50% of the genes set forth in Table 2. In some instances, the tumor sample obtained from the patient has been determined to have increased levels of rearrangements in at least two-thirds or about 67% of the genes set forth in Table 2. In some instances, the tumor sample obtained from the patient has been determined to have increased levels of rearrangements in at least three-fourths or about 75% of the genes set forth in Table 2. In some instances, in combination with an elevated level of rearrangements in any gene listed in Table 2, at least one or more (e.g., 1, 2, 3, 4, 5, 6, 7, 8, 9, 10, 20, 30, 40, 50, 60, 70, 80, 90, 100, 150, 200, 250, 300 or more) genes as set forth in Table 1 has been determined to have an increased level of somatic mutations relative to a reference level of somatic mutations in the at least one gene set forth in Table 1.

The invention yet also provides a method for selecting a therapy for a patient suffering from a bladder cancer, the method comprising determining the level of rearrangements in a tumor sample obtained from the patient, wherein an increased level of a rearrangement in at least one or more (e.g., 1, 2, 3, 4, 5, 6, 7, 8, 9, 10, 20, or more) genes as set forth in Table 2 of the tumor sample indicates that the patient is likely to respond to treatment comprising a PD-L1 axis binding antagonist. For example, in some instances, an increased level of rearrangement in one-third of the genes set forth in Table 2 in a tumor sample indicates that the patient is likely to respond to treatment comprising a PD-L1 axis binding antagonist. In other instances, an increased level of rearrangement in two-thirds of the genes set forth in Table 2 in a tumor sample indicates that the patient is likely to respond to treatment comprising a PD-L1 axis binding antagonist. In other instances, an increased level of rearrangement in three-fourths of the genes set forth in Table 2 in a tumor sample indicates that the patient is likely to respond to treatment comprising a PD-L1 axis binding antagonist. In other instances, about 1% or more (e.g., about 2% or more, about 3% or more, about 4% or more, about 5% or more, about 6% or more, about 7% or more, about 8% or more, about 9% or more, about 10% or more, about 11% or more, about 12% or more, about 13% or more, about 14% or more, about 15% or more, about 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, about 95% or more, or about 99% or more) of the genes set forth in Table 2 was determined to have increased rearrangements. For example, in some instances, the tumor sample obtained from the patient has been determined to have increased levels of rearrangement in at least one-half or about 50% of the genes set forth in Table 2. In some instances, the tumor sample obtained from the patient has been determined to have increased levels of rearrangement in at least two-thirds or about 67% of the genes set forth in Table 2. In some instances, the tumor sample obtained from the patient has been determined to have increased levels of rearrangements in at least three-fourths or about 75% of the genes set forth in Table 2. In some instances, in combination with an elevated level of a rearrangement in any gene listed in Table 2, at least one or more (e.g., 1, 2, 3, 4, 5, 6, 7, 8, 9, 10, 20, 30, 40, 50, 60, 70, 80, 90, 100, 150, 200, 250, 300 or more) genes as set forth in Table 1 has been determined to have an increased level of somatic mutations relative to a reference level of somatic mutations in the at least one gene set forth in Table 1.

In any of the preceding methods, the rearrangements in genes set forth in Table 2 have been determined to have increased by about 1% or more (e.g., about 2% or more, about 3% or more, about 4% or more, about 5% or more, about 6% or more, about 7% or more, about 8% or more, about 9% or more, about 10% or more, about 11% or more, about 12% or more, about 13% or more, about 14% or more, about 15% or more, about 20% or more, about 25% or more, about 30% or more, about 35% or more, about 40% or more, about 45% or more, about 50% or more, about 60% or more, about 65% or more, about 70% or more, about 75% or more, about 80% or more, about 85% or more, or about 90% or more) relative to reference levels of rearrangements in the genes set forth in Table 2. For example, in some instances, the level of one or more rearrangements was determined to have increased by about 1% or more. In some instances, the level of one or more rearrangements was determined to have increased by about 5% or more. In other instances, the level of one or more rearrangements was determined to have increased by about 10% or more. In some instances, the level of one or more rearrangements was determined to have increased by about 15% or more. In yet other instances, the level of one or more rearrangements was determined to have increased by about 20% or more. In further instances, the level of one or more rearrangements was determined to have increased by about 25% or more. In some instances, the level of one or more rearrangements was determined to have increased by about 30% or more. In some instances, the level of one or more rearrangements was determined to have increased by about 35% or more. In some instances, the level of one or more rearrangements was determined to have increased by about 40% or more. In some instances, the level of one or more rearrangements was determined to have increased by about 50% or more. In other instances, about 1% or more (e.g., about 2% or more, about 3% or more, about 4% or more, about 5% or more, about 6% or more, about 7% or more, about 8% or more, about 9% or more, about 10% or more, about 11% or more, about 12% or more, about 13% or more, about 14% or more, about 15% or more, about 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, about 95% or more, or about 99% or more) of the genes set forth in Table 2 was determined to have increased rearrangements. For example, in some instances, the tumor sample obtained from the patient has been determined to have increased levels of rearrangements in at least one-half or about 50% of the genes set forth in Table 2. In some instances, the tumor sample obtained from the patient has been determined to have increased levels of rearrangements in at least two-thirds or about 67% of the genes set forth in Table 2. In some instances, the tumor sample obtained from the patient has been determined to have increased levels of rearrangements in at least three-fourths or about 75% of the genes set forth in Table 2. In some instances, in combination with an elevated level of a rearrangement in any gene listed in Table 2, at least one or more (e.g., 1, 2, 3, 4, 5, 6, 7, 8, 9, 10, 20, 30, 40, 50, 60, 70, 80, 90, 100, 150, 200, 250, 300 or more) genes as set forth in Table 1 has been determined to have an increased level of somatic mutations relative to a reference level of somatic mutations in the at least one gene set forth in Table 1.

In any of the preceding methods, the method may further include administering to the patient a therapeutically effective amount of a PD-L1 axis binding antagonist based on the level of somatic mutations in the tumor sample. The PD-L1 axis binding antagonist may be any PD-L1 axis binding antagonist known in the art or described herein, for example, in Section D, below.

For example, in some instances, the PD-L1 axis binding antagonist is selected from the group consisting of a PD-L1 binding antagonist, a PD-1 binding antagonist, and a PD-L2 binding antagonist. In some instances, the PD-L1 axis binding antagonist is a PD-L1 binding antagonist. In some instances, the PD-L1 binding antagonist inhibits the binding of PD-L1 to one or more of its ligand binding partners. In other instances, the PD-L1 binding antagonist inhibits the binding of PD-L1 to PD-1. In yet other instances, the PD-L1 binding antagonist inhibits the binding of PD-L1 to B7-1. In some instances, the PD-L1 binding antagonist inhibits the binding of PD-L1 to both PD-1 and B7-1. In some instances, the PD-L1 binding antagonist is an antibody. In some instances, the antibody is selected from the group consisting of: YW243.55.S70, MPDL3280A (atezolizumab), MDX-1105, MED14736 (durvalumab), and MSB0010718C (avelumab). In some instances, the antibody comprises a heavy chain comprising HVR-H1 sequence of SEQ ID NO:19, HVR-H2 sequence of SEQ ID NO:20, and HVR-H3 sequence of SEQ ID NO:21; and a light chain comprising HVR-L1 sequence of SEQ ID NO:22, HVR-L2 sequence of SEQ ID NO:23, and HVR-L3 sequence of SEQ ID NO:24. In some instances, the antibody comprises a heavy chain variable region comprising the amino acid sequence of SEQ ID NO:26 and a light chain variable region comprising the amino acid sequence of SEQ ID NO:4.

In some instances, the PD-L1 axis binding antagonist is a PD-1 binding antagonist. For example, in some instances, the PD-1 binding antagonist inhibits the binding of PD-1 to one or more of its ligand binding partners. In some instances, the PD-1 binding antagonist inhibits the binding of PD-1 to PD-L1. In other instances, the PD-1 binding antagonist inhibits the binding of PD-1 to PD-L2. In yet other instances, the PD-1 binding antagonist inhibits the binding of PD-1 to both PD-L1 and PD-L2. In some instances, the PD-1 binding antagonist is an antibody. In some instances, the antibody is selected from the group consisting of: MDX 1106 (nivolumab), MK-3475 (pembrolizumab), CT-011 (pidilizumab), MEDI-0680 (AMP-514), PDR001, REGN2810, and BGB-108. In some instances, the PD-1 binding antagonist is an Fc-fusion protein. For example, in some instances, the Fc-fusion protein is AMP-224.

In some instances, the method further includes administering to the patient an effective amount of a second therapeutic agent. In some instances, the second therapeutic agent is selected from the group consisting of a cytotoxic agent, a growth-inhibitory agent, a radiation therapy agent, an anti-angiogenic agent, and combinations thereof.

In any of the preceding instances, the bladder cancer may be an urothelial bladder cancer, including but not limited to a non-muscle invasive urothelial bladder cancer, a muscle-invasive urothelial bladder cancer, or a metastatic urothelial bladder cancer.

In any of the preceding instances, the presence and/or levels (amount) of somatic mutations can be determined qualitatively and/or quantitatively based on any suitable criterion known in the art, including but not limited to DNA, mRNA, cDNA, proteins, protein fragments, and/or gene copy number.

In any of the preceding instances, the somatic mutations may be substitutions, deletions, and/or insertions. For example, in some instances, the somatic mutations may be copy number alterations and/or rearrangements.

In any of the preceding methods, the sample obtained from the patient is selected from the group consisting of tissue, whole blood, plasma, serum, and combinations thereof. In some instances, the sample is a tissue sample. In some instances, the tissue sample is a tumor sample. In some instances, the tumor sample comprises tumor-infiltrating immune cells, tumor cells, stromal cells, or any combinations thereof. In any of the preceding instances, the tumor sample may be a formalin-fixed and paraffin-embedded (FFPE) tumor sample, an archival tumor sample, a fresh tumor sample, or a frozen tumor sample.

In certain instances, the presence and/or levels (amount) of somatic mutations in a first sample is increased or elevated as compared to the presence/absence and/or level (amount) of such somatic mutations in a second sample. In certain instances, the presence/absence and/or levels (amount) of somatic mutation in a first sample is decreased or reduced as compared to the presence and/or levels (amount) in a second sample. In certain instances, the second sample is a reference sample, reference cell, reference tissue, control sample, control cell, or control tissue. Additional disclosures for determining the presence/absence and/or levels (amount) of somatic mutations are described herein.

In certain instances, a reference sample, reference cell, reference tissue, control sample, control cell, or control tissue is a single sample or a combination of multiple samples from the same subject or individual that are obtained at one or more different time points than when the test sample is obtained. For example, a reference sample, reference cell, reference tissue, control sample, control cell, or control tissue is obtained at an earlier time point from the same subject or individual than when the test sample is obtained. Such reference sample, reference cell, reference tissue, control sample, control cell, or control tissue may be useful if the reference sample is obtained during initial diagnosis of cancer and the test sample is later obtained when the cancer becomes metastatic.

In certain instances, a reference sample, reference cell, reference tissue, control sample, control cell, or control tissue is a combination of multiple samples from one or more healthy individuals who are not the patient. In certain instances, a reference sample, reference cell, reference tissue, control sample, control cell, or control tissue is a combination of multiple samples from one or more individuals with a disease or disorder (e.g., cancer) who are not the subject or individual. In certain instances, a reference sample, reference cell, reference tissue, control sample, control cell, or control tissue is pooled RNA samples from normal tissues or pooled plasma or serum samples from one or more individuals who are not the patient. In certain instances, a reference sample, reference cell, reference tissue, control sample, control cell, or control tissue is pooled RNA samples from tumor tissues or pooled plasma or serum samples from one or more individuals with a disease or disorder (e.g., cancer) who are not the patient.

In some instances of any of the methods described herein, elevated or increased levels refers to an overall increase of about 10%, 20%, 30%, 40%, 50%, 60%, 70%, 80%, 90%, 95%, 96%, 97%, 98%, 99% or greater, in the level of somatic mutations, detected by standard art-known methods such as those described herein, as compared to a reference sample, reference cell, reference tissue, control sample, control cell, or control tissue. In certain instances, the elevated level refers to the increase in the level/amount of somatic mutations in the sample wherein the increase is at least about 1.5×, 1.75×, 2×, 3×, 4×, 5×, 6×, 7×, 8×, 9×, 10×, 25×, 50×, 75×, or 100× the level/amount of the respective somatic mutations in a reference sample, reference cell, reference tissue, control sample, control cell, or control tissue. In some instances, elevated level refers to an overall increase of greater than about 1.5-fold, about 1.75-fold, about 2-fold, about 2.25-fold, about 2.5-fold, about 2.75-fold, about 3.0-fold, or about 3.25-fold as compared to a reference sample, reference cell, reference tissue, control sample, control cell, or control tissue. In some instances, elevated or increased levels of somatic mutations refers to an overall increase in the levels of one or more classes of somatic mutations (e.g., point mutations, insertions and deletions (e.g., indels), amplifications, gene duplications, copy number alterations (CNAs), and rearrangements) and/or an overall increase in the level of a particular somatic mutation in a sample compared to a reference level.

In some instances of any of the methods described herein, reduced level refers to an overall reduction of about 10%, 20%, 30%, 40%, 50%, 60%, 70%, 80%, 90%, 95%, 96%, 97%, 98%, 99% or greater, in the level of somatic mutations, detected by standard art known methods such as those described herein, as compared to a reference sample, reference cell, reference tissue, control sample, control cell, or control tissue. In certain instances, reduced level refers to the decrease in level/amount of somatic mutations in the sample wherein the decrease is at least about 0.9×, 0.8×, 0.7×, 0.6×, 0.5×, 0.4×, 0.3×, 0.2×, 0.1×, 0.05×, or 0.01× the level/amount of the respective somatic mutations in a reference sample, reference cell, reference tissue, control sample, control cell, or control tissue. In some instances reduced or decreased levels of somatic mutations refers to an overall decrease in the levels of one or more classes of somatic mutations (e.g., point mutations, insertions and deletions (e.g., indels), amplifications, gene duplications, copy number alterations (CNAs), and rearrangements) and/ or an overall decrease in the level of a particular somatic mutation in a sample compared to a reference level.

C. Therapeutic Methods

The present invention provides methods for treating a patient suffering from a cancer (e.g., a bladder cancer (e.g., a UBC). In some instances, the UBC is a 1 L UBC. In other embodiments, the UBC is a muscle invasive UBC. In other instances, the UBC is a non-muscle invasive UBC. In some instances, the patient has progressed following treatment with a platinum-containing therapy (e.g., a platinum-based chemotherapeutic agent, e.g., a cisplatin-based chemotherapy). In other instances, the patient may be ineligible for treatment with a platinum-containing therapy (e.g., a platinum-based chemotherapeutic agent, e.g., a cisplatin-based chemotherapy) and has not received prior treatment, e.g., prior treatment for locally advanced or metastatic urothelial bladder cancer. In other instances, the patient is undergoing treatment for a UBC in the adjuvant setting (i.e., post-surgical setting). In some instances, the methods of the invention include administering to the patient an anti-cancer therapy that includes a PD-L1 axis binding antagonist. Any of the PD-L1 axis binding antagonists described herein (see, for example, Section D, below) or known in the art may used in the methods. In some instances, the methods involve determining the presence and/or level of somatic mutations in a sample (for example, in a tumor sample) obtained from a patient and administering an anti-cancer therapy to the patient based on the presence and/or expression of somatic mutations in the sample, for example, using any of the methods described herein (for example, those described in Section A and in Section B or in the Examples below) or known in the art.

The invention provides a method of treating a patient suffering from a bladder cancer, the method comprising administering to the patient a therapeutically effective amount of a PD-L1 axis binding antagonist, wherein a tumor sample obtained from the patient has been determined to have increased levels of somatic mutation in at least one gene set forth in Table 1 and/or Table 2 relative to reference level of somatic mutation in the at least one gene set forth in Table 1 and/or Table 2.

In any of the preceding methods, the somatic mutations in genes set forth in Table 1 and/or Table 2 have been determined to have increased by about 1% or more (e.g., about 2% or more, about 3% or more, about 4% or more, about 5% or more, about 6% or more, about 7% or more, about 8% or more, about 9% or more, about 10% or more, about 11% or more, about 12% or more, about 13% or more, about 14% or more, about 15% or more, about 20% or more, about 25% or more, about 30% or more, about 35% or more, about 40% or more, about 45% or more, about 50% or more, about 60% or more, about 65% or more, about 70% or more, about 75% or more, about 80% or more, about 85% or more, or about 90% or more) relative to reference levels of somatic mutations in the genes set forth in Table 1 and/or Table 2. For example, in some instances, the level of one or more somatic mutations (e.g., the level of one or more somatic mutations from different classes (e.g., insertions, deletions, and/or rearrangements), the level of a particular class of somatic mutations, and/or the level of a particular somatic mutation) was determined to have increased by about 1% or more. In some instances, the level of one or more somatic mutations was determined to have increased by about 5% or more. In other instances, the level of one or more somatic mutations was determined to have increased by about 10% or more. In some instances, the level of one or more somatic mutations was determined to have increased by about 15% or more. In yet other instances, the level of one or more somatic mutations was determined to have increased by about 20% or more. In further instances, the level of one or more somatic mutations was determined to have increased by about 25% or more. In some instances, the level of one or more somatic mutations was determined to have increased by about 30% or more. In some instances, the level of one or more somatic mutations was determined to have increased by about 35% or more. In some instances, the level of one or more somatic mutations was determined to have increased by about 40% or more. In some instances, the level of one or more somatic mutations was determined to have increased by about 50% or more.

In any of the preceding methods, about 1% or more (e.g., about 2% or more, about 3% or more, about 4% or more, about 5% or more, about 6% or more, about 7% or more, about 8% or more, about 9% or more, about 10% or more, about 11% or more, about 12% or more, about 13% or more, about 14% or more, about 15% or more, about 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, about 95% or more, or about 99% or more) of the genes set forth in Table 1 and/or Table 2 was determined to have increased somatic mutations. For example, in some instances, the tumor sample obtained from the patient has been determined to have increased levels of somatic mutations in at least one-half or about 50% of the genes set forth in Table 1 and/or Table 2. In some instances, the tumor sample obtained from the patient has been determined to have increased levels of somatic mutations in at least two-thirds or about 67% of the genes set forth in Table 1 and/or Table 2. In some instances, the tumor sample obtained from the patient has been determined to have increased levels of somatic mutations in at least three-fourths or about 75% of the genes set forth in Table 1 and/or Table 2.

In any of the preceding methods, an estimate of mutation load, reflecting the level of somatic mutations and/or rearrangements detected in the genes listed in Table 1 and/or Table 2, which has been (or is) determined to be at least about 7 mutations/megabase (Mb) or more (e.g., about 8 mutations/Mb or more, about 9 mutations/Mb or more, about 10 mutations/Mb or more, about 11 mutations/Mb or more, about 12 mutations/Mb or more, about 13 mutations/Mb or more, about 14 mutations/Mb or more, about 15 mutations/Mb or more, about 16 mutations/Mb or more, about 17 mutations/Mb or more, about 18 mutations/Mb or more, about 19 mutations/Mb or more, about 20 mutations/Mb or more, about 25 mutations/Mb or more, about 30 mutations/Mb or more, about 35 mutations/Mb or more, about 40 mutations/Mb or more, and about 50 mutations/Mb or more) is predictive of responsiveness to treatment (e.g., treatment including a PD-L1 axis binding antagonist). In some instances, a mutation load that is predictive of responsiveness to treatment (e.g., treatment including a PD-L1 axis binding antagonist) may be between about 7 mutations/Mb to about 20 mutations/Mb. In some instances, a mutation load that is predictive of responsiveness to treatment may be between about 10 mutations/Mb to about 15 mutations/Mb. In some instances, a mutation load that is predictive of responsiveness to treatment may be between about 11 mutations/Mb to about 13 mutations/Mb. In some instances, a mutation load that is predictive of responsiveness to treatment may be about 12.5 mutations/Mb.

In any of the preceding methods, the PD-L1 axis binding antagonist may be any PD-L1 axis binding antagonist known in the art or described herein, for example, in Section D, below.

For example, in some instances, the PD-L1 axis binding antagonist is selected from the group consisting of a PD-L1 binding antagonist, a PD-1 binding antagonist, and a PD-L2 binding antagonist. In some instances, the PD-L1 axis binding antagonist is a PD-L1 binding antagonist. In some instances, the PD-L1 binding antagonist inhibits the binding of PD-L1 to one or more of its ligand binding partners. In other instances, the PD-L1 binding antagonist inhibits the binding of PD-L1 to PD-1. In yet other instances, the PD-L1 binding antagonist inhibits the binding of PD-L1 to B7-1. In some instances, the PD-L1 binding antagonist inhibits the binding of PD-L1 to both PD-1 and B7-1. In some instances, the PD-L1 binding antagonist is an antibody. In some instances, the antibody is selected from the group consisting of: YW243.55.S70, MPDL3280A (atezolizumab), MDX-1105, MEDI4736 (durvalumab), and MSB0010718C (avelumab). In some instances, the antibody comprises a heavy chain comprising HVR-H1 sequence of SEQ ID NO:19, HVR-H2 sequence of SEQ ID NO:20, and HVR-H3 sequence of SEQ ID NO:21; and a light chain comprising HVR-L1 sequence of SEQ ID NO:22, HVR-L2 sequence of SEQ ID NO:23, and HVR-L3 sequence of SEQ ID NO:24. In some instances, the antibody comprises a heavy chain variable region comprising the amino acid sequence of SEQ ID NO:26 and a light chain variable region comprising the amino acid sequence of SEQ ID NO:4.

In some instances, the PD-L1 axis binding antagonist is a PD-1 binding antagonist. For example, in some instances, the PD-1 binding antagonist inhibits the binding of PD-1 to one or more of its ligand binding partners. In some instances, the PD-1 binding antagonist inhibits the binding of PD-1 to PD-L1. In other instances, the PD-1 binding antagonist inhibits the binding of PD-1 to PD-L2. In yet other instances, the PD-1 binding antagonist inhibits the binding of PD-1 to both PD-L1 and PD-L2. In some instances, the PD-1 binding antagonist is an antibody. In some instances, the antibody is selected from the group consisting of: MDX 1106 (nivolumab), MK-3475 (pembrolizumab), CT-011 (pidilizumab), MEDI-0680 (AMP-514), PDR001, REGN2810, and BGB-108. In some instances, the PD-1 binding antagonist is an Fc-fusion protein. For example, in some instances, the Fc-fusion protein is AMP-224.

In some instances, the method further includes administering to the patient an effective amount of a second therapeutic agent. In some instances, the second therapeutic agent is selected from the group consisting of a cytotoxic agent, a growth-inhibitory agent, a radiation therapy agent, an anti-angiogenic agent, and combinations thereof. In some instances, the second therapeutic agent is an agonist directed against an activating co-stimulatory molecule. In some instances, the second therapeutic agent is an antagonist directed against an inhibitory co-stimulatory molecule.

In any of the preceding instances, the urothelial bladder cancer may be, for example, a non-muscle invasive urothelial bladder cancer, a muscle-invasive urothelial bladder cancer, or metastatic urothelial bladder cancer.

In a further aspect, the invention provides for the use of a PD-L1 axis binding antagonist in the manufacture or preparation of a medicament. In one instance, the medicament is for treatment of a cancer. In a further instance, the medicament is for use in a method of treating a cancer comprising administering to a patient suffering from a cancer (e.g., a bladder cancer (e.g., an urothelial bladder cancer)) an effective amount of the medicament. In one such instance, the method further comprises administering to the individual an effective amount of at least one additional therapeutic agent, e.g., as described below.

The compositions utilized in the methods described herein (e.g., PD-L1 axis binding antagonists) can be administered by any suitable method, including, for example, intravenously, intramuscularly, subcutaneously, intradermally, percutaneously, intraarterially, intraperitoneally, intralesionally, intracranially, intraarticularly, intraprostatically, intrapleurally, intratracheally, intrathecally, intranasally, intravaginally, intrarectally, topically, intratumorally, peritoneally, subconjunctivally, intravesicularly, mucosally, intrapericardially, intraumbilically, intraocularly, intraorbitally, orally, topically, transdermally, intravitreally (e.g., by intravitreal injection), by eye drop, by inhalation, by injection, by implantation, by infusion, by continuous infusion, by localized perfusion bathing target cells directly, by catheter, by lavage, in cremes, or in lipid compositions. The compositions utilized in the methods described herein can also be administered systemically or locally. The method of administration can vary depending on various factors (e.g., the compound or composition being administered and the severity of the condition, disease, or disorder being treated). In some instances, the PD-L1 axis binding antagonist is administered intravenously, intramuscularly, subcutaneously, topically, orally, transdermally, intraperitoneally, intraorbitally, by implantation, by inhalation, intrathecally, intraventricularly, or intranasally. Dosing can be by any suitable route, e.g., by injections, such as intravenous or subcutaneous injections, depending in part on whether the administration is brief or chronic. Various dosing schedules including but not limited to single or multiple administrations over various time-points, bolus administration, and pulse infusion are contemplated herein.

PD-L1 axis binding antagonists (e.g., an antibody, binding polypeptide, and/or small molecule) described herein (any additional therapeutic agent) may be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The PD-L1 axis binding antagonist need not be, but is optionally formulated with and/or administered concurrently with one or more agents currently used to prevent or treat the disorder in question. The effective amount of such other agents depends on the amount of the PD-L1 axis binding antagonist present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of a cancer (e.g., a bladder cancer (e.g., an urothelial bladder cancer)), the appropriate dosage of a PD-L1 axis binding antagonist described herein (when used alone or in combination with one or more other additional therapeutic agents) will depend on the type of disease to be treated, the severity and course of the disease, whether the PD-L1 axis binding antagonist is administered for preventive or therapeutic purposes, previous therapy, the patient's clinical history and response to the PD-L1 axis binding antagonist, and the discretion of the attending physician. The PD-L1 axis binding antagonist is suitably administered to the patient at one time or over a series of treatments. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. Such doses may be administered intermittently, e.g., every week or every three weeks (e.g., such that the patient receives, for example, from about two to about twenty, or e.g., about six doses of the PD-L1 axis binding antagonist). An initial higher loading dose, followed by one or more lower doses may be administered. However, other dosage regimens may be useful. The progress of this therapy is easily monitored by conventional techniques and assays.

For example, as a general proposition, the therapeutically effective amount of a PD-L1 axis binding antagonist antibody administered to human will be in the range of about 0.01 to about 50 mg/kg of patient body weight, whether by one or more administrations. In some instances, the antibody used is about 0.01 mg/kg to about 45 mg/kg, about 0.01 mg/kg to about 40 mg/kg, about 0.01 mg/kg to about 35 mg/kg, about 0.01 mg/kg to about 30 mg/kg, about 0.01 mg/kg to about 25 mg/kg, about 0.01 mg/kg to about 20 mg/kg, about 0.01 mg/kg to about 15 mg/kg, about 0.01 mg/kg to about 10 mg/kg, about 0.01 mg/kg to about 5 mg/kg, or about 0.01 mg/kg to about 1 mg/kg administered daily, weekly, every two weeks, every three weeks, or monthly, for example. In some instances, the antibody is administered at 15 mg/kg. However, other dosage regimens may be useful. In one instance, an anti-PD-L1 antibody described herein is administered to a human at a dose of about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, or about 1800 mg on day 1 of 21-day cycles (every three weeks, q3w). In some instances, anti-PD-L1 antibody MPDL3280A is administered at 1200 mg intravenously every three weeks (q3w). The dose may be administered as a single dose or as multiple doses (e.g., 2 or 3 doses), such as infusions. The dose of the antibody administered in a combination treatment may be reduced as compared to a single treatment. The progress of this therapy is easily monitored by conventional techniques.

In some instances, the methods further involve administering to the patient an effective amount of a second therapeutic agent. In some instances, the second therapeutic agent is selected from the group consisting of a cytotoxic agent, a chemotherapeutic agent, a growth-inhibitory agent, a radiation therapy agent, an anti-angiogenic agent, and combinations thereof. In some instances, a PD-L1 axis binding antagonist may be administered in conjunction with a chemotherapy or chemotherapeutic agent. In some instances, a PD-L1 axis binding antagonist may be administered in conjunction with a radiation therapy agent. In some instances, a PD-L1 axis binding antagonist may be administered in conjunction with a targeted therapy or targeted therapeutic agent. In some instances, a PD-L1 axis binding antagonist may be administered in conjunction with an immunotherapy or immunotherapeutic agent, for example a monoclonal antibody. In some instances, the second therapeutic agent is an agonist directed against an activating co-stimulatory molecule. In some instances, the second therapeutic agent is an antagonist directed against an inhibitory co-stimulatory molecule.

Such combination therapies noted above encompass combined administration (where two or more therapeutic agents are included in the same or separate formulations), and separate administration, in which case, administration of a PD-L1 axis binding antagonist can occur prior to, simultaneously, and/or following, administration of the additional therapeutic agent or agents. In one instance, administration of PD-L1 axis binding antagonist and administration of an additional therapeutic agent occur within about one month, or within about one, two or three weeks, or within about one, two, three, four, five, or six days, of each other.

Without wishing to be bound to theory, it is thought that enhancing T-cell stimulation, by promoting an activating co-stimulatory molecule or by inhibiting a negative co-stimulatory molecule, may promote tumor cell death thereby treating or delaying progression of cancer. In some instances, a PD-L1 axis binding antagonist may be administered in conjunction with an agonist directed against an activating co-stimulatory molecule. In some instances, an activating co-stimulatory molecule may include CD40, CD226, CD28, OX40, GITR, CD137, CD27, HVEM, or CD127. In some instances, the agonist directed against an activating co-stimulatory molecule is an agonist antibody that binds to CD40, CD226, CD28, OX40, GITR, CD137, CD27, HVEM, or CD127. In some instances, a PD-L1 axis binding antagonist may be administered in conjunction with an antagonist directed against an inhibitory co-stimulatory molecule. In some instances, an inhibitory co-stimulatory molecule may include CTLA-4 (also known as CD152), TIM-3, BTLA, VISTA, LAG-3, B7-H3, B7-H4, IDO, TIGIT, MICA/B, or arginase. In some instances, the antagonist directed against an inhibitory co-stimulatory molecule is an antagonist antibody that binds to CTLA-4, TIM-3, BTLA, VISTA, LAG-3, B7-H3, B7-H4, IDO, TIGIT, MICA/B, or arginase.

In some instances, a PD-L1 axis binding antagonist may be administered in conjunction with an antagonist directed against CTLA-4 (also known as CD152), e.g., a blocking antibody. In some instances, a PD-L1 axis binding antagonist may be administered in conjunction with ipilimumab (also known as MDX-010, MDX-101, or YERVOY®). In some instances, a PD-L1 axis binding antagonist may be administered in conjunction with tremelimumab (also known as ticilimumab or CP-675,206). In some instances, a PD-L1 axis binding antagonist may be administered in conjunction with an antagonist directed against B7-H3 (also known as CD276), e.g., a blocking antibody. In some instances, a PD-L1 axis binding antagonist may be administered in conjunction with MGA271. In some instances, a PD-L1 axis binding antagonist may be administered in conjunction with an antagonist directed against a TGF-beta, e.g., metelimumab (also known as CAT-192), fresolimumab (also known as GC1008), or LY2157299.

In some instances, a PD-L1 axis binding antagonist may be administered in conjunction with a treatment comprising adoptive transfer of a T-cell (e.g., a cytotoxic T-cell or CTL) expressing a chimeric antigen receptor (CAR). In some instances, a PD-L1 axis binding antagonist may be administered in conjunction with a treatment comprising adoptive transfer of a T-cell comprising a dominant-negative TGF beta receptor, e.g., a dominant-negative TGF beta type II receptor. In some instances, a PD-L1 axis binding antagonist may be administered in conjunction with a treatment comprising a HERCREEM protocol (see, e.g., ClinicalTrials.gov Identifier NCT00889954).

In some instances, a PD-L1 axis binding antagonist may be administered in conjunction with an agonist directed against CD137 (also known as TNFRSF9, 4-1BB, or ILA), e.g., an activating antibody. In some instances, a PD-L1 axis binding antagonist may be administered in conjunction with urelumab (also known as BMS-663513). In some instances, a PD-L1 axis binding antagonist may be administered in conjunction with an agonist directed against CD40, e.g., an activating antibody. In some instances, a PD-L1 axis binding antagonist may be administered in conjunction with CP-870893. In some instances, a PD-L1 axis binding antagonist may be administered in conjunction with an agonist directed against OX40 (also known as CD134), e.g., an activating antibody. In some instances, a PD-L1 axis binding antagonist may be administered in conjunction with an anti-OX40 antibody (e.g., AgonOX). In some instances, a PD-L1 axis binding antagonist may be administered in conjunction with an agonist directed against CD27, e.g., an activating antibody. In some instances, a PD-L1 axis binding antagonist may be administered in conjunction with CDX-1127. In some instances, a PD-L1 axis binding antagonist may be administered in conjunction with an antagonist directed against indoleamine-2,3-dioxygenase (IDO). In some instances, with the IDO antagonist is 1-methyl-D-tryptophan (also known as 1-D-MT).

In some instances, a PD-L1 axis binding antagonist may be administered in conjunction with an antibody-drug conjugate. In some instances, the antibody-drug conjugate comprises mertansine or monomethyl auristatin E (MMAE). In some instances, a PD-L1 axis binding antagonist may be administered in conjunction with an anti-NaPi2b antibody-MMAE conjugate (also known as DNIB0600A or RG7599). In some instances, a PD-L1 axis binding antagonist may be administered in conjunction with trastuzumab emtansine (also known as T-DM1, ado-trastuzumab emtansine, or KADCYLA®, Genentech). In some instances, a PD-L1 axis binding antagonist may be administered in conjunction with DMUC5754A. In some instances, a PD-L1 axis binding antagonist may be administered in conjunction with an antibody-drug conjugate targeting the endothelin B receptor (EDNBR), e.g., an antibody directed against EDNBR conjugated with MMAE.

In some instances, a PD-L1 axis binding antagonist may be administered in conjunction with an anti-angiogenesis agent. In some instances, a PD-L1 axis binding antagonist may be administered in conjunction with an antibody directed against a VEGF, e.g., VEGF-A. In some instances, a PD-L1 axis binding antagonist may be administered in conjunction with bevacizumab (also known as AVASTIN®, Genentech). In some instances, a PD-L1 axis binding antagonist may be administered in conjunction with an antibody directed against angiopoietin 2 (also known as Ang2). In some instances, a PD-L1 axis binding antagonist may be administered in conjunction with MEDI3617.

In some instances, a PD-L1 axis binding antagonist may be administered in conjunction with an antineoplastic agent. In some instances, a PD-L1 axis binding antagonist may be administered in conjunction with an agent targeting CSF-1R (also known as M-CSFR or CD115). In some instances, a PD-L1 axis binding antagonist may be administered in conjunction with anti-CSF-1R (also known as IMC-CS4). In some instances, a PD-L1 axis binding antagonist may be administered in conjunction with an interferon, for example interferon alpha or interferon gamma. In some instances, a PD-L1 axis binding antagonist may be administered in conjunction with Roferon-A (also known as recombinant Interferon alpha-2a). In some instances, a PD-L1 axis binding antagonist may be administered in conjunction with GM-CSF (also known as recombinant human granulocyte macrophage colony stimulating factor, rhu GM-CSF, sargramostim, or LEUKINE®). In some instances, a PD-L1 axis binding antagonist may be administered in conjunction with IL-2 (also known as aldesleukin or PROLEUKIN®). In some instances, a PD-L1 axis binding antagonist may be administered in conjunction with IL-12. In some instances, a PD-L1 axis binding antagonist may be administered in conjunction with an antibody targeting CD20. In some instances, the antibody targeting CD20 is obinutuzumab (also known as GA101 or GAZYVA®) or rituximab. In some instances, a PD-L1 axis binding antagonist may be administered in conjunction with an antibody targeting GITR. In some instances, the antibody targeting GITR is TRX518.

In some instances, a PD-L1 axis binding antagonist may be administered in conjunction with a cancer vaccine. In some instances, the cancer vaccine is a peptide cancer vaccine, which in some instances is a personalized peptide vaccine. In some instances the peptide cancer vaccine is a multivalent long peptide, a multi-peptide, a peptide cocktail, a hybrid peptide, or a peptide-pulsed dendritic cell vaccine (see, e.g., Yamada et al., Cancer Sci. 104:14-21, 2013). In some instances, a PD-L1 axis binding antagonist may be administered in conjunction with an adjuvant. In some instances, a PD-L1 axis binding antagonist may be administered in conjunction with a treatment comprising a TLR agonist, e.g., Poly-ICLC (also known as HILTONOL®), LPS, MPL, or CpG ODN. In some instances, a PD-L1 axis binding antagonist may be administered in conjunction with tumor necrosis factor (TNF) alpha. In some instances, a PD-L1 axis binding antagonist may be administered in conjunction with IL-1. In some instances, a PD-L1 axis binding antagonist may be administered in conjunction with HMGB1. In some instances, a PD-L1 axis binding antagonist may be administered in conjunction with an IL-10 antagonist. In some instances, a PD-L1 axis binding antagonist may be administered in conjunction with an IL-4 antagonist. In some instances, a PD-L1 axis binding antagonist may be administered in conjunction with an IL-13 antagonist. In some instances, a PD-L1 axis binding antagonist may be administered in conjunction with an HVEM antagonist. In some instances, a PD-L1 axis binding antagonist may be administered in conjunction with an ICOS agonist, e.g., by administration of ICOS-L, or an agonistic antibody directed against ICOS. In some instances, a PD-L1 axis binding antagonist may be administered in conjunction with a treatment targeting CX3CL1. In some instances, a PD-L1 axis binding antagonist may be administered in conjunction with a treatment targeting CXCL9. In some instances, a PD-L1 axis binding antagonist may be administered in conjunction with a treatment targeting CXCL10. In some instances, a PD-L1 axis binding antagonist may be administered in conjunction with a treatment targeting CCL5. In some instances, a PD-L1 axis binding antagonist may be administered in conjunction with an LFA-1 or ICAM1 agonist. In some instances, a PD-L1 axis binding antagonist may be administered in conjunction with a Selectin agonist.

In some instances, a PD-L1 axis binding antagonist may be administered in conjunction with a targeted therapy. In some instances, a PD-L1 axis binding antagonist may be administered in conjunction with an inhibitor of B-Raf. In some instances, a PD-L1 axis binding antagonist may be administered in conjunction with vemurafenib (also known as ZELBORAF®). In some instances, a PD-L1 axis binding antagonist may be administered in conjunction with dabrafenib (also known as TAFINLAR®). In some instances, a PD-L1 axis binding antagonist may be administered in conjunction with erlotinib (also known as TARCEVA®). In some instances, a PD-L1 axis binding antagonist may be administered in conjunction with an inhibitor of a MEK, such as MEK1 (also known as MAP2K1) or MEK2 (also known as MAP2K2). In some instances, a PD-L1 axis binding antagonist may be administered in conjunction with cobimetinib (also known as GDC-0973 or XL-518). In some instances, a PD-L1 axis binding antagonist may be administered in conjunction with trametinib (also known as MEKINIST®). In some instances, a PD-L1 axis binding antagonist may be administered in conjunction with an inhibitor of K-Ras. In some instances, a PD-L1 axis binding antagonist may be administered in conjunction with an inhibitor of c-Met. In some instances, a PD-L1 axis binding antagonist may be administered in conjunction with onartuzumab (also known as MetMAb). In some instances, a PD-L1 axis binding antagonist may be administered in conjunction with an inhibitor of Alk. In some instances, a PD-L1 axis binding antagonist may be administered in conjunction with AF802 (also known as CH5424802 or alectinib). In some instances, a PD-L1 axis binding antagonist may be administered in conjunction with an inhibitor of a phosphatidylinositol 3-kinase (PI3K). In some instances, a PD-L1 axis binding antagonist may be administered in conjunction with BKM120. In some instances, a PD-L1 axis binding antagonist may be administered in conjunction with idelalisib (also known as GS-1101 or CAL-101). In some instances, a PD-L1 axis binding antagonist may be administered in conjunction with perifosine (also known as KRX-0401). In some instances, a PD-L1 axis binding antagonist may be administered in conjunction with an inhibitor of an Akt. In some instances, a PD-L1 axis binding antagonist may be administered in conjunction with MK2206. In some instances, a PD-L1 axis binding antagonist may be administered in conjunction with GSK690693. In some instances, a PD-L1 axis binding antagonist may be administered in conjunction with GDC-0941. In some instances, a PD-L1 axis binding antagonist may be administered in conjunction with an inhibitor of mTOR. In some instances, a PD-L1 axis binding antagonist may be administered in conjunction with sirolimus (also known as rapamycin). In some instances, a PD-L1 axis binding antagonist may be administered in conjunction with temsirolimus (also known as CCI-779 or Torisel®). In some instances, a PD-L1 axis binding antagonist may be administered in conjunction with everolimus (also known as RAD001). In some instances, a PD-L1 axis binding antagonist may be administered in conjunction with ridaforolimus (also known as AP-23573, MK-8669, or deforolimus). In some instances, a PD-L1 axis binding antagonist may be administered in conjunction with OSI-027. In some instances, a PD-L1 axis binding antagonist may be administered in conjunction with AZD8055. In some instances, a PD-L1 axis binding antagonist may be administered in conjunction with INK128. In some instances, a PD-L1 axis binding antagonist may be administered in conjunction with a dual PI3K/mTOR inhibitor. In some instances, a PD-L1 axis binding antagonist may be administered in conjunction with XL765. In some instances, a PD-L1 axis binding antagonist may be administered in conjunction with GDC-0980. In some instances, a PD-L1 axis binding antagonist may be administered in conjunction with BEZ235 (also known as NVP-BEZ235). In some instances, a PD-L1 axis binding antagonist may be administered in conjunction with BGT226. In some instances, a PD-L1 axis binding antagonist may be administered in conjunction with GSK2126458. In some instances, a PD-L1 axis binding antagonist may be administered in conjunction with PF-04691502. In some instances, a PD-L1 axis binding antagonist may be administered in conjunction with PF-05212384 (also known as PKI-587).

D. PD-L1 Axis Binding Antagonists for Use in the Methods of the Invention

Provided herein are methods for treating or delaying progression of a cancer (e.g., a bladder cancer (e.g., an urothelial bladder cancer)) in a patient comprising administering to the patient a therapeutically effective amount of a PD-L1 axis binding antagonist. Provided herein are methods for determining whether a patient suffering from a cancer (e.g., a bladder cancer (e.g., an urothelial bladder cancer)) is likely to respond to treatment comprising a PD-L1 axis binding antagonist. Provided herein are methods for predicting responsiveness of a patient suffering from a cancer (e.g., a bladder cancer (e.g., an urothelial bladder cancer)) to treatment comprising a PD-L1 axis binding antagonist. Provided herein are methods for selecting a therapy for a patient suffering from a cancer (e.g., a bladder cancer (e.g., an urothelial bladder cancer)). Any of the preceding methods may be based on the level of a somatic mutation provided herein, for example, mutation of genes listed in Table 1 of Table 2 in a tumor sample.

For example, a PD-L1 axis binding antagonist includes a PD-1 binding antagonist, a PD-L1 binding antagonist, and a PD-L2 binding antagonist. PD-1 (programmed death 1) is also referred to in the art as "programmed cell death 1," "PDCD1," "CD279," and "SLEB2." An exemplary human PD-1 is shown in UniProtKB/Swiss-Prot Accession No. Q15116. PD-L1 (programmed death ligand 1) is also referred to in the art as "programmed cell death 1 ligand 1," "PDCD1 LG1," "CD274," "B7-H," and "PDL1." An exemplary human PD-L1 is shown in UniProtKB/Swiss-Prot Accession No. Q9NZQ7.1. PD-L2 (programmed death ligand 2) is also referred to in the art as "programmed cell death 1 ligand 2," "PDCD1 LG2," "CD273," "B7-DC," "Btdc," and "PDL2." An exemplary human PD-L2 is shown in UniProtKB/Swiss-Prot Accession No. Q9BQ51. In some instances, PD-1, PD-L1, and PD-L2 are human PD-1, PD-L1 and PD-L2.

In some instances, the PD-1 binding antagonist is a molecule that inhibits the binding of PD-1 to its ligand binding partners. In a specific aspect the PD-1 ligand binding partners are PD-L1 and/or PD-L2. In another instance, a PD-L1 binding antagonist is a molecule that inhibits the binding of PD-L1 to its binding ligands. In a specific aspect, PD-L1 binding partners are PD-1 and/or B7-1. In another instance, the PD-L2 binding antagonist is a molecule that inhibits the binding of PD-L2 to its ligand binding partners. In a specific aspect, the PD-L2 binding ligand partner is PD-1. The antagonist may be an antibody, an antigen binding fragment thereof, an immunoadhesin, a fusion protein, or oligopeptide.

In some instances, the PD-1 binding antagonist is an anti-PD-1 antibody (e.g., a human antibody, a humanized antibody, or a chimeric antibody), for example, as described below. In some instances, the anti-PD-1 antibody is selected from the group consisting of MDX-1106 (nivolumab), MK-3475 (pembrolizumab), CT-011 (pidilizumab), MEDI-0680 (AMP-514), PDR001, REGN2810, and BGB-108. MDX-1106, also known as MDX-1106-04, ONO-4538, BMS-936558, or nivolumab, is an anti-PD-1 antibody described in WO2006/121168. MK-3475, also known as pembrolizumab or lambrolizumab, is an anti-PD-1 antibody described in WO 2009/114335. CT-011, also known as hBAT, hBAT-1 or pidilizumab, is an anti-PD-1 antibody described in WO 2009/101611. In some instances, the PD-1 binding antagonist is an immunoadhesin (e.g., an immunoadhesin comprising an extracellular or PD-1 binding portion of PD-L1 or PD-L2 fused to a constant region (e.g., an Fc region of an immunoglobulin sequence). In some instances, the PD-1 binding antagonist is AMP-224. AMP-224, also known as B7-DCIg, is a PD-L2-Fc fusion soluble receptor described in WO 2010/027827 and WO 2011/066342.

In some instances, the anti-PD-1 antibody is MDX-1106. Alternative names for "MDX-1106" include MDX-1106-04, ONO-4538, BMS-936558, and nivolumab. In some instances, the anti-PD-1 antibody is nivolumab (CAS Registry Number: 946414-94-4). In a still further instance, provided is an isolated anti-PD-1 antibody comprising a heavy chain variable region comprising the heavy chain variable region amino acid sequence from SEQ ID NO:1 and/or a light chain variable region comprising the light chain variable region amino acid sequence from SEQ ID NO:2. In a still further instance, provided is an isolated anti-PD-1 antibody comprising a heavy chain and/or a light chain sequence, wherein:

(a) the heavy chain sequence has at least 85%, at least 90%, at least 91%, at least 92%, at least 93%, at least 94%, at least 95%, at least 96%, at least 97%, at least 98%, at least 99% or 100% sequence identity to the heavy chain sequence:

(SEQ ID NO: 1)
QVQLVESGGGVVQPGRSLRLDCKASGITFSNSGMHWVRQAPGKGLEWVAV

IWYDGSKRYYADSVKGRFTISRDNSKNTLFLQMNSLRAEDTAVYYCATND

DYWGQGTLVTVSSASTKGPSVFPLAPCSRSTSESTAALGCLVKDYFPEPV

TVSWNSGALTSGVHTFPAVLQSSGLYSLSSVVTVPSSSLGTKTYTCNVDH

KPSNTKVDKRVESKYGPPCPPCPAPEFLGGPSVFLFPPKPKDTLMISRTP

EVTCVVVDVSQEDPEVQFNWYVDGVEVHNAKTKPREEQFNSTYRVVSVLT

VLHQDWLNGKEYKCKVSNKGLPSSIEKTISKAKGQPREPQVYTLPPSQEE

MTKNQVSLTCLVKGFYPSDIAVEWESNGQPENNYKTTPPVLDSDGSFFLY

SRLTVDKSRWQEGNVFSCSVMHEALHNHYTQKSLSLSLGK, and (b) the light chain sequences has at least 85%, at least 90%, at least 91%, at least 92%, at least 93%, at least 94%, at least 95%, at least 96%, at least 97%, at least 98%, at least 99% or 100% sequence identity to the light chain sequence:

(SEQ ID NO: 2)
EIVLTQSPATLSLSPGERATLSCRASQSVSSYLAWYQQKPGQAPRLLIYD

ASNRATGIPARFSGSGSGTDFTLTISSLEPEDFAVYYCQQSSNWPRTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.

In some instances, the PD-L1 axis binding antagonist is a PD-L2 binding antagonist. In some instances, the PD-L2 binding antagonist is an anti-PD-L2 antibody (e.g., a human antibody, a humanized antibody, or a chimeric antibody). In some instances, the PD-L2 binding antagonist is an immunoadhesin.

In some instances, the PD-L1 binding antagonist is an anti-PD-L1 antibody, for example, as described below. In some instances, the anti-PD-L1 antibody is capable of inhibiting binding between PD-L1 and PD-1 and/or between PD-L1 and B7-1. In some instances, the anti-PD-L1 antibody is a monoclonal antibody. In some instances, the anti-PD-L1 antibody is an antibody fragment selected from the group consisting of Fab, Fab'-SH, Fv, scFv, and (Fab')$_2$ fragments. In some instances, the anti-PD-L1 antibody is a humanized antibody. In some instances, the anti-PD-L1 antibody is a human antibody. In some instances, the anti-PD-L1 antibody is selected from the group consisting of YW243.55.S70, MPDL3280A (atezolizumab), MDX-1105, and MEDI4736 (durvalumab), and MSB0010718C (avelumab). Antibody YW243.55.S70 is an anti-PD-L1 described in WO 2010/077634. MDX-1105, also known as BMS-936559, is an anti-PD-L1 antibody described in WO2007/005874. MEDI4736 (durvalumab) is an anti-PD-L1 monoclonal antibody described in WO2011/066389 and US2013/034559. Examples of anti-PD-L1 antibodies useful for the methods of this invention, and methods for making thereof are described in PCT patent application WO 2010/077634, WO 2007/005874, WO 2011/066389, U.S. Pat. No. 8,217,149, and US 2013/034559, which are incorporated herein by reference.

Anti-PD-L1 antibodies described in WO 2010/077634 A1 and U.S. Pat. No. 8,217,149 may be used in the methods described herein. In some instances, the anti-PD-L1 antibody comprises a heavy chain variable region sequence of SEQ ID NO:3 and/or a light chain variable region sequence of SEQ ID NO:4. In a still further instance, provided is an isolated anti-PD-L1 antibody comprising a heavy chain variable region and/or a light chain variable region sequence, wherein:

(a) the heavy chain sequence has at least 85%, at least 90%, at least 91%, at least 92%, at least 93%, at least 94%, at least 95%, at least 96%, at least 97%, at least 98%, at least 99% or 100% sequence identity to the heavy chain sequence:

(SEQ ID NO: 3)
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSA, and (b) the light chain sequence has at least 85%, at least 90%, at least 91%, at least 92%, at least 93%, at least 94%, at least 95%, at least 96%, at least 97%, at least 98%, at least 99% or 100% sequence identity to the light chain sequence:

(SEQ ID NO: 4)
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKR.

In one instance, the anti-PD-L1 antibody comprises a heavy chain variable region comprising an HVR-H1, HVR-H2 and HVR-H3 sequence, wherein:

(SEQ ID NO: 5)
(a) the HVR-H1 sequence is GFTFSX$_1$SWIH;

(SEQ ID NO: 6)
(b) the HVR-H2 sequence is AWIX$_2$PYGGSX$_3$YYADSVKG;

(SEQ ID NO: 7)
(c) the HVR-H3 sequence is RHWPGGFDY;

further wherein: $X_1$ is D or G; $X_2$ is S or L; $X_3$ is T or S. In one specific aspect, $X_1$ is D; $X_2$ is S and $X_3$ is T. In another aspect, the polypeptide further comprises variable region heavy chain framework sequences juxtaposed between the HVRs according to the formula: (FR-H1)-(HVR-H1)-(FR-H2)-(HVR-H2)-(FR-H3)-(HVR-H3)-(FR-H4). In yet another aspect, the framework sequences are derived from human consensus framework sequences. In a further aspect, the framework sequences are VH subgroup III consensus framework. In a still further aspect, at least one of the framework sequences is the following:

(SEQ ID NO: 8)
FR-H1 is EVQLVESGGGLVQPGGSLRLSCAAS (SEQ ID NO: 9)
FR-H2 is WVRQAPGKGLEWV (SEQ ID NO: 10)
FR-H3 is RFTISADTSKNTAYLQMNSLRAEDTAVYYCAR (SEQ ID NO: 11)
FR-H4 is WGQGTLVTVSA.

In a still further aspect, the heavy chain polypeptide is further combined with a variable region light chain comprising an HVR-L1, HVR-L2 and HVR-L3, wherein:

(SEQ ID NO: 12)
(a) the HVR-L1 sequence is RASQX$_4$X$_5$X$_6$TX$_7$X$_8$A;

(SEQ ID NO: 13);
(b) the HVR-L2 sequence is SASX$_9$LX$_{10}$S, (SEQ ID NO: 14)
(c) the HVR-L3 sequence is QQX$_{11}$X$_{12}$X$_{13}$X$_{14}$PX$_{15}$T;

wherein: $X_4$ is D or V; $X_5$ is V or I; $X_6$ is S or N; $X_7$ is A or F; $X_8$ is V or L; $X_9$ is F or T; $X_{10}$ is Y or A; $X_{11}$ is Y, G, F, or S; $X_{12}$ is L, Y, F or W; $X_{13}$ is Y, N, A, T, G, F or I; $X_{14}$ is H, V, P, T or I; $X_{15}$ is A, W, R, P or T. In a still further aspect, $X_4$ is D; $X_5$ is V; $X_6$ is S; $X_7$ is A; $X_8$ is V; $X_9$ is F; $X_{10}$ is Y; $X_{11}$, is Y; $X_{12}$ is L; $X_{13}$ is Y; $X_{14}$ is H; $X_{15}$ is A.

In a still further aspect, the light chain further comprises variable region light chain framework sequences juxtaposed between the HVRs according to the formula: (FR-L1)-(HVR-L1)-(FR-L2)-(HVR-L2)-(FR-L3)-(HVR-L3)-(FR-L4). In a still further aspect, the framework sequences are derived from human consensus framework sequences. In a still further aspect, the framework sequences are VL kappa I consensus framework. In a still further aspect, at least one of the framework sequence is the following:

(SEQ ID NO: 15)
FR-L1 is DIQMTQSPSSLSASVGDRVTITC (SEQ ID NO: 16)
FR-L2 is WYQQKPGKAPKLLIY (SEQ ID NO: 17)
FR-L3 is GVPSRFSGSGSGTDFTLTISSLQPEDFATYYC (SEQ ID NO: 18)
FR-L4 is FGQGTKVEIKR.

In another instance, provided is an isolated anti-PD-L1 antibody or antigen binding fragment comprising a heavy chain and a light chain variable region sequence, wherein:

(a) the heavy chain comprises an HVR-H1, HVR-H2 and HVR-H3, wherein further:

(SEQ ID NO: 5)
(i) the HVR-H1 sequence is GFTFSX$_1$SWIH;

(SEQ ID NO: 6)
(ii) the HVR-H2 sequence is AWIX$_2$PYGGSX$_3$YYADSVKG (SEQ ID NO: 7)
(iii) the HVR-H3 sequence is RHWPGGFDY, and (b) the light chain comprises an HVR-L1, HVR-L2 and HVR-L3, wherein further:

(SEQ ID NO: 12)
(i) the HVR-L1 sequence is RASQX$_4$X$_5$X$_6$TX$_7$X$_8$A (SEQ ID NO: 13)
(ii) the HVR-L2 sequence is SASX$_9$LX$_{10}$S; and (SEQ ID NO: 14)
(iii) the HVR-L3 sequence is QQX$_{11}$X$_{12}$X$_{13}$X$_{14}$PX$_{15}$T;

wherein: $X_1$ is D or G; $X_2$ is S or L; $X_3$ is T or S; $X_4$ is D or V; $X_5$ is V or I; $X_6$ is S or N; $X_7$ is A or F; X is V or L; $X_e$ is F or T; $X_{10}$ is Y or A; $X_{11}$ is Y, G, F, or S; $X_{12}$ is L, Y, F or W; $X_{13}$ is Y, N, A, T, G, F or I; $X_{14}$ is H, V, P, T or I; $X_{15}$ is A, W, R, P or T. In a specific aspect, $X_1$ is D; $X_2$ is S and $X_3$ is T. In another aspect, $X_4$ is D; $X_5$ is V; $X_6$ is S; $X_7$ is A; $X_8$ is V; $X_9$ is F; $X_{10}$ is Y; $X_{11}$ is Y; $X_{12}$ is L; $X_{13}$ is Y; $X_{14}$ is H; $X_{15}$ is A. In yet another aspect, $X_1$ is D; $X_2$ is S and $X_3$ is T, $X_4$ is D; $X_5$ is V; $X_6$ is S; $X_7$ is A; $X_8$ is V; $X_9$ is F; $X_{10}$ is Y; $X_{11}$ is Y; $X_{12}$ is L; $X_{13}$ is Y; $X_{14}$ is H and $X_{15}$ is A.

In a further aspect, the heavy chain variable region comprises one or more framework sequences juxtaposed between the HVRs as: (FR-H1)-(HVR-H1)-(FR-H2)-(HVR-H2)-(FR-H3)-(HVR-H3)-(FR-H4), and the light chain variable regions comprises one or more framework sequences juxtaposed between the HVRs as: (FR-L1)-(HVR-L1)-(FR-L2)-(HVR-L2)-(FR-L3)-(HVR-L3)-(FR-L4). In a still further aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences are set forth as SEQ ID NOs:8, 9, 10 and 11. In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences are set forth as SEQ ID NOs:15, 16, 17 and 18.

In a still further specific aspect, the antibody further comprises a human or murine constant region. In a still further aspect, the human constant region is selected from the group consisting of IgG1, IgG2, IgG2, IgG3, and IgG4. In a still further specific aspect, the human constant region is IgG1. In a still further aspect, the murine constant region is selected from the group consisting of IgG1, IgG2A, IgG2B, and IgG3. In a still further aspect, the murine constant region in IgG2A. In a still further specific aspect, the antibody has reduced or minimal effector function. In a still further specific aspect the minimal effector function results from an "effector-less Fc mutation" or aglycosylation. In still a further instance, the effector-less Fc mutation is an N297A or D265A/N297A substitution in the constant region.

In yet another instance, provided is an anti-PD-L1 antibody comprising a heavy chain and a light chain variable region sequence, wherein:
(a) the heavy chain further comprises an HVR-H1, HVR-H2 and an HVR-H3 sequence having at least 85% sequence identity to GFTFSDSWIH (SEQ ID NO:19), AWISPYGGSTYYADSVKG (SEQ ID NO:20) and RHWPGGFDY (SEQ ID NO:21), respectively, or
(b) the light chain further comprises an HVR-L1, HVR-L2 and an HVR-L3 sequence having at least 85% sequence identity to RASQDVSTAVA (SEQ ID NO:22), SASFLYS (SEQ ID NO:23) and QQYLYHPAT (SEQ ID NO:24), respectively.

In a specific aspect, the sequence identity is 86%, 87%, 88%, 89%, 90%, 91%, 92%, 93%, 94%, 95%, 96%, 97%, 98%, 99% or 100%.

In another aspect, the heavy chain variable region comprises one or more framework sequences juxtaposed between the HVRs as: (FR-H1)-(HVR-H1)-(FR-H2)-(HVR-H2)-(FR-H3)-(HVR-H3)-(FR-H4), and the light chain variable regions comprises one or more framework sequences juxtaposed between the HVRs as: (FR-L1)-(HVR-L1)-(FR-L2)-(HVR-L2)-(FR-L3)-(HVR-L3)-(FR-L4). In yet another aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences are set forth as SEQ ID NOs:8, 9, 10 and 11. In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences are set forth as SEQ ID NOs:15, 16, 17 and 18.

In a still further specific aspect, the antibody further comprises a human or murine constant region. In a still further aspect, the human constant region is selected from the group consisting of IgG1, IgG2, IgG2, IgG3, and IgG4. In a still further specific aspect, the human constant region is IgG1. In a still further aspect, the murine constant region is selected from the group consisting of IgG1, IgG2A, IgG2B, and IgG3. In a still further aspect, the murine constant region in IgG2A. In a still further specific aspect, the antibody has reduced or minimal effector function. In a still further specific aspect the minimal effector function results from an "effector-less Fc mutation" or aglycosylation. In still a further instance, the effector-less Fc mutation is an N297A or D265A/N297A substitution in the constant region.

In another further instance, provided is an isolated anti-PD-L1 antibody comprising a heavy chain and a light chain variable region sequence, wherein:
(a) the heavy chain sequence has at least 85% sequence identity to the heavy chain sequence:

(SEQ ID NO: 25)
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSS, and/or
(b) the light chain sequences has at least 85% sequence identity to the light chain sequence:

(SEQ ID NO: 4)
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKR.

In a specific aspect, the sequence identity is 86%, 87%, 88%, 89%, 90%, 91%, 92%, 93%, 94%, 95%, 96%, 97%, 98%, 99% or 100%. In another aspect, the heavy chain variable region comprises one or more framework sequences juxtaposed between the HVRs as: (FR-H1)-(HVR-H1)-(FR-H2)-(HVR-H2)-(FR-H3)-(HVR-H3)-(FR-H4), and the light chain variable regions comprises one or more framework sequences juxtaposed between the HVRs as: (FR-L1)-(HVR-L1)-(FR-L2)-(HVR-L2)-(FR-L3)-(HVR-L3)-(FR-L4). In yet another aspect, the framework sequences are derived from human consensus framework sequences. In a further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences are set forth as SEQ ID NOs:8, 9, 10 and WGQGTLVTVSS (SEQ ID NO:27).

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences are set forth as SEQ ID NOs:15, 16, 17 and 18.

In a still further specific aspect, the antibody further comprises a human or murine constant region. In a still further aspect, the human constant region is selected from the group consisting of IgG1, IgG2, IgG2, IgG3, and IgG4. In a still further specific aspect, the human constant region is IgG1. In a still further aspect, the murine constant region is selected from the group consisting of IgG1, IgG2A, IgG2B, and IgG3. In a still further aspect, the murine constant region in IgG2A. In a still further specific aspect, the antibody has reduced or minimal effector function. In a still further specific aspect, the minimal effector function results from production in prokaryotic cells. In a still further specific aspect the minimal effector function results from an "effector-less Fc mutation" or aglycosylation. In still a further instance, the effector-less Fc mutation is an N297A or D265A/N297A substitution in the constant region.

In a further aspect, the heavy chain variable region comprises one or more framework sequences juxtaposed between the HVRs as: (FR-H1)-(HVR-H1)-(FR-H2)-(HVR-H2)-(FR-H3)-(HVR-H3)-(FR-H4), and the light chain variable regions comprises one or more framework sequences juxtaposed between the HVRs as: (FR-L1)-(HVR-L1)-(FR-L2)-(HVR-L2)-(FR-L3)-(HVR-L3)-(FR-L4). In a still further aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

```
                                           (SEQ ID NO: 29)
FR-H1    EVQLVESGGGLVQPGGSLRLSCAASGFTFS (SEQ ID NO: 30)
FR-H2    WVRQAPGKGLEWVA (SEQ ID NO: 10)
FR-H3    RFTISADTSKNTAYLQMNSLRAEDTAVYYCAR (SEQ ID NO: 27)
FR-H4    WGQGTLVTVSS.
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
                                           (SEQ ID NO: 15)
FR-L1    DIQMTQSPSSLSASVGDRVTITC (SEQ ID NO: 16)
FR-L2    WYQQKPGKAPKLLIY (SEQ ID NO: 17)
FR-L3    GVPSRFSGSGSGTDFTLTISSLQPEDFATYYC (SEQ ID NO: 28)
FR-L4    FGQGTKVEIK.
```

In a still further specific aspect, the antibody further comprises a human or murine constant region. In a still further aspect, the human constant region is selected from the group consisting of IgG1, IgG2, IgG2, IgG3, and IgG4. In a still further specific aspect, the human constant region is IgG1. In a still further aspect, the murine constant region is selected from the group consisting of IgG1, IgG2A, IgG2B, and IgG3. In a still further aspect, the murine constant region in IgG2A. In a still further specific aspect, the antibody has reduced or minimal effector function. In a still further specific aspect the minimal effector function results from an "effector-less Fc mutation" or aglycosylation. In still a further instance, the effector-less Fc mutation is an N297A or D265A/N297A substitution in the constant region.

In yet another instance, provided is an anti-PD-L1 antibody comprising a heavy chain and a light chain variable region sequence, wherein:
(c) the heavy chain further comprises an HVR-H1, HVR-H2 and an HVR-H3 sequence having at least 85% sequence identity to GFTFSDSWIH (SEQ ID NO:19), AWISPYGGSTYYADSVKG (SEQ ID NO:20) and RHWPGGFDY (SEQ ID NO:21), respectively, and/or
(d) the light chain further comprises an HVR-L1, HVR-L2 and an HVR-L3 sequence having at least 85% sequence identity to RASQDVSTAVA (SEQ ID NO:22), SASFLYS (SEQ ID NO:23) and QQYLYHPAT (SEQ ID NO:24), respectively.

In a specific aspect, the sequence identity is 86%, 87%, 88%, 89%, 90%, 91%, 92%, 93%, 94%, 95%, 96%, 97%, 98%, 99% or 100%.

In another aspect, the heavy chain variable region comprises one or more framework sequences juxtaposed between the HVRs as: (FR-H1)-(HVR-H1)-(FR-H2)-(HVR-H2)-(FR-H3)-(HVR-H3)-(FR-H4), and the light chain variable regions comprises one or more framework sequences juxtaposed between the HVRs as: (FR-L1)-(HVR-L1)-(FR-L2)-(HVR-L2)-(FR-L3)-(HVR-L3)-(FR-L4). In yet another aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences are set forth as SEQ ID NOs:8, 9, 10 and WGQGTLVTVSSASTK (SEQ ID NO:31).

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences are set forth as SEQ ID NOs:15, 16, 17 and 18. In a still further specific aspect, the antibody further comprises a human or murine constant region. In a still further aspect, the human constant region is selected from the group consisting of IgG1, IgG2, IgG2, IgG3, and IgG4. In a still further specific aspect, the human constant region is IgG1. In a still further aspect, the murine constant region is selected from the group consisting of IgG1, IgG2A, IgG2B, and IgG3. In a still further aspect, the murine constant region in IgG2A. In a still further specific aspect, the antibody has reduced or minimal effector function. In a still further specific aspect the minimal effector function results from an "effector-less Fc mutation" or aglycosylation. In still a further instance, the effector-less Fc mutation is an N297A or D265A/N297A substitution in the constant region.

In a still further instance, provided is an isolated anti-PD-L1 antibody comprising a heavy chain and a light chain variable region sequence, wherein:
(a) the heavy chain sequence has at least 85% sequence identity to the heavy chain sequence:

```
                                           (SEQ ID NO: 26)
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSSASTK,
``` or
(b) the light chain sequences has at least 85% sequence identity to the light chain sequence:

(SEQ ID NO: 4)
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKR.

In some instances, provided is an isolated anti-PD-L1 antibody comprising a heavy chain and a light chain variable region sequence, wherein the light chain variable region sequence has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of SEQ ID NO:4. In some instances, provided is an isolated anti-PD-L1 antibody comprising a heavy chain and a light chain variable region sequence, wherein the heavy chain variable region sequence has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of SEQ ID NO:26. In some instances, provided is an isolated anti-PD-L1 antibody comprising a heavy chain and a light chain variable region sequence, wherein the light chain variable region sequence has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:4 and the heavy chain variable region sequence has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:26. In some instances, one, two, three, four, or five amino acid residues at the N-terminal of the heavy and/or light chain may be deleted, substituted or modified.

In a still further instance, provided is an isolated anti-PD-L1 antibody comprising a heavy chain and a light chain sequence, wherein:
(a) the heavy chain sequence has at least 85% sequence identity to the heavy chain sequence:

(SEQ ID NO: 32)
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYAST

YRVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVLD

SDGSFFLYSKLTVDKSRWQQGNVFSCSVMHEALHNHYTQKSLSLSPG, and/or
(b) the light chain sequences has at least 85% sequence identity to the light chain sequence:

(SEQ ID NO: 33)
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.

In some instances, provided is an isolated anti-PD-L1 antibody comprising a heavy chain and a light chain sequence, wherein the light chain sequence has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:33. In some instances, provided is an isolated anti-PD-L1 antibody comprising a heavy chain and a light chain sequence, wherein the heavy chain sequence has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:32. In some instances, provided is an isolated anti-PD-L1 antibody comprising a heavy chain and a light chain sequence, wherein the light chain sequence has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:33 and the heavy chain sequence has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:32.

In some instances, the isolated anti-PD-L1 antibody is aglycosylated. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Removal of glycosylation sites form an antibody is conveniently accomplished by altering the amino acid sequence such that one of the above-described tripeptide sequences (for N-linked glycosylation sites) is removed. The alteration may be made by substitution of an asparagine, serine or threonine residue within the glycosylation site another amino acid residue (e.g., glycine, alanine or a conservative substitution).

In any of the instances herein, the isolated anti-PD-L1 antibody can bind to a human PD-L1, for example a human PD-L1 as shown in UniProtKB/Swiss-Prot Accession No. Q9NZQ7.1, or a variant thereof.

In a still further instance, provided is an isolated nucleic acid encoding any of the antibodies described herein. In some instances, the nucleic acid further comprises a vector suitable for expression of the nucleic acid encoding any of the previously described anti-PD-L1 antibodies. In a still further specific aspect, the vector is in a host cell suitable for expression of the nucleic acid. In a still further specific aspect, the host cell is a eukaryotic cell or a prokaryotic cell. In a still further specific aspect, the eukaryotic cell is a mammalian cell, such as Chinese hamster ovary (CHO) cell.

The antibody or antigen binding fragment thereof, may be made using methods known in the art, for example, by a process comprising culturing a host cell containing nucleic acid encoding any of the previously described anti-PD-L1 antibodies or antigen-binding fragments in a form suitable for expression, under conditions suitable to produce such antibody or fragment, and recovering the antibody or fragment.

It is expressly contemplated that such PD-L1 axis binding antagonist antibodies (e.g., anti-PD-L1 antibodies, anti-PD-1 antibodies, and anti-PD-L2 antibodies), or other antibodies described herein for use in any of the instances enumerated above may have any of the features, singly or in combination, described in Sections 1-7 below.

1. Antibody Affinity

In certain instances, an antibody provided herein (e.g., an anti-PD-L1 antibody or an anti-PD-1 antibody) has a dissociation constant (Kd) of ≤1 µM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M).

In one instance, Kd is measured by a radiolabeled antigen binding assay (RIA). In one instance, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 µM or 26 µM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another instance, Kd is measured using a BIACORE® surface plasmon resonance assay. For example, an assay using a BIACORE®-2000 or a BIACORE®-3000 (BIAcore, Inc., Piscataway, NJ) is performed at 25° C. with immobilized antigen CM5 chips at ~10 response units (RU). In one instance, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, for example, Chen et al., *J. Mol. Biol.* 293:865-881 (1999). If the on-rate exceeds $10^6$ $M^{-1}s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain instances, an antibody (e.g., an anti-PD-L1 antibody or an anti-PD-1 antibody) provided herein is an antibody fragment. Antibody fragments include, but are not limited to, Fab, Fab', Fab'-SH, F(ab')2, Fv, and scFv fragments, and other fragments described below. For a review of certain antibody fragments, see Hudson et al. *Nat. Med.* 9:129-134 (2003). For a review of scFv fragments, see, e.g., Pluckthun, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al. *Nat. Med.* 9:129-134 (2003); and Hollinger et al. *Proc. Natl. Acad. Sci. USA* 90: 6444-6448 (1993). Triabodies and tetrabodies are also described in Hudson et al. *Nat. Med.* 9:129-134 (2003).

Single-domain antibodies are antibody fragments comprising all or a portion of the heavy chain variable domain or all or a portion of the light chain variable domain of an antibody. In certain instances, a single-domain antibody is a human single-domain antibody (Domantis, Inc., Waltham, MA; see, e.g., U.S. Pat. No. 6,248,516 B1).

Antibody fragments can be made by various techniques, including but not limited to proteolytic digestion of an intact antibody as well as production by recombinant host cells (e.g., *E. coli* or phage), as described herein.

3. Chimeric and Humanized Antibodies

In certain instances, an antibody (e.g., an anti-PD-L1 antibody or an anti-PD-1 antibody) provided herein is a chimeric antibody. Certain chimeric antibodies are described, e.g., in U.S. Pat. No. 4,816,567; and Morrison et al. *Proc. Natl. Acad. Sci. USA,* 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain instances, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some instances, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat. Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain instances, an antibody (e.g., an anti-PD-L1 antibody or an anti-PD-1 antibody) provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCI-MOUSE® technology. Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in Li et al. *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention (e.g., anti-PD-L1 antibodies and anti-PD-1 antibodies) may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, NJ, 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, NJ, 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In any one of the above aspects, an antibody (e.g., an anti-PD-L1 antibody or an anti-PD-1 antibody) provided herein may be a multispecific antibody, for example, a bispecific antibody. Multispecific antibodies are monoclonal antibodies that have binding specificities for at least two different sites. In certain instances, an antibody provided herein is a multispecific antibody, e.g., a bispecific antibody. In certain instances, one of the binding specificities is for PD-L1 and the other is for any other antigen. In certain instances, bispecific antibodies may bind to two different epitopes of PD-L1. Bispecific antibodies may also be used to localize cytotoxic agents to cells which express PD-L1. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (see, e.g., WO 2009/089004A1); cross-linking two or more antibodies or fragments (see, e.g., U.S. Pat. No. 4,676,980, and Brennan et al., *Science* 229: 81 (1985)); using leucine zippers to produce bi-specific antibodies (see, e.g., Kostelny et al., *J. Immunol.* 148(5): 1547-1553 (1992)); using "diabody" technology for making bispecific antibody fragments (see, e.g., Hollinger et al., *Proc. Nat. Acad. Sci. USA* 90:6444-6448 (1993)); using single-chain Fv (sFv) dimers (see, e.g., Gruber et al., *J. Immunol.* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g., US 2006/0025576A1).

The antibody or fragment herein also includes a "Dual Acting FAb" or "DAF" comprising an antigen binding site that binds to PD-L1 as well as another, different antigen.

7. Antibody Variants

In certain instances, amino acid sequence variants of the antibodies of the invention (e.g., anti-PD-L1 antibodies and anti-PD-1 antibodies) are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, for example, antigen-binding.

I. Substitution, Insertion, and Deletion Variants

In certain instances, antibody variants having one or more amino acid substitutions are provided. Sites of interest for substitutional mutagenesis include the HVRs and FRs. Conservative substitutions are shown in Table 3 under the heading of "preferred substitutions." More substantial changes are provided in Table 3 under the heading of "exemplary substitutions," and as further described below in reference to amino acid side chain classes. Amino acid substitutions may be introduced into an antibody of interest and the products screened for a desired activity, for example, retained/improved antigen binding, decreased immunogenicity, or improved Antibody-Dependent Cell-Mediated Cytotoxicity (ADCC) or Complement Dependant Cytotoxicity (CDC).

TABLE 3

Exemplary and Preferred Amino Acid Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ilie;
(2) neutral hydrophilic: Cys, Ser, Thr, Asn, Gin;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity and/or reduced immunogenicity) relative to the parent antibody and/or will have substantially retained certain biological properties of the parent antibody. An exemplary substitutional variant is an affinity matured antibody, which may be conveniently generated, for example, using phage display-based affinity maturation techniques such as those described herein. Briefly, one or more HVR residues are mutated and the variant antibodies displayed on phage and screened for a particular biological activity (e.g., binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., *Human Press*, Totowa, NJ, (2001)). In some instances of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain instances, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen-contacting residues in the HVRs. In certain instances of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

II. Glycosylation Variants

In certain instances, antibodies of the invention can be altered to increase or decrease the extent to which the antibody is glycosylated. Addition or deletion of glycosylation sites to an antibody of the invention may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the $CH_2$ domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some instances, modifications of the oligosaccharide in an antibody of the invention may be made in order to create antibody variants with certain improved properties.

In one instance, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, for example, U.S. Patent Publication Nos. US 2003/0157108 and US 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); U.S. Pat. Appl. No. US 2003/0157108 A1; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4): 680-688 (2006); and WO2003/085107).

Antibody variants are further provided with bisected oligosaccharides, for example, in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

III. Fc Region Variants

In certain instances, one or more amino acid modifications may be introduced into the Fc region of an antibody of the invention, thereby generating an Fc region variant. The Fc region variant may comprise a human Fc region sequence (e.g., a human IgG1, IgG2, IgG3 or IgG4 Fc region) comprising an amino acid modification (e.g., a substitution) at one or more amino acid positions.

In certain instances, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest are described in U.S. Pat. No. 5,500,362 (see, e.g., Hellstrom, I. et al. *Proc. Natl. Acad. Sci. USA* 83:7059-7063 (1986)) and Hellstrom, I et al., *Proc. Natl. Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and CYTOTOX 96® non-radioactive cytotoxicity assay (Promega, Madison, WI))). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Natl. Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, e.g., Gazzano-Santoro et al., *J. Immunol. Methods* 202:163 (1996); Cragg et al., *Blood.* 101:1045-1052 (2003); and Cragg et al., *Blood.* 103:2738-2743 (2004)). FcRn binding and in vivo clearance/half life determinations can also be performed using methods known in the art (see, e.g., Petkova et al. *Int'l. Immunol.* 18(12):1759-1769 (2006)).

Antibodies with reduced effector function include those with substitution of one or more of Fc region residues 238, 265, 269, 270, 297, 327 and 329 (U.S. Pat. Nos. 6,737,056 and 8,219,149). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. Nos. 7,332,581 and 8,219,149).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain instances, an antibody variant comprises an Fc region with one or more amino acid substitutions which improve ADCC, e.g., substitutions at positions 298, 333, and/or 334 of the Fc region (EU numbering of residues).

In some instances, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

IV. Cysteine Engineered Antibody Variants

In certain instances, it may be desirable to create cysteine engineered antibodies, e.g., "thioMAbs," in which one or more residues of an antibody are substituted with cysteine residues. In particular instances, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain instances, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

V. Antibody Derivatives

In certain instances, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another instance, conjugates of an antibody and non-proteinaceous moiety that may be selectively heated by exposure to radiation are provided. In one instance, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

VI. Immunoconjugates

The invention also provides immunoconjugates comprising an antibody herein (e.g., an anti-PD-L1 antibody or an anti-PD-1 antibody) conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one instance, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another instance, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another instance, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron. Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triamine-pentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, sulfo-SMPB, and SVSB (succinimidyl-(4-vinylsulfone)benzoate) which are commercially available (e.g., from Pierce Biotechnology, Inc., Rockford, IL, U.S.A).

V. Pharmaceutical Formulations

Therapeutic formulations of the PD-L1 axis binding antagonists used in accordance with the present invention (e.g., an anti-PD-L1 antibody (e.g., MPDL3280A)) are prepared for storage by mixing the antagonist having the desired degree of purity with optional pharmaceutically acceptable carriers, excipients, or stabilizers in the form of lyophilized formulations or aqueous solutions. For general information concerning formulations, see, e.g., Gilman et al. (eds.) *The Pharmacological Bases of Therapeutics*, 8th Ed., Pergamon Press, 1990; A. Gennaro (ed.), *Remington's Pharmaceutical Sciences*, 18th Edition, Mack Publishing Co., Pennsylvania, 1990; Avis et al. (eds.) *Pharmaceutical Dosage Forms: Parenteral Medications Dekker, New York*, 1993; Lieberman et al. (eds.) *Pharmaceutical Dosage Forms: Tablets Dekker, New York*, 1990; Lieberman et al. (eds.), *Pharmaceutical Dosage Forms: Disperse Systems Dekker, New York*, 1990; and Walters (ed.) Dermatological and Transdermal Formulations (Drugs and the Pharmaceutical Sciences), Vol 119, Marcel Dekker, 2002.

Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™, or polyethylene glycol (PEG).

The formulation herein may also contain more than one active compound, preferably those with complementary activities that do not adversely affect each other. The type and effective amounts of such medicaments depend, for example, on the amount and type of antagonist present in the formulation, and clinical parameters of the subjects.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antagonist, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid.

The formulations to be used for in vivo administration must be sterile. This is readily accomplished by filtration through sterile filtration membranes.

It is to be understood that any of the above articles of manufacture may include an immunoconjugate described herein in place of or in addition to a PD-L1 axis binding antagonist.

VI. Diagnostic Kits and Articles of Manufacture

Provided herein are diagnostic kits comprising one or more reagents for determining the presence of a somatic mutations in a sample from an individual or patient with a disease or disorder (e.g., cancer, including bladder cancer). In some instances, the presence of the somatic mutation in the sample indicates a higher likelihood of efficacy when the individual is treated with a PD-L1 axis binding antagonist. In some instances, the absence of the somatic mutation in the sample indicates a lower likelihood of efficacy when the individual with the disease is treated with the PD-L1 axis binding antagonist. Optionally, the kit may further include instructions to use the kit to select a medicament (e.g., a PD-L1 axis binding antagonist, such as an anti-PD-L1 antibody such as MPDL3280A) for treating the disease or disorder if the individual has somatic mutations in the sample. In another instance, the instructions are to use the kit to select a medicament other than PD-L1 axis binding antagonist if the individual does not express the biomarker in the sample.

Provided herein are also articles of manufacture including, packaged together, a PD-L1 axis binding antagonist (e.g., an anti-PD-L1 antibody) in a pharmaceutically acceptable carrier and a package insert indicating that the PD-L1 axis binding antagonist (e.g., anti-PD-L1 antibody) is for treating a patient with a disease or disorder (e.g., cancer) based on the presence of somatic mutations. Treatment methods include any of the treatment methods disclosed herein. The invention also concerns a method for manufacturing an article of manufacture comprising combining in a package a pharmaceutical composition comprising a PD-L1 axis binding antagonist (e.g., an anti-PD-L1 antibody) and a package insert indicating that the pharmaceutical composition is for treating a patient with a disease or disorder based on the presence of somatic mutations (e.g., somatic mutations in a gene listed in Table 1 and/or Table 2, e.g., in tumor cells).

The article of manufacture may include, for example, a container and a label or package insert on or associated with the container. Suitable containers include, for example, bottles, vials, syringes, and the like. The container may be formed from a variety of materials such as glass or plastic. The container holds or contains a composition comprising the cancer medicament as the active agent and may have a sterile access port (e.g., the container may be an intravenous solution bag or a vial having a stopper pierceable by a hypodermic injection needle).

The article of manufacture may further include a second container comprising a pharmaceutically-acceptable diluent buffer, such as bacteriostatic water for injection (BWFI), phosphate-buffered saline, Ringer's solution, and/or dextrose solution. The article of manufacture may further include other materials desirable from a commercial and user standpoint, including other buffers, diluents, filters, needles, and syringes.

The article of manufacture of the present invention also includes information, for example in the form of a package insert, indicating that the composition is used for treating cancer based on the presence of the somatic mutation(s) herein. The insert or label may take any form, such as paper or on electronic media such as a magnetically recorded medium (e.g., floppy disk), a CD-ROM, a Universal Serial Bus (USB) flash drive, and the like. The label or insert may also include other information concerning the pharmaceutical compositions and dosage forms in the kit or article of manufacture.

EXAMPLES

The following examples are provided to illustrate, but not to limit the presently claimed invention.

Example 1: Examining the Association of Atezolizumab Treatment and Mutation Load in Patients with Locally Advanced and Metastatic Carcinoma The association between mutation loads in urothelial bladder cancer (UBC) tumors with response to treatment with PD-L1 axis binding antagonists was evaluated. Responses to treatment with atezolizumab (MPDL3280A), a PD-L1 axis binding antagonist (e.g., an anti-PD-L1 antibody), was observed in all patients.

Study Oversight and Conduct

The study was approved by the independent review board at each participating site and was conducted in full conformance of the provisions of the Declaration of Helsinki and the Good Clinical Practice Guidelines. An independent Data Monitoring Committee reviewed the available safety data every six months after the first patient enrolled. The data analyses and manuscript writing were conducted by the sponsor and the authors.

Study Design and Treatment

This ongoing phase II, single-arm study (Clinical Trial No.: NCT02108652 (IMvigor210)) was designed to evaluate the effect of atezolizumab (MPDL3280A) treatment in patients with locally advanced or metastatic urothelial bladder cancer. Patients were enrolled into one of two cohorts. Cohort 1 consisted of patients who were treatment-naïve and ineligible for platinum-containing therapy. Cohort 2 contained patients who had progressed during or following a prior platinum-containing therapy, e.g., a prior platinum-containing therapy for locally advanced or metastatic urothelial bladder cancer.

Patients in both cohorts received a fixed dose of 1200 mg intravenous atezolizumab administered on Day 1 of each 21-day cycle. Dose interruptions were allowed, but dose reductions were not permitted. Patients were informed of the potential for pseudo-progression as part of the consent process, and advised to discuss treatment beyond progression with their study physician. Patients were permitted to continue atezolizumab treatment after RECIST v1.1 criteria for progressive disease if they met pre-speficied criteria for clinical benefit to allow for the identification of non-conventional responses. The primary efficacy endpoint of this study was objective response rate based upon two distinct methods: independent review facility (IRF)-assessed per RECIST version 1.1, and investigator-assessed per modified RECIST criteria to better evaluate atypical response kinetics observed with immunotherapy, see Eisehauer et al. (2009) *Eur J Cancer* 45:228-47, Nishino et al (2015) *Eur J Radiol.* 84:1259-68. Dual endpoints were chosen due to the emerging recognition that RECIST v1.1 may be inadequate to fully capture the benefit of the unique patterns of response from immunotherapeutic agents, see Chiou et al. (2015) *J Clin Oncol.* 33:3541-3. Secondary efficacy endpoints included: duration of response and progression-free survival by both independent review per RECIST v1.1 and investigator assessed per modified RECIST, overall survival, 12-month overall survival, and safety. Exploratory analyses included the association between atezolizumab response and total mutation load with clinical outcomes.

Patients

Patients were eligible for enrollment in the study if they had histologically or cytologically documented locally advanced (T4b, any N; or any T, N 2-3) or metastatic (M1, Stage IV) urothelial carcinoma (including renal pelvis, ureter, urinary bladder, urethra). Eligible patients had measurable disease defined by RECIST v1.1; adequate hematologic and end-organ function; and no autoimmune disease or active infections. Formalin-fixed paraffin-embedded (FFPE) tumor specimens with sufficient viable tumor content were required prior to study enrollment. Cohort 1-specific inclusion criteria required that the patient be ineligible for treatment with a platinum-containing regimen (e.g., a cisplatin-based chemotherapy regimen, e.g., a cisplatin-based chemotherapy regimen for locally advanced or metastatic urothelial bladder cancer) based on impaired renal function, a glomerular filtration rate (GFR)<60 and >30 mL/min, a hearing loss of 25 dB at two contiguous frequencies, Grade 2 or greater peripheral neuropathy, and/or an Eastern Cooperative Oncology Group (ECOG) performance status of 2. Cohort 2-specific inclusion criteria required that the patient had disease progression during or following treatment with at least one platinum-containing regimen (e.g., gemcitabine and cisplatin (GC); methotrexate, vinblastine, doxorubicin, and cisplatin (MVAC); GemCarbo (gemcitabine and carboplatin)) for inoperable locally advanced or metastatic urothelial carcinoma or disease recurrence, a creatine clearance of 30 mL/min, and an ECOG performance status of 0 or 1. Further details concerning the clinical protocol are available at NEJM.org.

Study Assessments

Measurable and evaluable lesions were assessed and documented prior to treatment. Patients underwent tumor assessments every 9 weeks for the first 12 months following Cycle 1, Day 1. After 12 months, tumor assessments were performed every 12 weeks. Safety assessments were performed according to National Cancer Institute Common Terminology Criteria for Adverse Events (NCI CTCAE), Version 4.0. A sample of archived tumor tissues, as well as serum and plasma samples, was collected for exploratory biomarker assessments.

Somatic Mutations and Mutation Load

To identify somatic mutations, tumor samples were processed as described in Frampton et al. *Nat. Biotechnol.* 31:1023-31, 2013. Sequencing libraries were constructed to sequence and analyze samples. Tumor DNA extraction and preparation were performed externally by HistoGeneX N.V. (Antwerp Belgium). In addition to standard mutation processing, a mutation load estimation algorithm was applied that, based on the number of somatic mutations and/or rearrangements detected in Table 1 or Table 2, respectively, extrapolates to the exome or the genome as a whole. For purposes of mutation load estimation, all coding short variant alterations, base substitutions and indels detected in the genes listed in Table 1 and Table 2 were counted. Further, all coding alterations (base substitutions and indels), including synonomous alterations, in the genes listed in Table 1 and Table 2 were counted. However, numerous classes of detected alterations were not counted: non-coding alterations; alterations with known (occurring as known somatic alterations in the COSMIC database (Forbes et al. (2014) *Nucl. Acids Res.* 43:D805-11) and likely (truncations in tumor suppressor genes) functional status; known germline alterations in the dbSNP database (Sherry et al. (2001) *Nucleic Acids Res.* 29(1):308-11); germline alterations occurring with two or more counts in the ExAC database (Exome Aggregation Consortium (ExAC), Cambridge, MA); alterations that are predicted to be germline in the specimen being assessed; and alterations that are predicted to be germline in a cohort of >60,000 clinical specimens. Finally, to calculate the mutation load per megabase, the total number of mutations counted was divided by the coding region target territory of the test, which was 1.110 megabases for the current version of the test.

Mutational Load Analysis

Figure 1B:
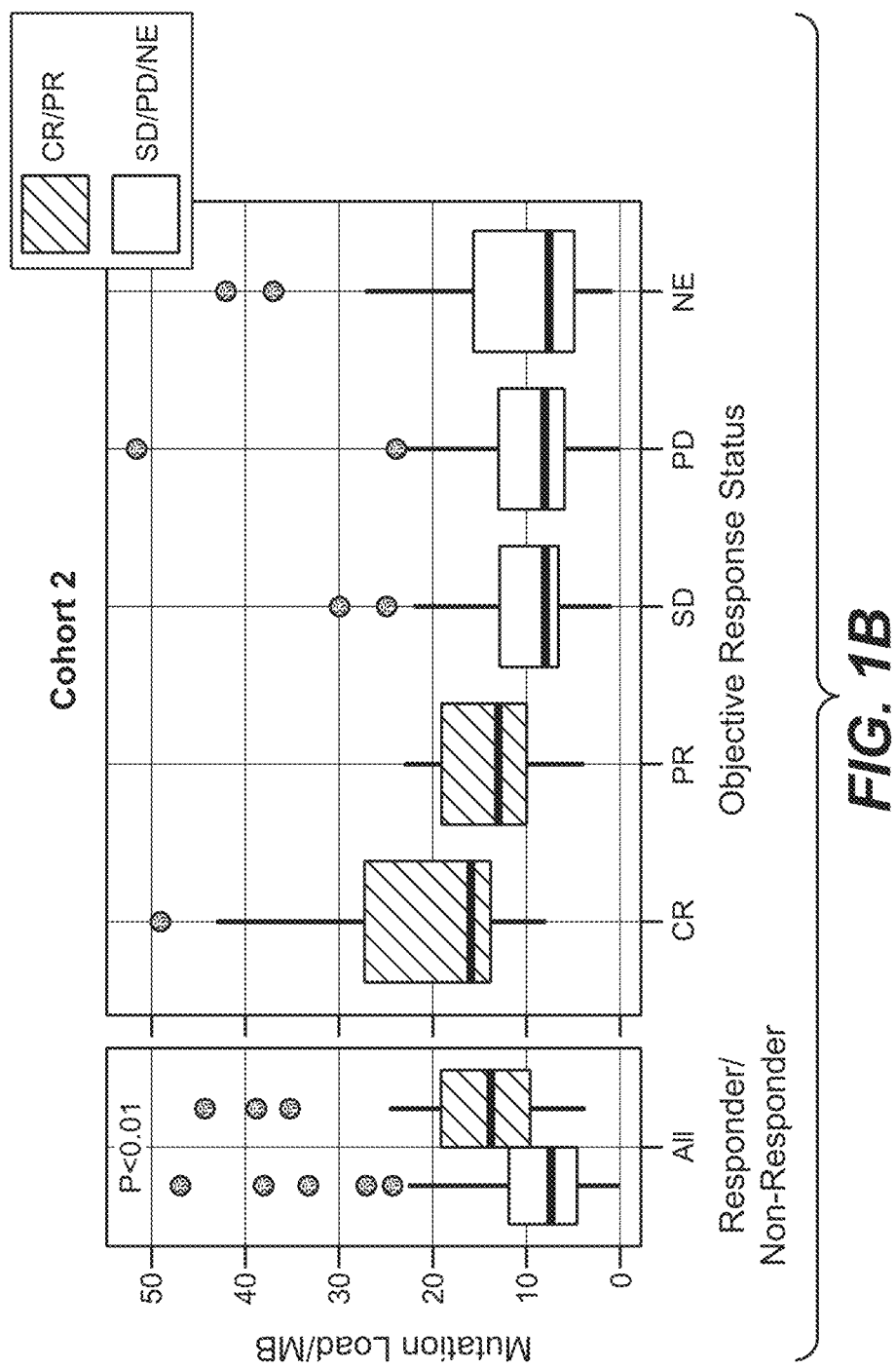
FIG. 1B is a graph showing that the median mutation load per Mb was significantly increased in Cohort 2 responders compared to Cohort 2 non-responders ($p<0.01$).
Figure 1C:
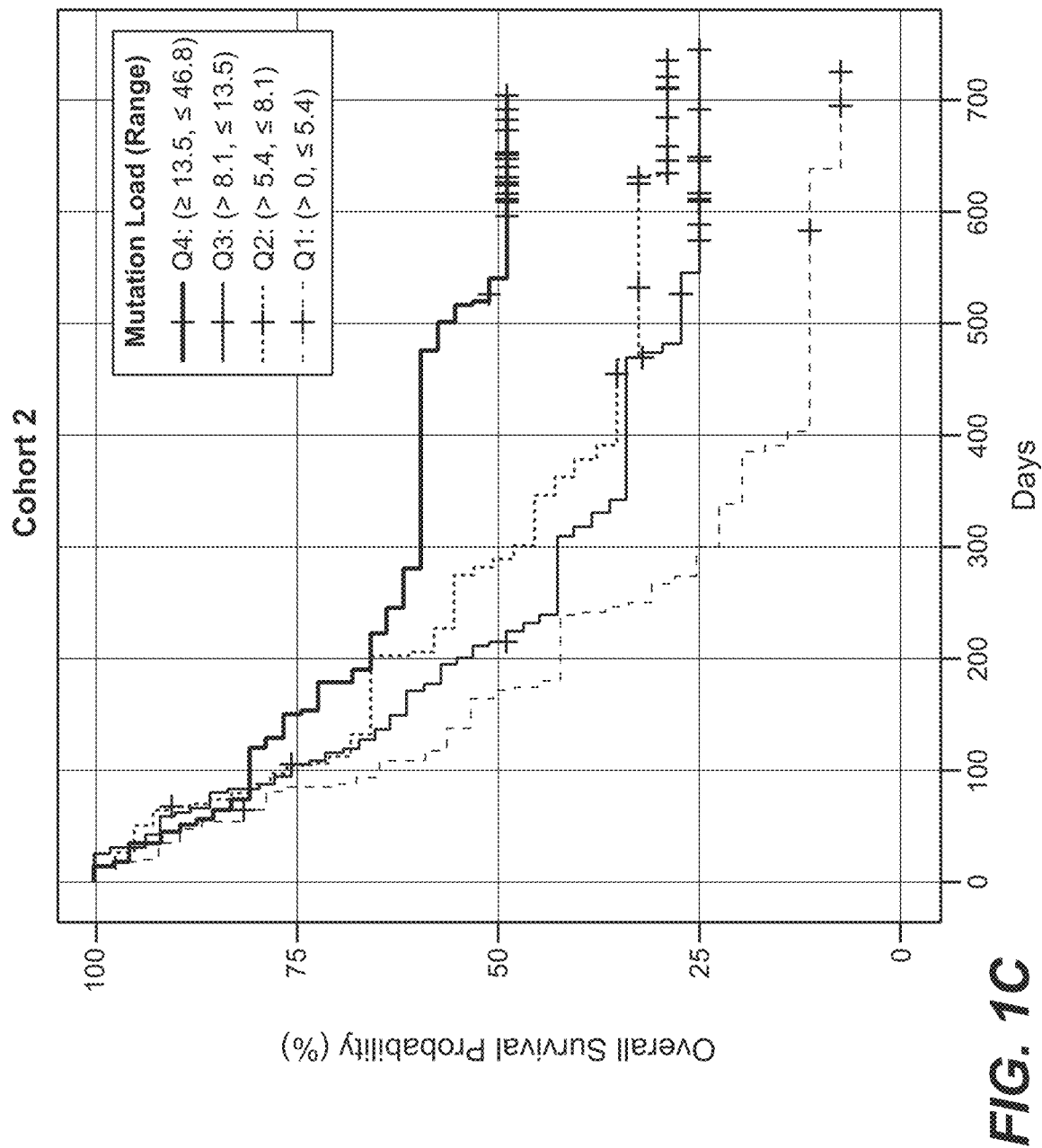
FIG. 1C is a Kaplan-Meier plot showing the overall survival (OS) probability of Cohort 2 patients having mutation load ranges in quartile 1 (Q1) ($\geq$0/Mb, $\leq$5.4/Mb), quartile 2 (Q2) (>5.4/Mb, $\leq$8.1/Mb), quartile 3 (Q3) (>8.1/Mb, $\leq$13.5/Mb), and quartile 4 (Q4) (>13.5/Mb, $\leq$46.8/Mb). Patients with the highest mutation load had significantly longer OS. $p<0.01$ for association between mutation load (quartile cut) and OS.
Figure 2A:
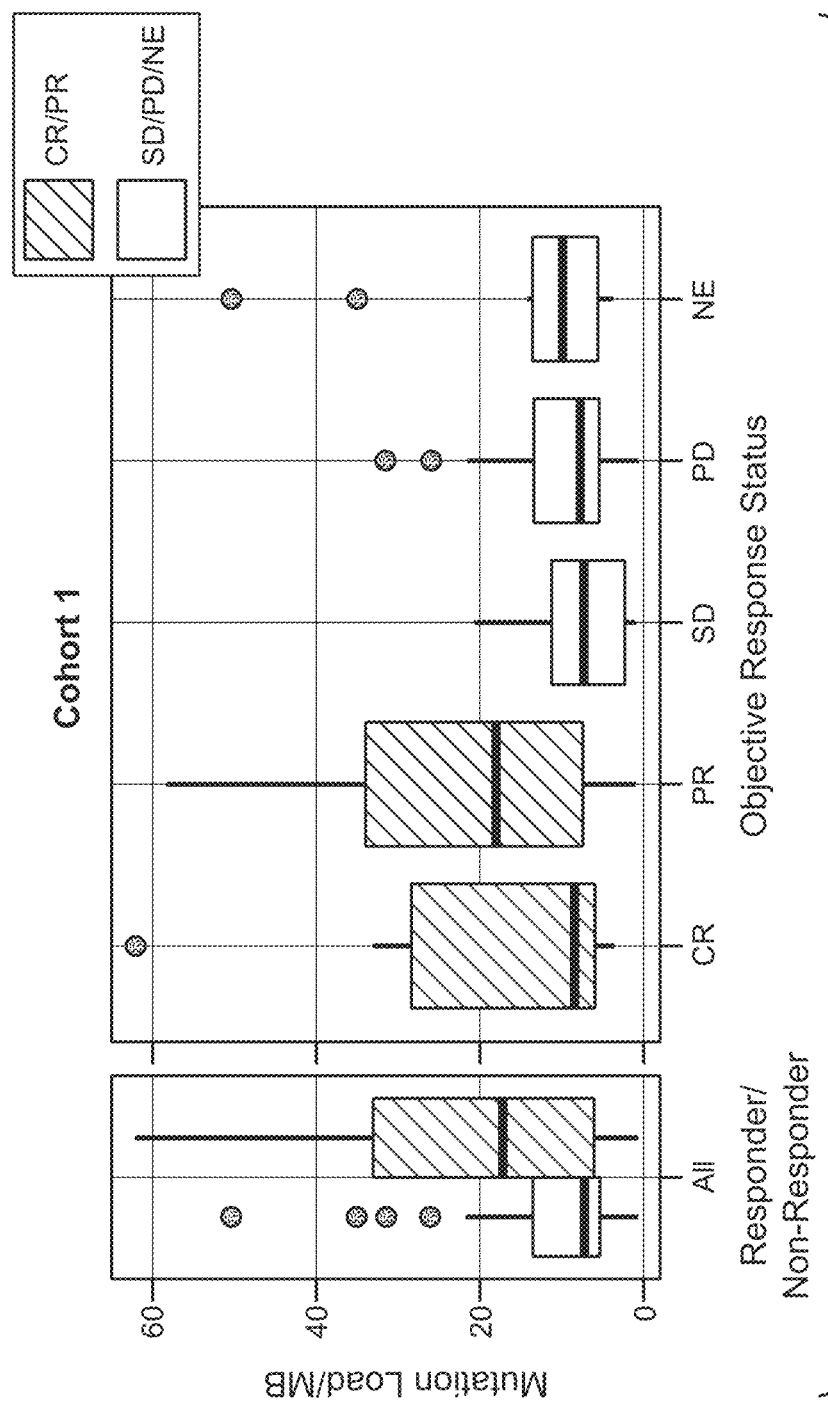
FIG. 2A is a graph showing that the median mutation load per Mb was significantly increased in Cohort 1 responders compared to Cohort 1 non-responders ($p=0.02$). The graph shows a comparison between mutation load and response (CR/PR compared to SD/PD/NE) using a Wilcoxon rank sum test due to granularity of values and skew (left panel) and median mutation load per Mb by objective response status (right panel).
Figure 2B:
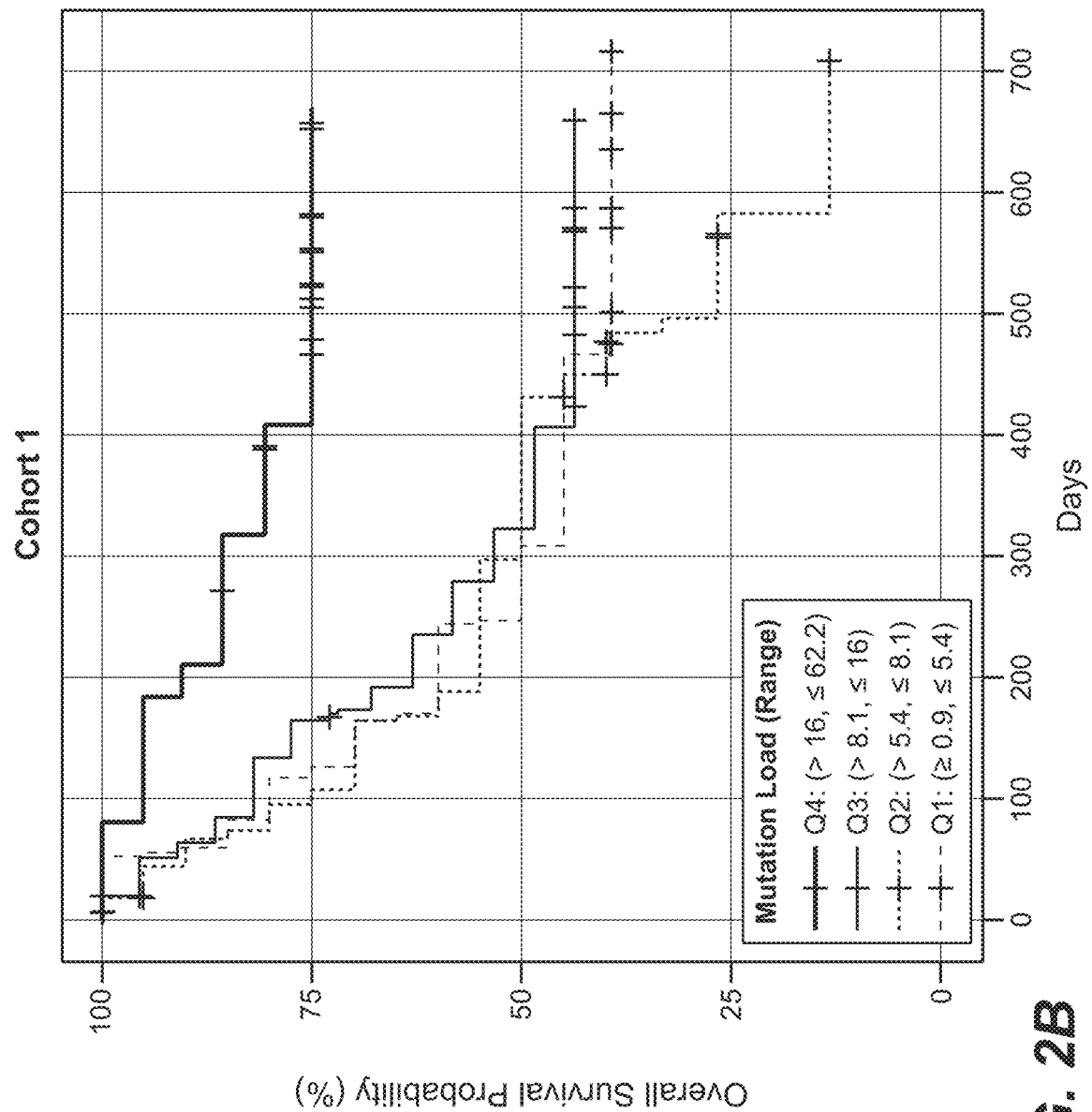
FIG. 2B is a Kaplan-Meier plot showing the OS probability of Cohort 1 patients having mutation load ranges in Q1 ($\geq$0.9/Mb, $\leq$5.4/Mb), Q2 (>5.4/Mb, $\leq$8.1/Mb), Q3 (>8.1/Mb, $\leq$16/Mb), and Q4 (>16/Mb, $\leq$62.2/Mb). Patients with the highest mutation load (Q4) had significantly longer OS compared with those in Q1-Q3. Log rank $p<0.01$ for a difference in OS between Q1-Q3 and Q4.

Mutation load was estimated in Cohort 1 and Cohort 2 patients by examining the somatic mutations and rearrangements occurring in a panel of cancer-related genes (see, Tables 1 and 2) that are representative of 3% of the exome (e.g., coding sequences). The median mutation load for Cohort 2 (310 patients) was significantly increased in responders (12.4/Mb) compared to non-responders (6.4/Mb) ($P<0.001$, FIGS. 1A-1B), and a high mutation load was associated with overall survival (OS) (FIG. 1C). FIG. 1B represents a statistical analysis of Cohort 2 patient data performed later than the statistical analysis shown in FIG. 1A. FIG. 1B incorporated the "not estimable" (NE) patient subgroup in the Cohort 2 non-responders group and similarly shows that median mutation load is increased for Cohort 2 responders compared to non-responders. Furthermore, in Cohort 2 patients smoking status did not correlate with mutation load (P=0.245) or with response (P=0.537) to atezolizumab. Similar to the Cohort 2 results, mutation load was also significantly higher in responding patients in Cohort 1 (119 patients) than in non-responders (FIG. 2A). Mutation load was associated with OS, and patients with the highest mutation load in quartile 4 had significantly longer OS compared with those in quartiles 1-3 (FIG. 2B).

Figure 3:
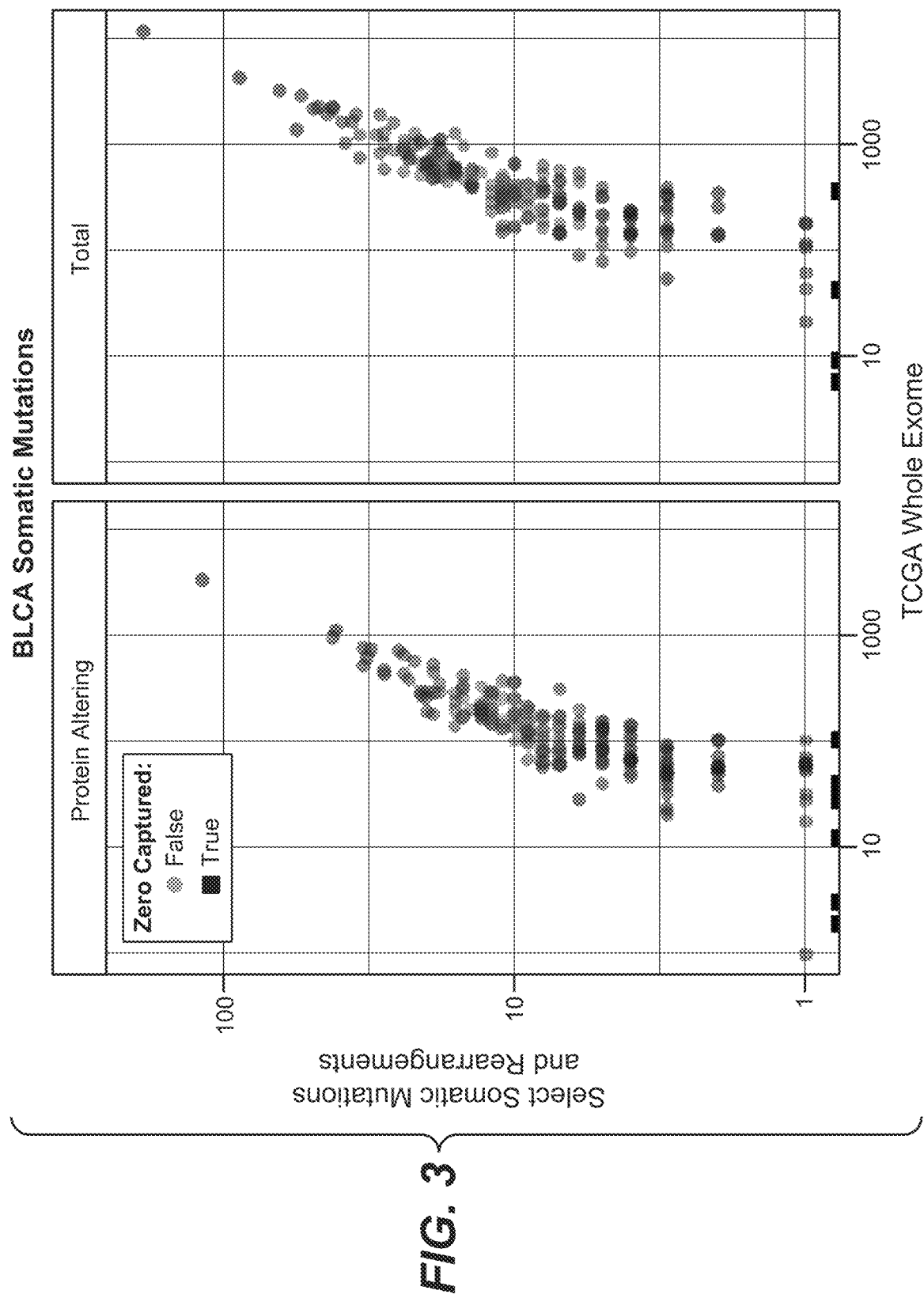
FIG. 3 is a graph showing a comparison between whole-exome and select mutations/rearrangements of the genes listed in Tables 1 and 2 in TCGA bladder urothelial carcinoma exome-seq data.

Although this targeted approach interrogated a much smaller fraction of the exome than typically used for mutation load estimation, a reanalysis of The Cancer Genome Atlas Research Network (TCGA Research Network) bladder urothelial carcinoma (BLCA) mutation data showed that whole-exome results were well-correlated with those obtained from using only the cancer-related genes listed in Tables 1 and 2 (FIG. 3). FIG. 3 compares single-nucleotide mutation counts generated from all sequences produced by TCGA with counts generated after first subsetting TCGA whole-exome data to only those reads that coincide with the genes listed in Tables 1 and 2. A comparison was made between counts of all mutations (FIG. 3, right panel) or only protein-altering mutations (FIG. 3, left panel) in the genes listed in Tables 1 and 2 or in the whole exome. Significantly fewer somatic mutations were detected when examining only those genes listed in Tables 1 and 2, however, the whole-exome counts from Tables 1 and 2 were highly correlated. As a result, the mutation load estimates generated from examining the genes listed in Tables 1 and 2 were largely equivalent to what would have been obtained with a whole-exome assay.

OTHER EMBODIMENTS

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A method of treating a patient suffering from a urothelial bladder cancer, the method comprising administering to the patient a therapeutically effective amount of a PD-L1 binding antagonist, wherein a tumor sample obtained from the patient has been determined to have an increased level of mutation load relative to a reference level of mutation load, wherein mutation load of the tumor sample reflects the level of somatic mutations in at least one-third of the genes set forth in Table 1, and wherein the PD-L1 binding antagonist is an anti-PD-L1 antibody comprising a heavy chain comprising the hypervariable region (HVR)-H1 sequence of SEQ ID NO: 19, the HVR-H2 sequence of SEQ ID NO: 20, and the HVR-H3 sequence of SEQ ID NO: 21; and a light chain comprising the HVR-L1 sequence of SEQ ID NO: 22, the HVR-L2 sequence of SEQ ID NO: 23, and the HVR-L3 sequence of SEQ ID NO: 24.

2. The method of claim 1, wherein the mutation load of the tumor sample reflects the level of somatic mutations in at least one-half, two-thirds, three-fourths, or all of the genes set forth in Table 1.

3. The method of claim 1, wherein:
(i) the somatic mutations are substitutions, deletions, and/or insertions;
(ii) the somatic mutations of the at least one gene set forth in Table 1 are protein-altering somatic mutations; or
(iii) the substitutions, deletions, and/or insertions of (i) are in coding regions.

4. The method of claim 1, wherein the tumor sample obtained from the patient has a whole-genome mutation load that is higher than a reference level whole-genome mutation load.

5. The method of claim 4, wherein the reference level whole-genome mutation load is at least about 10 mutations per megabase (Mb).

6. The method of claim 1, wherein the antibody comprises a heavy chain variable region comprising the amino acid sequence of SEQ ID NO: 25 and a light chain variable region comprising the amino acid sequence of SEQ ID NO:4.

7. The method of claim 1, further comprising administering to the patient an effective amount of a second therapeutic agent.

8. The method of claim 7, wherein the second therapeutic agent is selected from the group consisting of a cytotoxic agent, a growth-inhibitory agent, a radiation therapy agent, an anti-angiogenic agent, and combinations thereof.

9. The method of claim 1, wherein the urothelial bladder cancer is a locally advanced urothelial bladder cancer or a metastatic urothelial bladder cancer.

10. The method of claim 1, wherein the patient is ineligible for treatment with a platinum-based chemotherapeutic agent and has not received prior treatment for locally advanced or metastatic urothelial bladder cancer.

11. The method of claim 1, wherein the tumor sample is a formalin-fixed and paraffin-embedded (FFPE) tumor sample, an archival tumor sample, a fresh tumor sample, or a frozen tumor sample.

12. The method of claim 1, wherein the antibody comprises a heavy chain comprising the amino acid sequence of SEQ ID NO:32 and a light chain comprising the amino acid sequence of SEQ ID NO: 33.

13. A method of treating a patient suffering from a locally advanced or metastatic urothelial carcinoma, the method comprising administering to the patient 1200 mg of an anti-PD-L1 antibody comprising a heavy chain comprising the hypervariable region (HVR)-H1 sequence of SEQ ID NO: 19, the HVR-H2 sequence of SEQ ID NO: 20, and the HVR-H3 sequence of SEQ ID NO: 21; and a light chain comprising the HVR-L1 sequence of SEQ ID NO: 22, the HVR-L2 sequence of SEQ ID NO: 23, and the HVR-L3 sequence of SEQ ID NO: 24 intravenously on Day 1 of each 21-day cycle, wherein the patient is ineligible for treatment with a platinum-based chemotherapeutic agent and has not received prior treatment for locally advanced or metastatic urothelial carcinoma, wherein a tumor sample obtained from the patient has been determined to have an increased level of mutation load relative to a reference level of mutation load, and wherein the mutation load of the tumor sample reflects the level of somatic mutations in at least one-third of the genes set forth in Table 1.

* * * * *